United States Patent [19]
Wallner et al.

[11] Patent Number: 5,914,111
[45] Date of Patent: Jun. 22, 1999

[54] CD2-BINDING DOMAIN OF LYMPHOCYTE FUNCTION ASSOCIATED ANTIGEN-3

[75] Inventors: Barbara P. Wallner, Cambridge; Glenn T. Miller, Haverhill; Margaret D. Rosa, Winchester, all of Mass.

[73] Assignee: Biogen Inc., Cambridge, Mass.

[21] Appl. No.: 08/459,657

[22] Filed: Jun. 2, 1995

Related U.S. Application Data

[62] Division of application No. 07/940,861, Oct. 21, 1992, Pat. No. 5,547,853, which is a continuation-in-part of application No. 07/770,967, Oct. 7, 1991, abandoned, which is a continuation-in-part of application No. 07/667,971, filed as application No. PCT/US92/02050, Mar. 12, 1991, abandoned.

[51] Int. Cl.[6] .................. A61K 39/395; A61K 38/16; C12N 15/62; C07K 14/705
[52] U.S. Cl. .................. 424/134.1; 424/153.1; 424/173.1; 424/182.1; 424/185.1; 424/192.1; 435/69.7; 514/12; 530/324; 530/387.1
[58] Field of Search ............... 530/387, 3, 324, 530/325, 326, 327, 328, 350, 387.1; 514/15, 14, 13, 12; 424/134.1, 153.1, 172.1, 173.1, 182.1, 185.1, 192.1; 435/69.7

[56] References Cited

U.S. PATENT DOCUMENTS

| | | |
|---|---|---|
| 4,816,567 | 3/1989 | Cabilly et al. . |
| 4,956,281 | 9/1990 | Wallner et al. . |
| 5,116,964 | 5/1992 | Capon et al. . |
| 5,190,859 | 3/1993 | Dustin et al. . |
| 5,225,538 | 7/1993 | Capon et al. . |

FOREIGN PATENT DOCUMENTS

| | | |
|---|---|---|
| 314 317 | 5/1989 | European Pat. Off. . |
| 325 262 | 7/1989 | European Pat. Off. . |
| 345 466 A2 | 12/1989 | European Pat. Off. . |
| 368 684 A4 | 5/1990 | European Pat. Off. . |
| WO 88/09820 | 12/1988 | WIPO . |
| WO 89/02922 | 4/1989 | WIPO . |
| WO 90/02181 | 3/1990 | WIPO . |
| WO 90/07517 | 7/1990 | WIPO . |
| WO 90/12099 | 10/1990 | WIPO . |
| WO 91/11461 | 8/1991 | WIPO . |
| WO 92/07581 | 5/1992 | WIPO . |

OTHER PUBLICATIONS

Rudinger, J. in Peptide Hormones, Parson, J. A. (Ed.), University Park Press, Baltimore, MD, pp. 1–7, 1976.

Richard J. Kaplon et al.; "Short Course Single Agent Therapy with an LFA–3–IgG$_1$ Fusion Protein Prolongs Primate Cardiac Allograft Survival[1,2]" (Transplantation—February 15, 1996 pp. 356–363).

A. Benedict Cosimi et al.; "In Vivo Effects of Monoclonal Antibody to ICAM–1 (CD54) in Nonhuman Primates with Renal Allografts[1]" (The Journal of Immunology—June 15, 1990 pp. 4604–4612).

Keith A. Reimann et al.; "In Vivo Administration of Lymphocyte–Specific Monoclonal Antibodies in Nonhuman Primates" (Transplantation—December 1989 pp. 906–912).

A. Benedict Cosimi et al.; "Prolonged survival of nonhuman primate renal allograft recipients treated only with anti–CD4 monoclonal antibody" (Surgery 1990 pp. 406–414).

Barsoum, J., "Laboratory Methods: Introduction of Stable High–Copy–Number DNA into Chinese Hamster Ovary Cells by Electroporation," *DNA and Cell Biology*, 9, pp. 293–300 (1990).

Bierer, B. E., et al., "Expression of the T–Cell Surface Molecule CD2 and an Epitope–Loss CD2 Mutant to Define the Role of Lymphocyte Function–Associated Antigen 3 (LFA–3) in T–Cell Activation," *Proc. Natl. Acad. Sci. USA*, 85, pp. 1194–1198 (Feb. 1988).

Bressler, P., et al., "Anti–CD2 Receptor Antibodies Activate the HIV Long Terminal Repeat in T Lymphocytes," *J. Immunol.*, 147, pp. 2290–2294 (Oct. 1, 1991).

Brod, S. A., et al., "T–T Cell Interactions Are Mediated By Adhesion Molecules," *Eur. J. Immunol.*, 20, pp. 2259–2268 (1990).

Dailey, L., and C. Basilico, "Sequences in the Polyomavirus DNA Regulatory Region Involved in Viral DNA Replication and Early Gene Expression," *J. Virology*, 54, pp. 739–749 (Jun. 1985).

Denning, S. M., et al., "Monoclonal Antibodies to CD2 and Lymphocyte Function–Associated Antigen 3 Inhibit Human Thymic Epithelial Cell–Dependent Mature Thymocyte Activation," *J. Immunol.*, 139, pp. 2573–2578 (Oct. 15, 1987).

Dente, L., et al., "pEMBL: a New Family of Single Stranded Plasmids," *Nucleic Acids Research*, 11, pp. 1645–1655 (1983).

Dustin, M.L., et al., "Correlation of CD2 Binding and Functional Properties of Multimeric and Monomeric Lymphocyte Function–Associated Antigen 3," *J. Exp. Med.*, 169, pp. 503–517 (Feb. 1989).

Dustin, M. L., et al., "Purified Lymphocyte Function–Associated Antigen 3 Binds to CD2 and Mediates T Lymphocyte Adhesion," *J. Exp. Med.*, 165, pp. 677–692 (Mar. 1987).

Enea, V. and N. D. Zinder, "Interference Resistant Mutants of Phage f1," *Virology*, 122, pp. 222–226 (1982).

(List continued on next page.)

Primary Examiner—Frank C. Eisenschenk
Assistant Examiner—Evelyn Rabin
Attorney, Agent, or Firm—Biogen, Inc.; Warren A. Kaplan

[57] ABSTRACT

Polypeptides and proteins comprising the CD2-binding domain of LFA-3 are disclosed. DNA sequences that code on expression for those polypeptides and proteins, methods of producing and using those polypeptides and proteins, and therapeutic and diagnostic compositions are also disclosed. Deletion mutants unable to bind CD2 and methods for their use are also disclosed. In addition, fusion proteins which comprise the CD2-binding domain of LFA-3 and a portion of a protein other than LFA-3, DNA sequences encoding those fusion proteins, methods for producing those fusion proteins, and uses of those fusion proteins are disclosed.

6 Claims, 31 Drawing Sheets

OTHER PUBLICATIONS

Geider, K., et al., "A Plasmid Cloning System Utilizing Replication and Packaging Functions of the Filamentous Bacteriophage fd," *Gene*, 33, pp. 341–349 (1985).

Kent, S.B.H., "Chemical Synthesis of Peptides And Proteins," *Ann. Rev. Biochem.*, 57, pp. 957–989 (1988).

Kohler, G. And C. Milstein, "Continuous Cultures of Fused Cells Secreting Antibody of Predefined Specificity," *Nature*, 256, pp. 495–497 (Aug. 7, 1975).

Krensky, A. M. et al., "The Functional Significance, Distribution, and Structure of LFA–1, LFA–2, and LFA–3: Cell Surface Antigens Associated With CTL–Target Interations," *J. Immunol.*, 131, pp. 611–616 (Aug. 1983).

Lambert, J. M. et al., "Purified Immunotoxins That Are Reactive With Human Lymphoid Cells," *J. Biol. Chem.*, 260, pp. 12035–12041 (1985).

Liao, T., et al., "Modification of Sialyl Residues of Sialoglycoprotein(s) of the Human Erythrocyte Surface," *J. Biol. chem.*, 248, pp. 8247–8253 (Dec. 10, 1973).

Moroney, S.E., et al., "Modification of the Binding Site(s) of Lectins by an Affinity Column Carrying an Activated Galactose–Terminated Ligand," *Biochemistry*, 26, pp. 8390–8398 (1987).

Morrison, S. L., "Transfectomas Provide Novel Chimeric Antibodies," *Science*, 229, pp. 1202–1207 (Sep. 20, 1985).

Pepinsky, R. B., et al., "The Increased Potency of Cross–Linked Lymphocyte Function–Associated Antigen–3 (LFA–3) Multimers Is A Direct Consequence of Changes in Valency," *J. Biol. Chem.*, 266, pp. 18244–18249 (Sep. 1991).

Peterson, A.S., "Genetic and Biochemical Analysis of CD2, LFA–3 Interaction," In *Genetic Analysis of CD2/LFA and CD4/HIV Interactions*, Chapter 1, pp. 1–13, Figure 1A (Harvard University, Cambridge, Massachusetts 1988).

Ramakrishnan, S. and L. L. Houston, "Comparison of the Selective Cytotoxic Effects of Immunotoxins Containing Ricin A Chain or Pokeweed Antiviral Protein and Anti–Thy 1.1 Monoclonal Antibodies," *Cancer Research*, 44, pp. 201–208 (Jan. 1984).

Reichlin, M., "Use of Glutaraldehyde as a Coupling Agent for Proteins and Peptides," In *Methods in Enzymology*, 70, pp. 159–165 (1980).

Sanchez–Madrid, F. et al., "Three Distinct Antigens Associated with Human T–Lymphocyte–Mediated Cytolysis: LFA–1, LFA–2, and LFA–3," *Proc. Natl. Acad. Sci. USA*, 79, pp. 7489–7493 (Dec. 1982).

Seed, B., "An LFA–3 cDNA Encodes a Phospholipid–Linked Membrane Protein Homologous to its Receptor CD2," *Nature*, 329, pp. 840–842 (1987).

Seed, B. and A. Aruffo, "Molecular Cloning of the CD2 Antigen, the T–Cell Erythrocyte Receptor, By a Rapid Immunoselection Procedure," *Proc. Natl. Acad. Sci. USA*, 84, pp. 3365–3369 (May 1987).

Selvaraj, P., et al., "The T Lymphocyte Glycoprotein CD2 Binds the Cell Surface Ligand LFA–3," *Nature*, 326, pp. 400–403 (Mar. 1987).

Shaw, S. and G. E. Ginther Luce, "The Lymphocyte Function–Associated Antigen (LFA)–1 and CD2/LFA–3 Pathways of Antigen–Independent Human T Cell Adhesion," *J. Immunol.*, 139, pp. 1037–1045 (Aug. 15, 1987).

Short, J. M., et al., "ZAP: A Bacteriophage Expression Vector with In Vivo Excision Properties," *Nucleic Acids Research*, 16, pp. 7583–7600 (1988).

Springer, T. A., et al., "The Lymphocyte Function–Associated LFA–1, CD2, and LFA–3 Molecules: Cell Adhesion Receptors of the Immune System," In *Ann. Rev. Immunol.*, 5, pp. 223–252 (1987).

Srinivasachar, K. and D. M. Neville, Jr., "New Protein Cross–Linking Reagents That Are Cleaved by Mild Acid," *Biochemistry*, 28, pp. 2501–2509 (1989).

Richardson, N.E., et al., "Adhesion Domain of Human T11 (CD2) is Encoded by a Single Exon," *Proc. Natl. Acad. Sci. (USA)*, 85, pp. 5176–5180 (1988).

Vollger, L. W., et al., "Thymocyte Binding to Human Thymic Epithelial Cells is Inhibited by Monoclonal Antibodies to CD–3 and LFA–3 Antigens," *J. Immunol.*, 138, pp. 358–363 (Jan. 15, 1987).

Wallner, B. P., et al., "Primary Structure of Lymphocyte Function–Associated Antigen 3 (LFA–3)," *J. Exp. Med.*, 166, pp. 923–932 (Oct. 1987).

Wang, X. et al., "A Vector That Expresses Secreted Proteins on the Cell Surface," *DNA*, 8, pp. 753–758 (Dec. 1989).

FIG. 1A-1

```
  1  CGACGAGCCATGGTTGCTGGGAGCGACGCGGGGGCGGGCCCTGGGGTCCT     50
        MetValAlaGlySerAspAlaGlyAlaGlyArgAlaLeuGlyValLe
        -28

51  CAGCGTGGTCTGCCTGCTGCACTGCTTGGTTCATCAGCTGTTTTTCCC    100
     uSerValValCysLeuLeuHisCysPheGlyPheIleSerCysPheSerG    3
                                                      +1

101  AACAAATATGGTGTGTGTATGGGAATGTAACTTTCCATGTACCAAGC     150
     lnGlnIleTyrGlyValValTyrGlyAsnValThrPheHisValProSer   19
                                      M53

151  AATGTGCCTTAAAGAGGTCCTATGGAAAAACAAAGGATAAAGTTGC      200
     AsnValProLeuLysGluValLeuTrpLysLysGlnLysAspLysValAl   36
                                        M55

201  AGAACTGGAAAATTCTGAATTCAGAGCTTTCTCATCTTTAAAAATAGGG   250
     aGluLeuGluAsnSerGluPheArgAlaPheSerSerPheLysAsnArgV   53
                         M56

251  TTTATTTAGACACTGTGTCAGGTAGCCTCACTATCTACAACTTAACATCA  300
     alTyrLeuAspThrValSerGlySerLeuThrIleTyrAsnLeuThrSer   69
                M57                                 M58
```

```
301  TCAGATGAAGATGAGTATGAAATGGAATTACTGATACCAT   350
     SerAspGluAspGluTyrGluMetGluSerProAsnIleThrAspThrMe    86
                            M59                    M60

351  GAAGTTCTTTCTTTATGCTTGAGTCTCTTCCATCTCCACACTAACTT   400
     tLysPhePheLeuTyrValLeuGluSerLeuProSerProThrLeuThrC   103
                     M61

401  GTGCATTGACTAATGGAAGCATTGAAGTCCAATGCATGATACCAGAGCAT   450
     ysAlaLeuThrAsnGlySerIleGluValGlnCysMetIleProGluHis   119
                M62                         M63

451  TACAACAGCCATCGAGGACTTATAATGTACTCATGGGATTGTCCTATGGA   500
     TyrAsnSerHisArgGlyLeuIleMetTyrSerTrpAspCysProMetGl   136
                      M64                        M65

501  GCAATGTAAACGTAACTCAACCAGTATATATTTTAAGATGGAAAATGATC   550
     uGlnCysLysArgAsnSerThrSerIleTyrPheLysMetGluAsnAspL   153
                     M66
```

```
551  TTCCACAAAAATACAGTGTACTCTTAGCAATCCATTATTAATACAACA      600
     euProGlnLysIleGlnCysThrLeuSerAsnProLeuPheAsnThrThr    169
                      M90                      M91

601  TCATCAATCATTTGACAACCTGTATCCCAAGCAGCGGTCATTCAAGACA     650
     SerSerIleIleLeuThrThrCysIleProSerSerGlyHisSerArgHi    186
                      M92

651  CAGATATGCACTTATACCCATTAGCAGTAATTACAACATGTATTG         700
     sArgTyrAlaLeuIleProIleProLeuAlaValIleThrThrCysIleV    203
                              Transmembrane 701  TGCTGTATATGAATGGTATTCTGAAATGTGAACAGAAAACCAGACGAACC    750
     alLeuTyrMetAsnGlyIleLeuLysCysAspArgLysProAspArgThr    219

751  AACTCCAATTGATTGGTAACAGAAGATGAAGACAACAGCATAACTAAATT    800
     AsnSerAsn                                              222

801  ATTTTAAAAACTAAAAAGCCATCTGATTTCTCATTTGAGTATTACAATTT    850

851  TTGAACAACTGTTGGAAATGTAACTTGAAGCAGCTGCTTAAGAAGAAAT     900

901  ACCCACTAACAAAGAACAAGCATTAGTTTTGGCTGTCATCAACTTATTAT    950

951  ATGACTAGGTGCTTGCTTTTTTTTGTCAGTAAATTGTTTTTACTGATGATG   1000

1001 TAGATACTTTTGTAAATAAATGTAAATATGTACACAAGTG     1040
```

CHO M57        M16,3

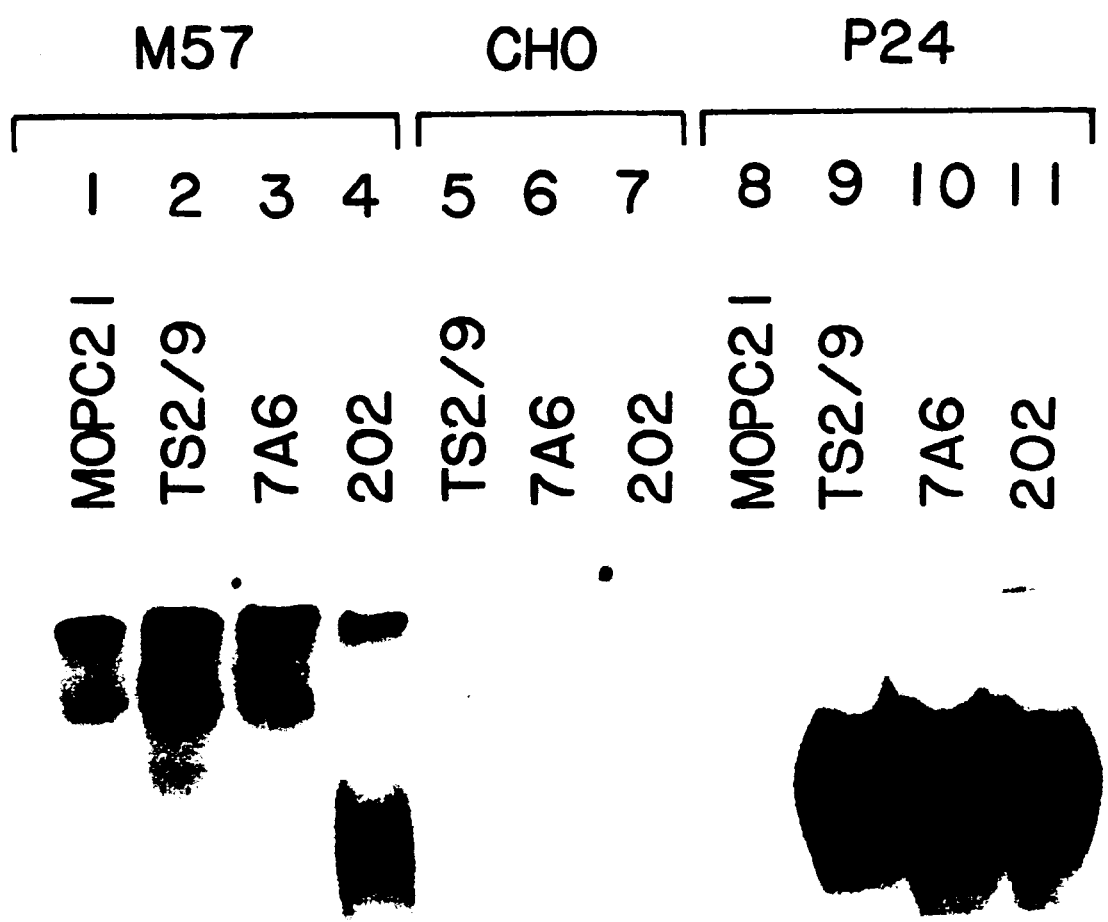

FIG. 6A-1

```
1   CGACGAGCCATGGTTGCTGGGAGCGACGCGGGCGGCCCTGGGGTCCT                    50
              MetValAlaGlySerAspAlaGlyArgAlaLeuGlyValLe
              -28

51  CAGGCGTGGTCTGCCTGCACTGTGTTGGTTTCATCAGCTGTTTTCCC                   100
    uSerValValCysLeuLeuHisCysPheGlyPheIleSerCysPheSerG                  3
                                                    +1

101 AACAAATATATGGTGTGTATGGGAATGTAACTTTCCATGTACCAAGC                   150
    lnGlnIleTyrGlyValValTyrGlyAsnValThrPheHisValProSer                 19

151 AATGTGCCTTTAAAGAGGTCCTATGGAAAAACAAAAGGATAAAGTTGC                  200
    AsnValProLeuLysGluValLeuTrpLysLysGlnLysAspLysValAl                 36

201 AGAACTGGAAATTCTGAATTCAGAGCTTTCTCATCTTTAAAAATAGGG                  250
    aGluLeuGluAsnSerGluPheArgAlaPheSerSerPheLysAsnArgV                 53
                                  M 100

251 TTTATTTAGACACTGTGTCAGGTAGCCTCACTATCTACAACTTAACATCA                300
    alTyrLeuAspThrValSerGlySerLeuThrIleTyrAsnLeuThrSer                 69
```

```
301  TCAGATGAAGATGAGTATGAAATGGAATCGCCAAATATTACTGATACCAT   350
     SerAspGluAspGluTyrGluMetGluSerProAsnIleThrAspThrMe    86

351  GAAGTTCTTTCTTTATGTGCTTGAGTCTCTTCCATCTCCCACACTAACTT   400
     tLysPhePheLeuTyrValLeuSerLeuProSerProThrLeuThrC      103
                                                   M 101

401  GTGCATTGACTAATGGAAGCATTGAAGTCCAATGCATGATACCAGAGCAT   450
     ysAlaLeuThrAsnGlySerIleGluValGlnCysMetIleProGluHis   119

451  TACAACAGCCATCGAGGACTTATAATGTACTCATGGGATTGTCCTATGGA   500
     TyrAsnSerHisArgGlyLeuIleMetTyrSerTrpAspCysProMetGl   136

501  GCAATGTAAACGTAACTCAACCAGTATATATTTTAAGATGGAAAATGATC   550
     uGlnCysLysArgAsnSerThrSerIleTyrPheLysMetGluAsnAspL   153
                                                   M 102
```

```
551  TTCCACAAAAATACAGTGTACTCTTAGCAATCCATTATTTAATACAACA          600
     euProGlnLysIleGlnCysThrLeuSerAsnProLeuPheAsnThrThr         169
601  TCATCAATCATTTGACAACCTGTATCCCAAGCAGCGGTCATTCAAGACA          650
     SerSerIleIleLeuThrThrCysIleProSerSerGlyHisSerArgHi         186
651  CAGATATGCACTTATACCCATTAGCAGTAATTACAACATGTATTG              700
     sArgTyrAlaLeuIleProIleProLeuAlaValIleThrThrCysIleV         203
701  TGCTGTATATGAATGGTATTCTGAAATGTGACAGAAAACCAGACAGAACC         750
     alLeuTyrMetAsnGlyIleLeuLysCysAspArgLysProAspArgThr         219
751  AACTCCAATTGATTGGTAACAGAAGATGAAGACAACAGCATAACTAAATT         800
     AsnSerAsn                                                   222
801  ATTTTAAAAACTAAAAAGCCATCTGATTTCTCATTTGAGTATTACAATTT         850
851  TTGAACAACTGTTGGAAATGTAACTTGAAGCAGCTGCTTTAAGAAGAAAT         900
901  ACCCACTAACAAAGAACAAGCATTAGTTTTGGCTGTCATCAACTTATTAT         950
951  ATGACTAGGTGCTTGCTTTTTTGTCAGTAAATTGTTTTTACTGATGATG          1000
1001 TAGATACTTTTGTAAATAAATGTAAATATGTACACAAGTG                   1040
```

FIG. 9A

```
  1  GCGGCCGCCGACGAGCCATGGTGGCTGGGAGGACGCGGGGCCCTG       50
                       MetValAlaGlySerAspAlaGlyArgAlaLeu

51  GGGGTCCTCAGCGTGGTCTGCCTGCCACTGCTTTGGTTTCATCAGCTG    100
     GlyValLeuSerValValCysLeuLeuHisCysPheGlyPheIleSerCy

101  TTTTCCACAAATATGTGTGTGTGTATGGAATGTAACTTTCCATG        150
     sPheSerGlnGlnIleTyrGlyValValTyrGlyAsnValThrPheHisV
     +1

151  TACCAAGCAATGTGCCTTTAAAAGAGGTCCTATGGAAAAACAAAAGGAT   200
     alProSerAsnValProLeuLysGluValLeuTrpLysLysGlnLysAsp

201  AAAGTTGCAGAACTGGAAATTCTGAATTCAGAGCTTTCTCATCTTTTAA   250
     LysValAlaGluLeuGluAsnSerGluPheArgAlaPheSerSerPheLy
                                                   +50

251  AAATAGGGTTTATTTAGACACTGTCAGGTAGCCTCACTACTATCTACAACT 300
     sAsnArgValTyrLeuAspThrValSerGlySerLeuThrIleTyrAsnL

301  TAACATCATCAGATGAAGATGAGTATGAAATGGAATCGCCAAATATTACT  350
     euThrSerSerAspGluAspGluTyrGluMetGluSerProAsnIleThr

351  GATACCATGAAGTTCTTTTATGCTTGAGTCTCTTCCATCTCCCAC       400
     AspThrMetLysPhePheLeuTyrValLeuGluSerLeuProSerProTh
                                                   +100
```

```
401  ACTAACTTGTGCATTGACTAATGGAAGCATTGAAGTCCAATGCATGATAC  450
     rLeuThrCysAlaLeuThrAsnGlySerIleGluValGlnCysMetIleP
451  CAGAGCATTACAACAGCCATCGAGGACTTATAATGTACTCATGGATTGT   500
     roGluHisTyrAsnSerHisArgGlyLeuIleMetTyrSerTrpAspCys
                       PIM3
501  CCTATGGAGCAATGTAAACGTAACTCAACCAGTATATATTTAAGATGA    550
     ProMetGluGlnCysLysArgAsnSerThrSerIleTyrPheLysMetGl
                                                  +150
551  AAATGATCTTCCACAAAAATACAGTGTACTCTTAGCAATCCATTATTTA   600
     uAsnAspLeuProGlnLysIleGlnCysThrLeuSerAsnProLeuPheA
601  ATACAACATCATCAATCATTTGACAACCTGTATCCCAAGCAGGGTCAT    650
     snThrThrSerSerIleIleLeuThrThrCysIleProSerSerGlyHis
651  TCAAGACACAGATATGCACTTATACCACCATTAGCAGTAATTACAAC     700
     SerArgHisArgTyrAlaLeuIleProIleProLeuAlaValIleThrTh
                                                  +200
701  ATGTATTGTGCTGTATATGAATGGTATGTGTCTTTTTAAAACAAAATAG   750
     rCysIleValLeuTyrMetAsnGlyMetTyrAlaPhe
751  TTTGAAAACTTGCATTGTTTTCCAAGGTCAGAAAAATAGTTTAAGGATGA  800
801  AAATAAAGTTTGAAATTTAGACATTTGAAAAAAAAAAAAAAAAAAAAAA   850
851  AAAAAGCGGCCGC                                       863
```

```
          LFA-3     .         .         .         .         .
  1   ATGGTTGCTGGGAGCGACGCGGGGCGGGCCCTGGGGTCCTCAGCGTGGT    50
      MetValAlaGlySerAspAlaGlyArgAlaLeuGlyValLeuSerValVa
                    .         .         .         .         .
 51   CTGCCTGCTGCACTGCTTTGGTTTCATCAGCTGTTTTCCCAACAAATAT   100
      lCysLeuLeuHisCysPheGlyPheIleSerCysPheSerGlnGlnIleT
                    .         .         .         .         .
101   ATGGTGTTGTGTATGGGAATGTAACTTTCCATGTACCAAGCAATGTGCCT   150
      yrGlyValValTyrGlyAsnValThrPheHisValProSerAsnValPro
                    .         .         .         .         .
151   TTAAAAGAGGTCCTATGGAAAAAACAAAAGGATAAAGTTGCAGAACTGGA   200
      LeuLysGluValLeuTrpLysLysGlnLysAspLysValAlaGluLeuGl
                    .         .         .         .         .
201   AAATTCTGAATTCAGAGCTTTCTCATCTTTTAAAAATAGGGTTTATTTAG   250
      uAsnSerGluPheArgAlaPheSerSerPheLysAsnArgValTyrLeuA
                    .         .         .         .         .
251   ACACTGTGTCAGGTAGCCTCACTATCTACAACTTAACATCATCAGATGAA   300
      spThrValSerGlySerLeuThrIleTyrAsnLeuThrSerSerAspGlu
                    .         .         .         .         .
301   GATGAGTATGAAATGGAATCGCCAAATATTACTGATACCATGAAGTTCTT   350
      AspGluTyrGluMetGluSerProAsnIleThrAspThrMetLysPhePh
        LFA-3 <--.--> Hinge.             .      <--.--> CH2   .
351   TCTTTATGTC|GACAAAACTCACACATGCCCACCGTGCCC|AGCACCTGAAC   400
      eLeuTyrVal|AspLysThrHisThrCysProProCysPr|oAlaProGluL
                    .         .         .         .         .
401   TCCTGGGGGGACCGTCAGTCTTCCTCTTCCCCCCAAAACCCAAGGACACC   450
      euLeuGlyGlyProSerValPheLeuPheProProLysProLysAspThr
                    .         .         .         .         .
451   CTCATGATCTCCCGGACCCCTGAGGTCACATGCGTGGTGGTGGACGTGAG   500
      LeuMetIleSerArgThrProGluValThrCysValValValAspValSe
          .         .         .         .         .         .
501   CCACGAAGACCCTGAGGTCAAGTTCAACTGGTACGTGGACGGCGTGGAGG   550
      rHisGluAspProGluValLysPheAsnTrpTyrValAspGlyValGluV
```

FIG. 12B

```
551  TGCATAATGCCAAGACAAAGCCGGGGAGGAGCAGTACAACAGCACGTAC   600
     alHisAsnAlaLysThrLysProArgGluGluGlnTyrAsnSerThrTyr

601  CGGGTGGTCAGCGTCCTCACCGTCCTGCACCAGGACTGGCTGAATGGCAA   650
     ArgValValSerValLeuThrValLeuHisGlnAspTrpLeuAsnGlyLy

651  GGAGTACAAGTGCAAGGTCTCCAACAAAGCCCTCCCAGCCCCCATCGAGA   700
     sGluTyrLysCysLysValSerAsnLysAlaLeuProAlaProIleGluL
                                    CH2 ──▶ CH3

701  AAACCATCTCCAAAGCAAAGGGCAGCCCCGAGAACCACAGGTGTACACC   750
     ysThrIleSerLysAlaLysGlyGlnProArgGluProGlnValTyrThr

751  CTGCCCCCATCCCGGGATGAGCTGACCAAGAACCAGGTCAGCCTGACCTG   800
     LeuProProSerArgAspGluLeuThrLysAsnGlnValSerLeuThrCy

801  CCTGGTCAAAGGCTTCTATCCCAGCGACATCGCCGTGGAGTGGGAGAGCA   850
     sLeuValLysGlyPheTyrProSerAspIleAlaValGluTrpGluSerA

851  ATGGGCAGCCGGAGAACAACTACAAGACCACCCCTCCCGTGCTGGACTCC   900
     snGlyGlnProGluAsnAsnTyrLysThrThrProProValLeuAspSer

901  GACGGCTCCTTCTTCCTCTACAGCAAGCTCACCGTGGACAAGAGCAGGTG   950
     AspGlySerPhePheLeuTyrSerLysLeuThrValAspLysSerArgTr

951  GCAGCAGGGGAACGTCTTCTCATGCTCCGTGATGCATGAGGCTCTGCACA   1000
     pGlnGlnGlyAsnValPheSerCysSerValMetHisGluAlaLeuHisA

1001 ACCACTACACGCAGAAGAGCCTCTCCCTGTCTCCGGGTAAATGAGTGCGG   1050
     snHisTyrThrGlnLysSerLeuSerLeuSerProGlyLys
```

FIG. 13

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
          (A) LENGTH: 10 amino acids
          (B) TYPE: amino acid
          (C) STRANDEDNESS: single
          (D) TOPOLOGY: linear (iii) HYPOTHETICAL: NO (iv) ANTI-SENSE: NO (xi) SEQUENCE DESCRIPTION: SEQ ID NO:1:

Asn Arg Val Tyr Leu Asp Thr Val Ser Gly
1               5                   10

(2) INFORMATION FOR SEQ ID NO:2:

(i) SEQUENCE CHARACTERISTICS:
          (A) LENGTH: 50 amino acids
          (B) TYPE: amino acid
          (C) STRANDEDNESS: single
          (D) TOPOLOGY: linear (iii) HYPOTHETICAL: NO (iv) ANTI-SENSE: NO (xi) SEQUENCE DESCRIPTION: SEQ ID NO:2:

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Ala Glu Leu Glu Asn Ser Glu Phe Arg Ala Phe Ser Ser
        35                  40                  45

Phe Lys
    50

(2) INFORMATION FOR SEQ ID NO:3:

(i) SEQUENCE CHARACTERISTICS:
          (A) LENGTH: 10 amino acids
          (B) TYPE: amino acid
          (C) STRANDEDNESS: single
          (D) TOPOLOGY: linear (iii) HYPOTHETICAL: NO (iv) ANTI-SENSE: NO (xi) SEQUENCE DESCRIPTION: SEQ ID NO:3:

Ser Leu Thr Ile Tyr Asn Leu Thr Ser Ser
1               5                   10

(2) INFORMATION FOR SEQ ID NO:4:

(i) SEQUENCE CHARACTERISTICS:
          (A) LENGTH: 20 amino acids
          (B) TYPE: amino acid
          (C) STRANDEDNESS: single
          (D) TOPOLOGY: linear (iii) HYPOTHETICAL: NO (iv) ANTI-SENSE: NO (xi) SEQUENCE DESCRIPTION: SEQ ID NO:4:

Thr Lys Pro Asp Leu Val Asp Lys Gly Thr Glu Asp Lys Val Val Asp
1               5                   10                  15

Val Val Arg Asn
            20

(2) INFORMATION FOR SEQ ID NO:5:

(i) SEQUENCE CHARACTERISTICS:
            (A) LENGTH: 77 amino acids
            (B) TYPE: amino acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:5:

Val Ala Gly Ser Asp Ala Gly Arg Ala Leu Gly Val Leu Ser Val Val
1               5                   10                  15

Cys Leu Leu His Cys Phe Gly Phe Ile Ser Cys Phe Ser Gln Gln Ile
                20                  25                  30

Tyr Gly Val Val Tyr Gly Asn Val Thr Phe His Val Pro Ser Asn Val
            35                  40                  45

Pro Leu Lys Glu Val Leu Trp Lys Lys Gln Lys Asp Lys Val Ala Glu
        50                  55                  60

Leu Glu Asn Ser Glu Phe Arg Ala Phe Ser Ser Phe Lys
65                  70                  75

(2) INFORMATION FOR SEQ ID NO:6:

(i) SEQUENCE CHARACTERISTICS:
            (A) LENGTH: 30 base pairs
            (B) TYPE: nucleic acid
            (C) STRANDEDNESS: double
            (D) TOPOLOGY: linear (iii) HYPOTHETICAL: NO (iv) ANTI-SENSE: NO (xi) SEQUENCE DESCRIPTION: SEQ ID NO:6:

AATAGGGTTT ATTTAGACAC TGTGTCAGGT                                           30

(2) INFORMATION FOR SEQ ID NO:7:

(i) SEQUENCE CHARACTERISTICS:
            (A) LENGTH: 16 amino acids
            (B) TYPE: amino acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:7:

Lys Asn Arg Val Tyr Leu Asp Thr Val Ser Gly Ser Leu Thr Ile Tyr
1               5                   10                  15

(2) INFORMATION FOR SEQ ID NO:8:

(i) SEQUENCE CHARACTERISTICS:

5,914,111

41

42

-continued (A) LENGTH: 30 base pairs
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:8:

TAATGGATTG CTAAGAAAGA ACTTCATGGT                                              30

(2) INFORMATION FOR SEQ ID NO:9:

(i) SEQUENCE CHARACTERISTICS:
            (A) LENGTH: 1040 base pairs
            (B) TYPE: nucleic acid
            (C) STRANDEDNESS: double
            (D) TOPOLOGY: linear (iii) HYPOTHETICAL: NO (iv) ANTI-SENSE: NO (ix) FEATURE:
            (A) NAME/KEY: CDS
            (B) LOCATION: 10..759

(xi) SEQUENCE DESCRIPTION: SEQ ID NO:9:

```
CGACGAGCC ATG GTT GCT GGG AGC GAC GCG GGG CGG GCC CTG GGG GTC          48
          Met Val Ala Gly Ser Asp Ala Gly Arg Ala Leu Gly Val
          1               5                   10

CTC AGC GTG GTC TGC CTG CTG CAC TGC TTT GGT TTC ATC AGC TGT TTT        96
Leu Ser Val Val Cys Leu Leu His Cys Phe Gly Phe Ile Ser Cys Phe
    15                  20                  25

TCC CAA CAA ATA TAT GGT GTT GTG TAT GGG AAT GTA ACT TTC CAT GTA       144
Ser Gln Gln Ile Tyr Gly Val Val Tyr Gly Asn Val Thr Phe His Val
30                  35                  40                  45

CCA AGC AAT GTG CCT TTA AAA GAG GTC CTA TGG AAA AAA CAA AAG GAT       192
Pro Ser Asn Val Pro Leu Lys Glu Val Leu Trp Lys Lys Gln Lys Asp
                50                  55                  60

AAA GTT GCA GAA CTG GAA AAT TCT GAA TTC AGA GCT TTC TCA TCT TTT       240
Lys Val Ala Glu Leu Glu Asn Ser Glu Phe Arg Ala Phe Ser Ser Phe
            65                  70                  75

AAA AAT AGG GTT TAT TTA GAC ACT GTG TCA GGT AGC CTC ACT ATC TAC       288
Lys Asn Arg Val Tyr Leu Asp Thr Val Ser Gly Ser Leu Thr Ile Tyr
        80                  85                  90

AAC TTA ACA TCA TCA GAT GAA GAT GAG TAT GAA ATG GAA TCG CCA AAT       336
Asn Leu Thr Ser Ser Asp Glu Asp Glu Tyr Glu Met Glu Ser Pro Asn
    95                  100                 105

ATT ACT GAT ACC ATG AAG TTC TTT CTT TAT GTG CTT GAG TCT CTT CCA       384
Ile Thr Asp Thr Met Lys Phe Phe Leu Tyr Val Leu Glu Ser Leu Pro
110                 115                 120                 125

TCT CCC ACA CTA ACT TGT GCA TTG ACT AAT GGA AGC ATT GAA GTC CAA       432
Ser Pro Thr Leu Thr Cys Ala Leu Thr Asn Gly Ser Ile Glu Val Gln
                130                 135                 140

TGC ATG ATA CCA GAG CAT TAC AAC AGC CAT CGA GGA CTT ATA ATG TAC       480
Cys Met Ile Pro Glu His Tyr Asn Ser His Arg Gly Leu Ile Met Tyr
            145                 150                 155

TCA TGG GAT TGT CCT ATG GAG CAA TGT AAA CGT AAC TCA ACC AGT ATA       528
Ser Trp Asp Cys Pro Met Glu Gln Cys Lys Arg Asn Ser Thr Ser Ile
        160                 165                 170

TAT TTT AAG ATG GAA AAT GAT CTT CCA CAA AAA ATA CAG TGT ACT CTT       576
Tyr Phe Lys Met Glu Asn Asp Leu Pro Gln Lys Ile Gln Cys Thr Leu
    175                 180                 185
```

```
AGC AAT CCA TTA TTT AAT ACA ACA TCA TCA ATC ATT TTG ACA ACC TGT      624
Ser Asn Pro Leu Phe Asn Thr Thr Ser Ser Ile Ile Leu Thr Thr Cys
190                 195                 200                 205

ATC CCA AGC AGC GGT CAT TCA AGA CAC AGA TAT GCA CTT ATA CCC ATA      672
Ile Pro Ser Ser Gly His Ser Arg His Arg Tyr Ala Leu Ile Pro Ile
                210                 215                 220

CCA TTA GCA GTA ATT ACA ACA TGT ATT GTG CTG TAT ATG AAT GGT ATT      720
Pro Leu Ala Val Ile Thr Thr Cys Ile Val Leu Tyr Met Asn Gly Ile
            225                 230                 235

CTG AAA TGT GAC AGA AAA CCA GAC AGA ACC AAC TCC AAT TGATTGGTAA       769
Leu Lys Cys Asp Arg Lys Pro Asp Arg Thr Asn Ser Asn
        240                 245                 250

CAGAAGATGA AGACAACAGC ATAACTAAAT TATTTTAAAA ACTAAAAAGC CATCTGATTT    829

CTCATTTGAG TATTACAATT TTTGAACAAC TGTTGGAAAT GTAACTTGAA GCAGCTGCTT    889

TAAGAAGAAA TACCCACTAA CAAAGAACAA GCATTAGTTT TGGCTGTCAT CAACTTATTA   949

TATGACTAGG TGCTTGCTTT TTTTGTCAGT AAATTGTTTT TACTGATGAT GTAGATACTT   1009

TTGTAAATAA ATGTAAATAT GTACACAAGT G                                  1040

(2) INFORMATION FOR SEQ ID NO:10:

(i) SEQUENCE CHARACTERISTICS:
        (A) LENGTH: 250 amino acids
        (B) TYPE: amino acid
        (D) TOPOLOGY: linear (ii) MOLECULE TYPE: protein (xi) SEQUENCE DESCRIPTION: SEQ ID NO:10:

Met Val Ala Gly Ser Asp Ala Gly Arg Ala Leu Gly Val Leu Ser Val
1               5                   10                  15

Val Cys Leu Leu His Cys Phe Gly Phe Ile Ser Cys Phe Ser Gln Gln
            20                  25                  30

Ile Tyr Gly Val Val Tyr Gly Asn Val Thr Phe His Val Pro Ser Asn
        35                  40                  45

Val Pro Leu Lys Glu Val Leu Trp Lys Gln Lys Asp Lys Val Ala
    50                  55                  60

Glu Leu Glu Asn Ser Glu Phe Arg Ala Phe Ser Ser Phe Lys Asn Arg
65                  70                  75                  80

Val Tyr Leu Asp Thr Val Ser Gly Ser Leu Thr Ile Tyr Asn Leu Thr
                85                  90                  95

Ser Ser Asp Glu Asp Glu Tyr Glu Met Glu Ser Pro Asn Ile Thr Asp
            100                 105                 110

Thr Met Lys Phe Phe Leu Tyr Val Leu Glu Ser Leu Pro Ser Pro Thr
        115                 120                 125

Leu Thr Cys Ala Leu Thr Asn Gly Ser Ile Glu Val Gln Cys Met Ile
130                 135                 140

Pro Glu His Tyr Asn Ser His Arg Gly Leu Ile Met Tyr Ser Trp Asp
145                 150                 155                 160

Cys Pro Met Glu Gln Cys Lys Arg Asn Ser Thr Ser Ile Tyr Phe Lys
                165                 170                 175

Met Glu Asn Asp Leu Pro Gln Lys Ile Gln Cys Thr Leu Ser Asn Pro
            180                 185                 190

Leu Phe Asn Thr Thr Ser Ser Ile Ile Leu Thr Thr Cys Ile Pro Ser
        195                 200                 205

Ser Gly His Ser Arg His Arg Tyr Ala Leu Ile Pro Ile Pro Leu Ala
210                 215                 220
```

```
Val Ile Thr Thr Cys Ile Val Leu Tyr Met Asn Gly Ile Leu Lys Cys
225                 230                 235                 240

Asp Arg Lys Pro Asp Arg Thr Asn Ser Asn
                245                 250

(2) INFORMATION FOR SEQ ID NO:11:

(i) SEQUENCE CHARACTERISTICS:
        (A) LENGTH: 863 base pairs
        (B) TYPE: nucleic acid
        (C) STRANDEDNESS: double
        (D) TOPOLOGY: linear (iii) HYPOTHETICAL: NO (iv) ANTI-SENSE: NO (ix) FEATURE:
        (A) NAME/KEY: CDS
        (B) LOCATION: 18..737

(xi) SEQUENCE DESCRIPTION: SEQ ID NO:11:

GCGGCCGCCG ACGAGCC ATG GTT GCT GGG AGC GAC GCG GGG CGG GCC CTG          50
                   Met Val Ala Gly Ser Asp Ala Gly Arg Ala Leu
                     1               5                  10

GGG GTC CTC AGC GTG GTC TGC CTG CTG CAC TGC TTT GGT TTC ATC AGC          98
Gly Val Leu Ser Val Val Cys Leu Leu His Cys Phe Gly Phe Ile Ser
             15                  20                  25

TGT TTT TCC CAA CAA ATA TAT GGT GTT GTG TAT GGG AAT GTA ACT TTC         146
Cys Phe Ser Gln Gln Ile Tyr Gly Val Val Tyr Gly Asn Val Thr Phe
         30                  35                  40

CAT GTA CCA AGC AAT GTG CCT TTA AAA GAG GTC CTA TGG AAA AAA CAA         194
His Val Pro Ser Asn Val Pro Leu Lys Glu Val Leu Trp Lys Lys Gln
     45                  50                  55

AAG GAT AAA GTT GCA GAA CTG GAA AAT TCT GAA TTC AGA GCT TTC TCA         242
Lys Asp Lys Val Ala Glu Leu Glu Asn Ser Glu Phe Arg Ala Phe Ser
 60                  65                  70                  75

TCT TTT AAA AAT AGG GTT TAT TTA GAC ACT GTG TCA GGT AGC CTC ACT         290
Ser Phe Lys Asn Arg Val Tyr Leu Asp Thr Val Ser Gly Ser Leu Thr
                 80                  85                  90

ATC TAC AAC TTA ACA TCA TCA GAT GAA GAT GAG TAT GAA ATG GAA TCG         338
Ile Tyr Asn Leu Thr Ser Ser Asp Glu Asp Glu Tyr Glu Met Glu Ser
             95                 100                 105

CCA AAT ATT ACT GAT ACC ATG AAG TTC TTT CTT TAT GTG CTT GAG TCT         386
Pro Asn Ile Thr Asp Thr Met Lys Phe Phe Leu Tyr Val Leu Glu Ser
         110                 115                 120

CTT CCA TCT CCC ACA CTA ACT TGT GCA TTG ACT AAT GGA AGC ATT GAA         434
Leu Pro Ser Pro Thr Leu Thr Cys Ala Leu Thr Asn Gly Ser Ile Glu
     125                 130                 135

GTC CAA TGC ATG ATA CCA GAG CAT TAC AAC AGC CAT CGA GGA CTT ATA         482
Val Gln Cys Met Ile Pro Glu His Tyr Asn Ser His Arg Gly Leu Ile
140                 145                 150                 155

ATG TAC TCA TGG GAT TGT CCT ATG GAG CAA TGT AAA CGT AAC TCA ACC         530
Met Tyr Ser Trp Asp Cys Pro Met Glu Gln Cys Lys Arg Asn Ser Thr
                160                 165                 170

AGT ATA TAT TTT AAG ATG GAA AAT GAT CTT CCA CAA AAA ATA CAG TGT         578
Ser Ile Tyr Phe Lys Met Glu Asn Asp Leu Pro Gln Lys Ile Gln Cys
            175                 180                 185

ACT CTT AGC AAT CCA TTA TTT AAT ACA ACA TCA TCA ATC ATT TTG ACA         626
Thr Leu Ser Asn Pro Leu Phe Asn Thr Thr Ser Ser Ile Ile Leu Thr
        190                 195                 200

ACC TGT ATC CCA AGC AGC GGT CAT TCA AGA CAC AGA TAT GCA CTT ATA         674
Thr Cys Ile Pro Ser Ser Gly His Ser Arg His Arg Tyr Ala Leu Ile
    205                 210                 215
```

```
CCC ATA CCA TTA GCA GTA ATT ACA ACA TGT ATT GTG CTG TAT ATG AAT        722
Pro Ile Pro Leu Ala Val Ile Thr Thr Cys Ile Val Leu Tyr Met Asn
220                 225                 230                 235

GGT ATG TAT GCT TTT TAAAACAAAA TAGTTTGAAA ACTTGCATTG TTTTCCAAAG         777
Gly Met Tyr Ala Phe
            240

GTCAGAAAAT AGTTTAAGGA TGAAATAAA GTTTGAAATT TTAGACATTT GAAAAAAAA        837

AAAAAAAAAA AAAAAAAGC GGCCGC                                             863
```

(2) INFORMATION FOR SEQ ID NO:12:

(i) SEQUENCE CHARACTERISTICS:
        (A) LENGTH: 240 amino acids
        (B) TYPE: amino acid
        (D) TOPOLOGY: linear (ii) MOLECULE TYPE: protein (xi) SEQUENCE DESCRIPTION: SEQ ID NO:12:

```
Met Val Ala Gly Ser Asp Ala Gly Arg Ala Leu Gly Val Leu Ser Val
 1               5                  10                  15

Val Cys Leu Leu His Cys Phe Gly Phe Ile Ser Cys Phe Ser Gln Gln
                20                  25                  30

Ile Tyr Gly Val Val Tyr Gly Asn Val Thr Phe His Val Pro Ser Asn
            35                  40                  45

Val Pro Leu Lys Glu Val Leu Trp Lys Lys Gln Lys Asp Lys Val Ala
        50                  55                  60

Glu Leu Glu Asn Ser Glu Phe Arg Ala Phe Ser Ser Phe Lys Asn Arg
65                  70                  75                  80

Val Tyr Leu Asp Thr Val Ser Gly Ser Leu Thr Ile Tyr Asn Leu Thr
                85                  90                  95

Ser Ser Asp Glu Asp Glu Tyr Glu Met Glu Ser Pro Asn Ile Thr Asp
            100                 105                 110

Thr Met Lys Phe Phe Leu Tyr Val Leu Glu Ser Leu Pro Ser Pro Thr
        115                 120                 125

Leu Thr Cys Ala Leu Thr Asn Gly Ser Ile Glu Val Gln Cys Met Ile
130                 135                 140

Pro Glu His Tyr Asn Ser His Arg Gly Leu Ile Met Tyr Ser Trp Asp
145                 150                 155                 160

Cys Pro Met Glu Gln Cys Lys Arg Asn Ser Thr Ser Ile Tyr Phe Lys
                165                 170                 175

Met Glu Asn Asp Leu Pro Gln Lys Ile Gln Cys Thr Leu Ser Asn Pro
            180                 185                 190

Leu Phe Asn Thr Thr Ser Ser Ile Ile Leu Thr Thr Cys Ile Pro Ser
        195                 200                 205

Ser Gly His Ser Arg His Arg Tyr Ala Leu Ile Pro Ile Pro Leu Ala
210                 215                 220

Val Ile Thr Thr Cys Ile Val Leu Tyr Met Asn Gly Met Tyr Ala Phe
225                 230                 235                 240
```

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:13:

CTCTTTTAAA GGCACATACA CAACACCATA                                    30

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:14:

AACTTTATCC TTTTGATTGC TTGGTACATG                                    30

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:15:

AGCTCTGAAT TCAGATTTTT TCCATAGGAC                                    30

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:16:

TAAATAAACC CTATTATTTT CCAGTTCTGC                                    30

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:17:

GTAGATAGTG AGGCTTTTAA AAGATGAGAA                                    30

(2) INFORMATION FOR SEQ ID NO:18:

(i) SEQUENCE CHARACTERISTICS:
        (A) LENGTH: 30 base pairs (B) TYPE: nucleic acid
              (C) STRANDEDNESS: single
              (D) TOPOLOGY: linear (iii) HYPOTHETICAL: NO (iv) ANTI-SENSE: NO (xi) SEQUENCE DESCRIPTION: SEQ ID NO:18:

ATACTCATCT TCATCACCTG ACACAGTGTC                                         30

(2) INFORMATION FOR SEQ ID NO:19:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (iii) HYPOTHETICAL: NO (iv) ANTI-SENSE: NO (xi) SEQUENCE DESCRIPTION: SEQ ID NO:19:

GGTATCAGTA ATATTTGATG ATGTTAAGTT                                         30

(2) INFORMATION FOR SEQ ID NO:20:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (iii) HYPOTHETICAL: NO (iv) ANTI-SENSE: NO (xi) SEQUENCE DESCRIPTION: SEQ ID NO:20:

AGACTCAAGC ACATATGGCG ATTCCATTTC                                         30

(2) INFORMATION FOR SEQ ID NO:21:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (iii) HYPOTHETICAL: NO (iv) ANTI-SENSE: NO (xi) SEQUENCE DESCRIPTION: SEQ ID NO:21:

CAATGCACAA GTTAGAAGAA AGAACTTCAT                                         30

(2) INFORMATION FOR SEQ ID NO:22:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (iii) HYPOTHETICAL: NO (iv) ANTI-SENSE: NO (xi) SEQUENCE DESCRIPTION: SEQ ID NO:22:

CATGCATTGG ACTTCTGTGG GAGATGGAAG                                         30

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:23:

TCCTCGATGG CTGTTAATGC TTCCATTAGT          30

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:24:

CATAGGACAA TCCCAGTAAT GCTCTGGTAT          30

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:25:

TATACTGGTT GAGTTTGAGT ACATTATAAG          30

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:26:

TTGTGGAAGA TCATTACGTT TACATTGCTC          30

(2) INFORMATION FOR SEQ ID NO:27:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:27:

TAATGGATTG CTAAGTTCCA TCTTAAAATA                                    30

(2) INFORMATION FOR SEQ ID NO:28:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:28:

TGTCAAAATG ATTGAAGTAC ACTGTATTTT                                    30

(2) INFORMATION FOR SEQ ID NO:29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:29:

TCTTGAATGA CCGCTTGATG TTGTATTAAA                                    30

(2) INFORMATION FOR SEQ ID NO:30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:30:

ATACTCATCT TCATCATACA CAACACCATA                                    30

(2) INFORMATION FOR SEQ ID NO:31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:31:

CATAGGACAA TCCCATGATG ATGTTAAGTT                                    30

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single

```
            (D) TOPOLOGY: linear (iii) HYPOTHETICAL: NO (iv) ANTI-SENSE: NO (xi) SEQUENCE DESCRIPTION: SEQ ID NO:32:

TCTTGAATGA CCGCTTGAGT ACATTATAAG                               30

(2) INFORMATION FOR SEQ ID NO:33:

(i) SEQUENCE CHARACTERISTICS:
            (A) LENGTH: 32 amino acids
            (B) TYPE: amino acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:33:

Ser Leu Thr Ile Tyr Asn Leu Thr Ser Ser Asp Glu Asp Glu Tyr Glu
 1               5                  10                  15

Met Glu Ser Pro Asn Ile Thr Asp Thr Met Lys Phe Phe Leu Tyr Val
                20                  25                  30

(2) INFORMATION FOR SEQ ID NO:34:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (iii) HYPOTHETICAL: NO (iv) ANTI-SENSE: NO (ix) FEATURE:
            (A) NAME/KEY: CDS
            (B) LOCATION: 6..23

(xi) SEQUENCE DESCRIPTION: SEQ ID NO:34:

TCGTC GAC AAA ACT CAC ACA TGC C                                24
      Asp Lys Thr His Thr Cys
       1               5

(2) INFORMATION FOR SEQ ID NO:35:

(i) SEQUENCE CHARACTERISTICS:
            (A) LENGTH: 6 amino acids
            (B) TYPE: amino acid
            (D) TOPOLOGY: linear (ii) MOLECULE TYPE: protein (xi) SEQUENCE DESCRIPTION: SEQ ID NO:35:

Asp Lys Thr His Thr Cys
 1               5

(2) INFORMATION FOR SEQ ID NO:36:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (iii) HYPOTHETICAL: NO
```

(iv) ANTI-SENSE: NO (xi) SEQUENCE DESCRIPTION: SEQ ID NO:36:

GTAAATGAGT GCGGCGGCCG CCAA                                                    24

(2) INFORMATION FOR SEQ ID NO:37:

(i) SEQUENCE CHARACTERISTICS:
            (A) LENGTH: 115 base pairs
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:37:

GCGGCCGCGG TCCAACCACC AATCTCAAAG CTTGGTACCC GGGAATTCAG ATCTGCAGCA      60

TGCTCGAGCT CTAGATATCG ATTCCATGGA TCCTCACATC CCAATCCGCG GCCGC          115

(2) INFORMATION FOR SEQ ID NO:38:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (iii) HYPOTHETICAL: NO (iv) ANTI-SENSE: NO (ix) FEATURE:
            (A) NAME/KEY: CDS
            (B) LOCATION: 13..33

(xi) SEQUENCE DESCRIPTION: SEQ ID NO:38:

GAGGCGGCCG CC ATG GTT GCT GGG AGC GAC GCG                                     33
              Met Val Ala Gly Ser Asp Ala
                1               5

(2) INFORMATION FOR SEQ ID NO:39:

(i) SEQUENCE CHARACTERISTICS:
            (A) LENGTH: 7 amino acids
            (B) TYPE: amino acid
            (D) TOPOLOGY: linear (ii) MOLECULE TYPE: protein (xi) SEQUENCE DESCRIPTION: SEQ ID NO:39:

Met Val Ala Gly Ser Asp Ala
 1               5

(2) INFORMATION FOR SEQ ID NO:40:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:40:

AAGTCGACAT AAAGAAAGAA CTTCAT                                                  26

(2) INFORMATION FOR SEQ ID NO:41:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:41:

TCGACGCGGC CGCG                                                  14

(2) INFORMATION FOR SEQ ID NO:42:

(i) SEQUENCE CHARACTERISTICS:
        (A) LENGTH: 1050 base pairs
        (B) TYPE: nucleic acid
        (C) STRANDEDNESS: single
        (D) TOPOLOGY: linear (iii) HYPOTHETICAL: NO (iv) ANTI-SENSE: NO (ix) FEATURE:
        (A) NAME/KEY: CDS
        (B) LOCATION: 1..1041

(xi) SEQUENCE DESCRIPTION: SEQ ID NO:42:

```
ATG GTT GCT GGG AGC GAC GCG GGG CGG GCC CTG GGG GTC CTC AGC GTG        48
Met Val Ala Gly Ser Asp Ala Gly Arg Ala Leu Gly Val Leu Ser Val
 1               5                  10                  15

GTC TGC CTG CTG CAC TGC TTT GGT TTC ATC AGC TGT TTT TCC CAA CAA        96
Val Cys Leu Leu His Cys Phe Gly Phe Ile Ser Cys Phe Ser Gln Gln
                20                  25                  30

ATA TAT GGT GTT GTG TAT GGG AAT GTA ACT TTC CAT GTA CCA AGC AAT       144
Ile Tyr Gly Val Val Tyr Gly Asn Val Thr Phe His Val Pro Ser Asn
            35                  40                  45

GTG CCT TTA AAA GAG GTC CTA TGG AAA AAA CAA AAG GAT AAA GTT GCA       192
Val Pro Leu Lys Glu Val Leu Trp Lys Lys Gln Lys Asp Lys Val Ala
        50                  55                  60

GAA CTG GAA AAT TCT GAA TTC AGA GCT TTC TCA TCT TTT AAA AAT AGG       240
Glu Leu Glu Asn Ser Glu Phe Arg Ala Phe Ser Ser Phe Lys Asn Arg
 65                  70                  75                  80

GTT TAT TTA GAC ACT GTG TCA GGT AGC CTC ACT ATC TAC AAC TTA ACA       288
Val Tyr Leu Asp Thr Val Ser Gly Ser Leu Thr Ile Tyr Asn Leu Thr
                85                  90                  95

TCA TCA GAT GAA GAT GAG TAT GAA ATG GAA TCG CCA AAT ATT ACT GAT       336
Ser Ser Asp Glu Asp Glu Tyr Glu Met Glu Ser Pro Asn Ile Thr Asp
               100                 105                 110

ACC ATG AAG TTC TTT CTT TAT GTC GAC AAA ACT CAC ACA TGC CCA CCG       384
Thr Met Lys Phe Phe Leu Tyr Val Asp Lys Thr His Thr Cys Pro Pro
           115                 120                 125

TGC CCA GCA CCT GAA CTC CTG GGG GGA CCG TCA GTC TTC CTC TTC CCC       432
Cys Pro Ala Pro Glu Leu Leu Gly Gly Pro Ser Val Phe Leu Phe Pro
       130                 135                 140

CCA AAA CCC AAG GAC ACC CTC ATG ATC TCC CGG ACC CCT GAG GTC ACA       480
Pro Lys Pro Lys Asp Thr Leu Met Ile Ser Arg Thr Pro Glu Val Thr
145                 150                 155                 160

TGC GTG GTG GTG GAC GTG AGC CAC GAA GAC CCT GAG GTC AAG TTC AAC       528
Cys Val Val Val Asp Val Ser His Glu Asp Pro Glu Val Lys Phe Asn
                165                 170                 175
```

```
TGG TAC GTG GAC GGC GTG GAG GTG CAT AAT GCC AAG ACA AAG CCG CGG         576
Trp Tyr Val Asp Gly Val Glu Val His Asn Ala Lys Thr Lys Pro Arg
            180                 185                 190

GAG GAG CAG TAC AAC AGC ACG TAC CGG GTG GTC AGC GTC CTC ACC GTC         624
Glu Glu Gln Tyr Asn Ser Thr Tyr Arg Val Val Ser Val Leu Thr Val
        195                 200                 205

CTG CAC CAG GAC TGG CTG AAT GGC AAG GAG TAC AAG TGC AAG GTC TCC         672
Leu His Gln Asp Trp Leu Asn Gly Lys Glu Tyr Lys Cys Lys Val Ser
    210                 215                 220

AAC AAA GCC CTC CCA GCC CCC ATC GAG AAA ACC ATC TCC AAA GCC AAA         720
Asn Lys Ala Leu Pro Ala Pro Ile Glu Lys Thr Ile Ser Lys Ala Lys
225                 230                 235                 240

GGG CAG CCC CGA GAA CCA CAG GTG TAC ACC CTG CCC CCA TCC CGG GAT         768
Gly Gln Pro Arg Glu Pro Gln Val Tyr Thr Leu Pro Pro Ser Arg Asp
                245                 250                 255

GAG CTG ACC AAG AAC CAG GTC AGC CTG ACC TGC CTG GTC AAA GGC TTC         816
Glu Leu Thr Lys Asn Gln Val Ser Leu Thr Cys Leu Val Lys Gly Phe
            260                 265                 270

TAT CCC AGC GAC ATC GCC GTG GAG TGG GAG AGC AAT GGG CAG CCG GAG         864
Tyr Pro Ser Asp Ile Ala Val Glu Trp Glu Ser Asn Gly Gln Pro Glu
        275                 280                 285

AAC AAC TAC AAG ACC ACG CCT CCC GTG CTG GAC TCC GAC GGC TCC TTC         912
Asn Asn Tyr Lys Thr Thr Pro Pro Val Leu Asp Ser Asp Gly Ser Phe
    290                 295                 300

TTC CTC TAC AGC AAG CTC ACC GTG GAC AAG AGC AGG TGG CAG CAG GGG         960
Phe Leu Tyr Ser Lys Leu Thr Val Asp Lys Ser Arg Trp Gln Gln Gly
305                 310                 315                 320

AAC GTC TTC TCA TGC TCC GTG ATG CAT GAG GCT CTG CAC AAC CAC TAC        1008
Asn Val Phe Ser Cys Ser Val Met His Glu Ala Leu His Asn His Tyr
                325                 330                 335

ACG CAG AAG AGC CTC TCC CTG TCT CCG GGT AAA TGAGTGCGG                  1050
Thr Gln Lys Ser Leu Ser Leu Ser Pro Gly Lys
            340                 345
```

(2) INFORMATION FOR SEQ ID NO:43:

(i) SEQUENCE CHARACTERISTICS:
        (A) LENGTH: 347 amino acids
        (B) TYPE: amino acid
        (D) TOPOLOGY: linear (ii) MOLECULE TYPE: protein (xi) SEQUENCE DESCRIPTION: SEQ ID NO:43:

```
Met Val Ala Gly Ser Asp Ala Gly Arg Ala Leu Gly Val Leu Ser Val
 1               5                  10                  15

Val Cys Leu Leu His Cys Phe Gly Phe Ile Ser Cys Phe Ser Gln Gln
                20                  25                  30

Ile Tyr Gly Val Val Tyr Gly Asn Val Thr Phe His Val Pro Ser Asn
            35                  40                  45

Val Pro Leu Lys Glu Val Leu Trp Lys Lys Gln Lys Asp Lys Val Ala
        50                  55                  60

Glu Leu Glu Asn Ser Glu Phe Arg Ala Phe Ser Ser Phe Lys Asn Arg
65                  70                  75                  80

Val Tyr Leu Asp Thr Val Ser Gly Ser Leu Thr Ile Tyr Asn Leu Thr
                85                  90                  95

Ser Ser Asp Glu Asp Glu Tyr Glu Met Glu Ser Pro Asn Ile Thr Asp
            100                 105                 110

Thr Met Lys Phe Phe Leu Tyr Val Asp Lys Thr His Thr Cys Pro Pro
        115                 120                 125
```

```
Cys Pro Ala Pro Glu Leu Leu Gly Gly Pro Ser Val Phe Leu Phe Pro
    130             135             140

Pro Lys Pro Lys Asp Thr Leu Met Ile Ser Arg Thr Pro Glu Val Thr
145             150             155             160

Cys Val Val Val Asp Val Ser His Glu Asp Pro Glu Val Lys Phe Asn
            165             170             175

Trp Tyr Val Asp Gly Val Glu Val His Asn Ala Lys Thr Lys Pro Arg
        180             185             190

Glu Glu Gln Tyr Asn Ser Thr Tyr Arg Val Val Ser Val Leu Thr Val
    195             200             205

Leu His Gln Asp Trp Leu Asn Gly Lys Glu Tyr Lys Cys Lys Val Ser
    210             215             220

Asn Lys Ala Leu Pro Ala Pro Ile Glu Lys Thr Ile Ser Lys Ala Lys
225             230             235             240

Gly Gln Pro Arg Glu Pro Gln Val Tyr Thr Leu Pro Pro Ser Arg Asp
            245             250             255

Glu Leu Thr Lys Asn Gln Val Ser Leu Thr Cys Leu Val Lys Gly Phe
            260             265             270

Tyr Pro Ser Asp Ile Ala Val Glu Trp Glu Ser Asn Gly Gln Pro Glu
        275             280             285

Asn Asn Tyr Lys Thr Thr Pro Pro Val Leu Asp Ser Asp Gly Ser Phe
    290             295             300

Phe Leu Tyr Ser Lys Leu Thr Val Asp Lys Ser Arg Trp Gln Gln Gly
305             310             315             320

Asn Val Phe Ser Cys Ser Val Met His Glu Ala Leu His Asn His Tyr
            325             330             335

Thr Gln Lys Ser Leu Ser Leu Ser Pro Gly Lys
            340             345
```

CD2-BINDING DOMAIN OF LYMPHOCYTE FUNCTION ASSOCIATED ANTIGEN-3

This is a division of application Ser. No. 07/940,861, filed Oct. 21, 1992, U.S. Pat. No. 5,547,853, which is a continuation-in-part of abandoned application Ser. No. 07/770,967, filed Oct. 7, 1991, which is a continuation-in-part of abandoned application Ser. No. 07/667,971, filed Mar. 12, 1991, filed as application No. PCT/US92/02050, Mar. 12, 1991, abandoned.

This invention relates to DNA sequences encoding and polypeptides which comprise the CD2-binding domain of Lymphocyte Function Associated Antigen 3 ("LFA-3") and to recombinant DNA molecules for expression of those polypeptides. In accordance with this invention, unicellular hosts transformed with the DNA sequences and recombinant DNA molecules containing these DNA sequences may be prepared and used to produce proteins and polypeptides comprising the CD2-binding domain of LFA-3. The peptides, polypeptides and proteins of this invention are useful in the study of interactions between CD2 and LFA-3, in diagnostic and therapeutic compositions, in antibody screening or purification methods and in other methods of this invention.

BACKGROUND OF THE INVENTION

T-lymphocytes play a major role in the immune response by interacting with target and antigen presenting cells. T-lymphocyte-mediated killing of target cells is a multi-step process involving adhesion of cytolytic T-lymphocytes to target cells. The initiation of the immune response to most antigens involves adhesion of helper T-lymphocytes to antigen-presenting cells.

These interactions of T-lymphocytes with target and antigen-presenting cells are highly specific and depend on the recognition of an antigen on the target or antigen-presenting cell by one of the many specific antigen receptors on the surface of T-lymphocytes.

The receptor-antigen interaction of T-lymphocytes and other cells is facilitated by various T-lymphocyte surface proteins, e.g., the antigen-receptor complex CD3 and accessory molecules CD4, LFA-1, CD8 and CD2. The interaction of T-lymphocytes and other cells is also dependent on accessory molecules, such as ICAM-1, MHC class I and II and LFA-3, that are expressed on the surface of target or antigen-presenting cells and thereby play a role in the action of T-lymphocytes. One general hypothesis is that accessory molecules on the T-lymphocytes and on the target or antigen-presenting cells interact with each other to mediate intercellular adhesion. Accordingly, these accessory molecules are believed to enhance the efficiency of lymphocyte/antigen-presenting cell and lymphocyte/target cell interactions and to be important in cell adhesion-based pathologies (such as leukocyte/endothelial cell interaction leading to pathologic inflammation) and lymphocyte recirculation. Accessory molecules are also involved in activation of lymphocytes.

One important example of cell-cell interaction mediated by accessory molecules is the specific interaction between CD2 (a T-lymphocyte accessory molecule) and LFA-3 (a target cell accessory molecule). CD2/LFA-3 binding appears to be essential for many important cell-cell reactions, including the initiation of the T-lymphocyte functional responses (Dustin et al., *J. Exp. Med.*, 165, pp. 677–92 (1987); Springer et al., *Ann. Rev. Immunol.*, 5, pp. 223–52 (1987)). The importance of the CD2/LFA-3 complex in cell-cell adhesion is indicated by the findings that purified LFA-3 binds to CD2 on the surface of T-lymphocytes (Dustin et al., *J. Exp. Med.*, 165, pp. 677–92 (1987)), that CD2 purified from T-lymphocytes binds LFA-3 on cell surfaces and inhibits the binding of LFA-3-specific monoclonal antibodies ("MAbs") to LFA-3 (Selvaraj et al., *Nature,* 326, pp. 400–403 (1987)), and that rosetting of human erythrocytes, which express LFA-3, to cells expressing CD2 is blocked by anti-LFA-3 MAbs and anti-CD2 MAbs (see, e.g., Seed et al., *Proc. Natl. Acad. Sci. USA,* 84, pp. 3365–69 (1987)).

LFA-3, which is found on the surface of a wide variety of cells including monocytes, granulocytes, T-lymphocytes, erythrocytes, B-lymphoblastoid cell lines, thymic epithelial cells, and vascular endothelial cells, has become the subject of a considerable amount of study to further elucidate its role in various T-lymphocyte interactions. Two natural forms of LFA-3 have been identified. One form of LFA-3 ("transmembrane LFA-3") is anchored in the cell membrane by a transmembrane hydrophobic domain. cDNA encoding this form of LFA-3 has been cloned and sequenced (see, e.g., Wallner et al., *J. Exp. Med.,* 166, pp. 923–32 (1987)). Another form of LFA-3 is anchored to the cell membrane via a covalent linkage to phosphatidylinositol ("PI") -containing glycolipid. This latter form has been designated "PI-linked LFA-3", and cDNA encoding this form of LFA-3 has also been cloned and sequenced (Wallner et al., PCT patent application WO 90/02181).

Although the DNA sequence of the LFA-3 gene and the primary amino acid sequences of both forms of LFA-3 have been determined, the actual site of interaction between LFA-3 and its receptor, CD2, has not previously been identified. There is a need to identify the CD2-binding domain on LFA-3 in order to better understand the specific interaction between CD2 and LFA-3 and, thereby, to effect and modulate the cellular and immunological processes that are dependent on the formation of the CD2/LFA-3 complex. Such information would also be useful in a variety of other applications including diagnostic and therapeutic compositions, protein purification, antibody identification and purification, and comparative and structural studies of LFA-3 and other proteins.

SUMMARY OF THE INVENTION

This invention addresses the aforementioned needs by identifying the CD2-binding domain of LFA-3 and providing nucleotide sequences defining the CD2-binding region of LFA-3 and CD2 binding polypeptides encoded by those sequences. The present invention provides polypeptides having the amino acid sequence: $X_1-X_2$-(SEQ ID NO:1) Asn Arg Val Tyr Leu Asp Thr Val Ser Gly-Y, wherein:

$X_1$ is hydrogen or methionyl;

$X_2$, if present, is a polypeptide having the following amino acid sequence or a portion thereof consisting of the carboxy terminal 1 to 77 amino acids of the sequence (SEQ ID NO:5): Val Ala Gly Ser Asp Ala Gly Arg Ala Leu Gly Val Leu Ser Val Val Cys Leu Leu His Cys Phe Gly Phe Ile Ser Cys Phe Ser Gln Gln Ile Tyr Gly Val Val Tyr Gly Asn Val Thr Phe His Val Pro Ser Asn Val Pro Leu Lys Glu Val Leu Trp Lys Lys Gln Lys Asp Lys Val Ala Glu Leu Glu Asn Ser Glu Phe Arg Ala Phe Ser Ser Phe Lys;

Y is hydroxyl or a polypeptide of the following amino acid sequence or a portion thereof consisting of the amino-terminal 1 to 32 amino acids of the sequence (SEQ ID NO:33): Ser Leu Thr Ile Tyr Asn Leu Thr Ser Ser Asp Glu Asp Glu Tyr Glu Met Glu Ser Pro Asn Ile Thr Asp Thr Met Lys Phe Phe Leu Tyr Val;

and analogs and derivatives thereof, said polypeptides being capable of binding to CD2.

In another embodiment, the present invention provides polypeptides having the amino acid sequence: $X_1$–$X_2$-(SEQ ID NO:1) Asn Arg Val Tyr Leu Asp Thr Val Ser Gly-Y, wherein:

$X_1$ is hydrogen or methionyl;

$X_2$, if present, is a polypeptide having the following amino acid sequence or a portion thereof consisting of the carboxy-terminal 1 to 50 amino acids of the sequence (SEQ ID NO:2): Phe Ser Gln Gln Ile Tyr Gly Val Val Tyr Gly Asn Val Thr Phe His Val Pro Ser Asn Val Pro Leu Lys Glu Val Leu Trp Lys Lys Gln Lys Asp Lys Val Ala Glu Leu Glu Asn Ser Glu Phe Arg Ala Phe Ser Ser Phe Lys;

Y is hydroxyl or a polypeptide of the following amino acid sequence or a portion thereof consisting of the amino-terminal 1 to 10 amino acids of the sequence (SEQ ID NO:3): Ser Leu Thr Ile Tyr Asn Leu Thr Ser Ser;

and analogs and derivatives thereof, said polypeptides being capable of binding to CD2.

The invention also provides DNA sequences encoding the above polypeptides, recombinant molecules containing those DNA sequences, hosts transfected with such DNA sequences and molecules and methods of making the polypeptides recombinantly, synthetically or semi-synthetically.

The polypeptides of this invention are useful in diagnosing diseases characterized by the presence or absence of CD2 on the surface of particular cells and to treat pathologies dependent on the formation of the LFA-3/CD2 complex.

The polypeptides of this invention and the DNA sequences encoding them may also be used to prepare recombinant or synthetic fusion proteins, which comprise a functional CD2-binding domain or polypeptide of LFA-3, as defined above, and another domain of a protein or polypeptide other than LFA-3. The CD2-binding domain portion of the fusion proteins allows the other polypeptides to be targeted specifically to CD2-expressing cells (CD2$^+$ cells). DNA sequences encoding these fusion proteins are also part of this invention.

One example of such fusion proteins of this invention is novel fusion proteins containing a portion of LFA-3 containing a functional CD2-binding domain, as defined above, fused to at least a portion of the Fc region of an immunoglobulin (Ig). Unexpectedly, the LFA-3-Ig fusion proteins of this invention inhibit T-lymphocyte activation and proliferation of peripheral blood lymphocytes.

It is a further aspect of this invention that the polypeptides and fusion proteins of this invention may also be used to label CD2 molecules, for example, soluble CD2, in solution or on the surface of T-lymphocytes or other CD2-expressing cells. The polypeptides and fusion proteins of this invention may also be used to label any protein, polypeptide or peptide comprising the domain of CD2 which binds LFA-3, for example, in a fusion protein generated using recombinant DNA techniques.

The polypeptides and fusion proteins of this invention may also be used in affinity chromatography to purify CD2 or any other polypeptide or protein conjugate containing the domain of CD2 which binds LFA-3.

This invention also provides altered (mutant) forms of the LFA-3 protein which lack the CD2-binding domain and the DNA sequences encoding such "deletion mutant" forms of LFA-3. Mutant proteins, which lack the CD2-binding domain of LFA-3, as defined above, may be used in vivo or in vitro to generate or to bind antibodies or other molecules that recognize epitopes or sites on LFA-3 other than the CD2-binding domain.

In addition to the monomeric form of the CD2-binding polypeptides and fusion proteins of this invention, multimeric forms are also enabled by this invention. Such forms may have enhanced affinity for CD2, enhanced immunogenicity and/or enhanced ability to initiate T-lymphocyte functional responses, e.g., stimulation of T-cell activation, through more effective or multiplied formation of CD2/LFA-3 complexes. Also, such multimeric forms may be more effective in competitive binding of CD2, making them more useful as immunosuppressants and more sensitive as diagnostics or reagents.

In addition, this invention contemplates antibodies recognizing the polypeptides and fusion proteins of this invention. Polyclonal and monoclonal antibodies to the polypeptides and fusion proteins of this invention may be obtained by immunizing an animal with polypeptides or fusion proteins of this invention.

Low molecular weight (generally less than 1000 daltons) inhibitors of the formation of the CD2/LFA-3 complex are also provided by this invention. Such "small molecule" inhibitors may be produced in vitro by synthetic methods and may comprise part of the amino acid sequences of the polypeptides of this invention or may be entirely non-peptidyl organic molecules having a structural conformation that is able to mimic the binding specificity of the polypeptides and fusion proteins of this invention to CD2.

This invention also provides methods, compositions and kits for diagnostic and therapeutic uses in which the presence or absence of the CD2-binding domain of LFA-3 is desirable.

BRIEF DESCRIPTION OF THE DRAWINGS

FIGS. 1A-1, 1A-2 and FIG. 1B taken together depict amino acid (SEQ ID NO:10) and nucleotide (SEQ ID NO:9) sequences of transmembrane LFA-3 indicating (with underlining) deletions made in the extracellular region of LFA-3. Regions designated M53, M54, M55, M56, M57, M58, M59, M60, M61, M62, M63, M64, M65, M66, M90, M91 and M92, respectively, were looped out to create recombinant genes encoding 17 separate deletion mutants. Expression of the deletion mutants in mammalian cells provided altered LFA-3 surface proteins missing a segment of amino acids present in the native LFA-3 protein. For example, expression of the deletion mutant designated M57 (that is, the LFA-3 DNA of FIGS. 1A-1 and 1A-2 having the M57 region deleted) in CHO cells resulted in a mutant LFA-3 that did not bind to CD2. The amino terminal methionine (Met) is designated –28 to indicate that it is the amino terminal residue of the 28-amino acid signal peptide sequence of preLFA-3. The amino terminal residue of mature LFA-3 is a phenylalanine (Phe) and is designated +1.

FIG. 5 shows an autoradiogram depicting the differential immunoprecipitation of proteins from $^{125}$I surface-labeled M57/CHO cells (lanes 1–4), normal CHO cells (negative control)(lanes 5–7), and P24/CHO cells (positive control) (lanes 8–11). Lysates of surface-labeled cells were reacted with anti-LFA-3 MAb TS2/9 (lanes 2, 5, 9), anti-LFA-3 MAb 7A6 (lanes 3, 6, 10), or anti-LFA-3 polyclonal antiserum 202 (lanes 4, 7, 11). The antibody-precipitated proteins were electrophoresed on SDS-polyacrylamide gels prior to autoradiography.

FIGS. 6A-1, 6A-2 and 6B taken together) depict amino acid (SEQ ID NO:10) and nucleotide (SEQ ID NO:9) sequences of transmembrane LFA-3 indicating (with underlining) deletions in the extracellular region of LFA-3. Regions designated M100, M101, and M102, respectively, were looped out to create recombinant genes encoding 3 separate deletion mutants.

FIGS. 9A and 9B depict the amino acid (SEQ ID NO:12) and nucleotide (SEQ ID NO:11) sequences of PI-linked LFA-3 indicating (with underlining) the internal deletion made in the nucleotide sequence and corresponding mutant PI-linked LFA-3 protein. The region of the DNA designated PIM3 was looped out to create a recombinant gene encoding a mutant protein containing the N-terminal 89 amino acids of PI-linked LFA-3 but lacking the subsequent 71 amino acids. Expression of the deletion mutant PIM3 (that is, the PI-linked LFA-3 DNA of FIGS. 9A and 9B having the PIM3 region deleted) in CHO cells resulted in a mutant form of PI-linked LFA-3 that retained a CD2-binding domain.

FIG. 10B depicts the results of a similar analysis using transfected CHO cells amplified for expression of the mutant PI-linked protein (PIM2.25.2.100.12 cells). These cells produced a protein on their cell surface recognized by MAb 7A6 (FIG. 10B, dashed line) and that was susceptible to release from the cell surface by PI-PLC treatment (FIG. 10B, dotted line). In each analysis, the control peak (solid line) represents the cell population with background levels of FITC-conjugated goat anti-mouse IgG binding.

FIGS. 12A and 12B depict the amino acid (SEQ ID NO:43) and nucleotide (SEQ ID NO:42) sequences of preLFA3TIP (i.e., LFA-3 (amino acids +1–+92) and the 28-amino acid signal sequence) and the various domains of the fusion protein. The nucleotide sequence of FIGS. 12A and 12B is also the same as the DNA sequence insert in the expression plasmid pSAB152.

FIG. 13 is a photograph of a Western blot analysis of SDS-PAGE gels under nonreducing (lanes 1 and 2) and reducing (lanes 3 and 4) conditions. Lanes 1 and 3 are high molecular weight markers (BRL, Gaithersburg, Md.). Lanes 2 and 4 contain LFA3TIP purified as described in Example 13.

DETAILED DESCRIPTION OF THE INVENTION

Figure 2A:
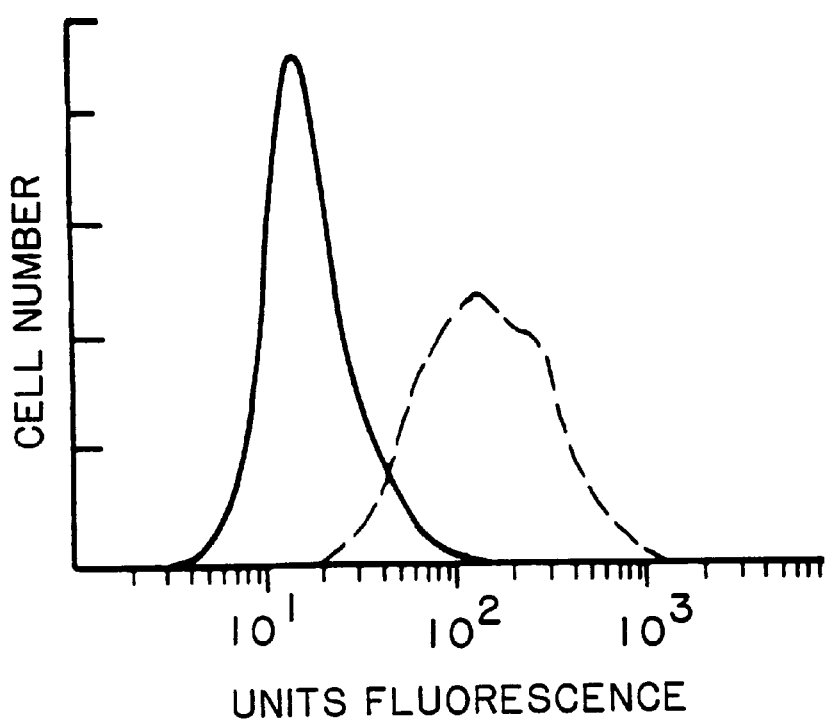
FIGS. 2A, 2B, 2C, 2D, 2E, 2F, 2G, 2H, 2I, 2J, 2K, 2L, 2M and 2N taken together depict results of immunofluorescence flow cytometry by FACS analysis of transfected CHO cells expressing mutant forms of LFA-3 encoded by deletion mutants M57 (FIGS. 2A and 2B), M65 (FIGS. 2C and 2D), M63 (FIGS. 2E and 2F), M54 (FIGS. 2G and 2H), M55 (FIGS. 2I and 2J), M56 (FIGS. 2K and 2L), and M58 (FIGS. 2M and 2N). Transfected cells were reacted with anti-LFA-3 polyclonal antiserum 202 (dashed lines, FIGS. 2A, 2C, 2E, 2G, 2I, 2K, 2M), anti-LFA-3 MAb TS2/9 (dashed lines, FIGS. 2B, 2D, 2F, 2H, 2J, 2L, 2N), or anti-LFA-3 MAb 7A6 (dotted lines, FIGS. 2B, 2D, 2F, 2H, 2J, 2L, 2N). In each analysis, the control peak (solid line) represents the cell population with background levels of fluorescein isothiocyanate-conjugated (FITC) goat anti-mouse or goat anti-rabbit IgG binding.

The polypeptides, compositions, and methods of the present invention are characterized by polypeptides having the amino acid sequence: $X_1-X_2$-(SEQ ID NO:1)
Asn Arg Val Tyr Leu Asp Thr Val Ser Gly-Y, wherein:

$X_1$ is hydrogen or methionyl;

$X_2$, if present, is a polypeptide having the following amino acid sequence or a portion thereof consisting of the carboxy-terminal 1 to 77 amino acids of the sequence (SEQ ID NO:5): Val Ala Gly Ser Asp Ala Gly Arg Ala Leu Gly Val Leu Ser Val Val Cys Leu Leu His Cys Phe Gly Phe Ile Ser Cys Phe Ser Gln Gln Ile Tyr Gly Val Val Tyr Gly Asn Val Thr Phe His Val Pro Ser Asn Val Pro Leu Lys Glu Val Leu Trp Lys Lys Gln Lys Asp Lys Val Ala Glu Leu Glu Asn Ser Glu Phe Arg Ala Phe Ser Ser Phe Lys;

Y is hydroxyl or a polypeptide of the following amino acid sequence or a portion thereof consisting of the amino-terminal 1 to 32 amino acids of the sequence (SEQ ID NO:33): Ser Leu Thr Ile Tyr Asn Leu Thr Ser Ser Asp Glu Asp Glu Tyr Glu Met Glu Ser Pro Asn Ile Thr Asp Thr Met Lys Phe Phe Leu Tyr Val;

and analogs and derivatives thereof, said polypeptides being capable of binding to CD2.

In another embodiment, the polypeptides of this invention have the amino acid sequence: $X_1-X_2$-(SEQ ID NO:1) Asn Arg Val Tyr Leu Asp Thr Val Ser Gly-Y, wherein:

$X_1$ is hydrogen or methionyl;

$X_2$, if present, is a polypeptide having the following amino acid sequence or a portion thereof consisting of the carboxy-terminal 1 to 50 amino acids of the sequence (SEQ ID NO:2): Phe Ser Gln Gln Ile Tyr Gly Val Val Tyr Gly Asn Val Thr Phe His Val Pro Ser Asn Val Pro Leu Lys Glu Val Leu Trp Lys Lys Gln Lys Asp Lys Val Ala Glu Leu Glu Asn Ser Glu Phe Arg Ala Phe Ser Ser Phe Lys;

Y is hydroxyl or a polypeptide of the following amino acid sequence or a portion thereof consisting of the amino-terminal 1 to 10 amino acids of the sequence (SEQ ID NO:3): Ser Leu Thr Ile Tyr Asn Leu Thr Ser Ser;

and analogs and derivatives thereof, said polypeptides being capable of binding to CD2.

Preferably, the polypeptides of this invention have the amino acid sequence of amino acids 29–120 of SEQ ID NO:10, amino acids 29–108 of SEQ ID NO:10, amino acids 48–108 of SEQ ID NO:10, and SEQ ID NO:7.

Throughout this specification and in the claims, the abbreviations employed for amino acids and their residues are used in conformity with the generally accepted rules of nomenclature and relate to α-amino acids and their residues of the L-series.

A derivatized amino acid is a natural or non-natural amino acid in which the normally occurring side chain or end group is modified by chemical reaction. Such modifications include, for example, gamma-carboxylation, β-hydroxylation, sulfation, sulfonation, phosphorylation, amidization, esterification, t-butoxy carbonylation, N-acetylation, carbobenzoxylation, tosylation, benzylation, and other modifications known in the art.

A derivatized polypeptide is a polypeptide containing one or more derivatized amino acids.

Analogs of the polypeptides of this invention may be characterized, for example, by amino acid substitutions, additions or deletions, or utilization of D-amino acids. The preferred substitutions in the polypeptides of this invention are those that are recognized in the art to be conservative amino acid substitutions. For example, amino acids belonging to one of the following groups represent conservative changes: ala, pro, gly, glu, asp, gln, asn, ser, thr; cys, ser, tyr, thr; val, ile, leu, met, ala, phe; lys, arg, his; and phe, tyr, trp, his. See, e.g., Grantham, *Science*, 185, pp. 862–64 (1974); Dayhoff, In *Atlas of Protein Sequence and Structure*, 5, 1978; Argos, *EMBO J.*, 8, pp. 779–785 (1989).

It should be understood that all analogues and derivatives of this invention are characterized by biological activities that are similar to those of the CD2-binding polypeptides described herein. Accordingly, these analogs and derivatives may be employed in compositions, combinations and methods for diagnosis, therapy and prophylaxis in the same manner as the polypeptides of this invention.

The production of the polypeptides of this invention may be achieved by a variety of methods known in the art. For example, the polypeptides may be derived from the intact transmembrane or PI-linked LFA-3 molecules by proteolysis using specific endopeptidases in combination with exopeptidases, Edman degradation, or both. The intact LFA-3 molecules, in turn, may be purified from natural sources using conventional methods. Alternatively, full-length LFA-3 or truncated forms of LFA-3 may be produced by known recombinant DNA techniques using cDNAs. (See, U.S. Pat. No. 4,956,281 to Wallner et al.)

Preferably, the polypeptides of the present invention are produced directly, thus eliminating the need for a larger LFA-3 as a starting material. This may be achieved by conventional chemical peptide synthesis techniques or by well-known recombinant DNA techniques, wherein only those DNA sequences which encode the desired polypeptides are expressed in transformed hosts.

A gene which encodes the desired LFA-3 polypeptide of this invention may be designed based on the amino acid sequence of the desired polypeptide. Standard methods may be then applied to synthesize the gene. For example, the amino acid sequence may be used to construct a back-translated gene. A DNA oligomer containing a nucleotide sequence capable of coding for an LFA-3 polypeptide of this invention may be synthesized in a single step. Alternatively, several smaller oligonucleotides coding for portions of the desired polypeptide may be synthesized and then ligated together. Preferably, the DNA sequence encoding an LFA-3 polypeptide of this invention will be synthesized as several separate oligonucleotides which are subsequently linked together. The individual oligonucleotides typically contain 5' or 3' overhangs for complementary assembly.

Once assembled, preferred genes will be characterized by sequences that are recognized by restriction endonucleases (including unique restriction sites for direct assembly into a cloning or an expression vector), preferred codons taking into consideration the host expression system to be used, and a sequence which, when transcribed, produces a stable, efficiently translated RNA. Proper assembly may be confirmed by nucleotide sequencing, restriction mapping, and expression of a biologically active polypeptide in a suitable host.

One embodiment of a DNA sequence according to this invention comprises the nucleic acid sequence encoding amino acids 1 through 70 of mature LFA-3, i.e., nucleotides 94 through 303 in FIG. 1. Another preferred embodiment comprises the nucleic acid sequence (SEQ ID NO:6): AAT-AGGGTTT ATTTAGACAC TGTGTCAGGT, which codes for amino acids 51–60 of mature LFA-3. However, the preferred DNA sequences of this invention encode polypeptides having the amino acid sequences of amino acids 29–120 of SEQ ID NO:10, amino acids 29–108 of SEQ ID NO:10, amino acids 48–108 of SEQ ID NO:10, and SEQ ID NO:7. The most preferred DNA sequence of this invention encodes a polypeptide having the amino acid sequence 1–120 of SEQ ID NO:10. This sequence when employed in animal cells allows production, secretion and maturation of a polypeptide having the amino acid sequence of amino acids 29–120 of SEQ ID NO:10.

It will be appreciated by those of skill in the art that, due to the degeneracy of the genetic code, DNA molecules comprising many other nucleotide sequences will also be capable of encoding the polypeptides of this invention. These degenerate sequences are encompassed by the present invention.

The present invention also relates to recombinant DNA molecules comprising the aforementioned DNA sequences. The recombinant DNA molecules of this invention are capable of directing expression of the LFA-3 polypeptides of this invention in hosts transformed therewith. A DNA sequence encoding an LFA-3 polypeptide of this invention must be operatively linked to an expression control sequence for such expression. The term "operatively linked" as used herein refers to positioning in a vector such that transcription and translation of the coding sequence is directed by the control sequence.

To construct a recombinant DNA molecule capable of directing expression of the LFA-3 polypeptides of this invention, the DNA sequences encoding these polypeptides may be inserted into and expressed using a wide variety of vectors. Furthermore, within each specific expression vector, various sites may be selected for insertion of these DNA sequences. These sites are usually designated by the restriction endonuclease which cuts them. They are well recognized by those of skill in the art. It will be appreciated, however, that an expression vector useful in this invention need not have a restriction endonuclease site for insertion of the chosen DNA fragment. Instead, the vector may be joined to the fragment by alternative means.

The expression vector, and in particular the site chosen for insertion of a selected DNA fragment and operative linking to an expression control sequence, is determined by a variety of factors. These factors include, e.g., the number of sites susceptible to a particular restriction enzyme, the size of the polypeptide to be expressed, susceptibility of the desired polypeptide to proteolytic degradation by host cell enzymes, contamination or binding of the polypeptide to be expressed by host cell proteins difficult to remove during purification, expression characteristics, such as the location of start and stop codons relative to the vector sequences, and other factors recognized by those skilled in the art. The choice of a vector and an insertion site for a DNA sequence is determined by a balance of these factors and not all selections will be equally effective for a given case.

Useful expression vectors for eukaryotic hosts include, for example, vectors comprising expression control sequences from SV40, bovine papilloma virus, adenovirus and cytomegalovirus, and vectors useful specifically in insect cells, such as pVL 941. Useful bacterial expression vectors include known bacterial plasmids, e.g., plasmids from *E.coli* including colE1, pcR1, pBR322, pMB9 and their derivatives; wider host range plasmids, such as RP4; the numerous derivatives of phage lambda, e.g., NM 989 and the lambda gt series; other DNA phages, e.g., M13 and other filamentous single-stranded DNA phages; and commercially available high expression vectors, e.g., the pGEM series and the lambda Zap vectors. Useful mammalian cell expression vectors include, for example, pNUT. Vectors useful in yeasts include, for example, the $2\mu$ plasmid and derivatives thereof.

Such expression vectors are also characterized by at least one expression control sequence that may be operatively linked to the DNA sequences of this invention inserted in the vector in order to control and to regulate the expression of that cloned DNA sequence. Examples of useful expression control sequences include the malE system, the OmpA system, the lac system, the trp system, the tac system, the trc system, major operator and promoter regions of phage lambda, the control region of fd coat protein, the glycolytic promoters of yeast, e.g., the yeast acid phosphatase, e.g., Pho5, the promoters of the yeast mating factors, and promoters derived from polyoma, adenovirus, retrovirus, and simian virus, e.g., the early and late promoters of SV40, eukaryotic cell promoters, such as the metallothionein promoter and other sequences known to control the expression of genes of prokaryotic or eukaryotic cells and their viruses or combinations thereof.

The recombinant DNA molecules of the present invention may also comprise other DNA coding sequences fused to and in frame with the DNA sequences of this invention. For example, such constructs may be characterized by an ATG start codon fused directly to the nucleotides encoding the first amino acid of the LFA-3 polypeptide. This construction may produce an f-Met polypeptide. However, it will be understood that the initial methionine may be cleaved during expression in a transformed host or may be subsequently removed. Alternatively, a DNA sequence encoding a bacterial or eukaryotic signal sequence may be fused to the 5' end of a DNA sequence encoding an LFA-3 polypeptide of this invention. This would allow the expressed product to be either secreted or targeted to a specific subcellular compartment within the host cell. Most signal sequences are removed by the host cell after performing their targeting function, thus obviating the need for removal after purification of the desired polypeptide. Many signal sequences, as well as the DNA sequences encoding them, are known in the art. The fusion protein of such signal sequence DNA to and in frame with the sequence encoding an LFA-3 polypeptide of this invention can be achieved by standard molecular biology techniques.

Alternatively, a DNA sequence encoding an LFA-3 polypeptide of this invention may be expressed as a fusion protein by in-frame ligation to a second DNA sequence encoding a host cell polypeptide. The expression of a fusion protein may afford several advantages, such as increased resistance to host cell degradation, ease of identification based upon the activity or antigenicity of the host cell polypeptide, and ease of purification, based upon the physical or immunological properties of the host cell polypeptide.

This invention also relates to hosts transformed with the recombinant DNA molecules described above. Useful hosts which may be transformed with these recombinant DNA molecules and which may be employed to express the LFA-3 polypeptides of this invention may include well known eukaryotic and prokaryotic hosts, such as strains of E.coli, e.g., E.coli SG-936, E.coli HB 101, E.coli W3110, E.coli X1776, E.coli X2282, E.coli DH1, E.coli DH5-alpha, E.coli MRC1; strains of Pseudomonas; strains of Bacillus, such as Bacillus subtilis; strains of Streptomyces; strains of Saccharomyces; animal cells, such as COS cells, CHO cells, BHK cells, human tissue cells; insect cells (e.g., Spodoptera frugiperda (SF9)); and plant cells in tissue culture. The preferred host for polypeptides claimed herein is CHO cells.

It will be appreciated that not all host/expression vector combinations will function with equal efficiency in expressing DNA sequences encoding the LFA-3 polypeptides of this invention. However, a particular selection of a host-expression vector combination may be made by those of skill in the art after due consideration of the principles set forth herein without departing from the scope of this invention. For example, the selection should be based on a balancing of a number of factors. These factors include, for example, compatibility of the host and vector, toxicity of the polypeptides encoded by the DNA sequence to the host, vector copy number and the ability to control that copy number, the expression of other proteins encoded by the vector, such as antibiotic markers, ease of recovery of the desired protein, expression characteristics of the DNA sequences and the expression control sequences operatively linked to them, biosafety, costs and the folding, form or any other necessary post-expression modifications of the desired polypeptide.

While recombinant DNA techniques are the preferred method of producing the polypeptides of this invention having a sequence of more than 20 amino acids, shorter polypeptides encompassed by this invention having less than about 20 amino acids are preferably produced by conventional chemical synthesis techniques. Synthetically produced polypeptides of this invention can advantageously be obtained in extremely high yields and be easily purified.

In a preferred embodiment of this invention, the polypeptides are synthesized by solution phase or solid phase polypeptide synthesis and, optionally, digested with carboxypeptidase (to remove C-terminal amino acids) or degraded by manual Edman degradation (to remove N-terminal amino acids). Proper folding of the polypeptides may be achieved under oxidative conditions which favor disulfide bridge formation, as described by S. B. H. Kent, "Chemical synthesis of polypeptides and proteins", Ann. Rev. Biochem., 57, pp. 957–89 (1988). Polypeptides produced in this way may then be purified by separation techniques widely known in the art, preferably utilizing reverse phase HPLC. The use of solution phase synthesis advantageously allows for the direct addition of certain derivatized amino acids to the growing polypeptide chain, such as the O-sulfate ester of tyrosine. This obviates the need for a subsequent derivatization step to modify any residue of the polypeptides of this invention.

The biological activity of the polypeptides of this invention, i.e., their ability to block LFA-3/CD2 interaction, may be assayed using a simple cell binding assay that permits visual (under magnification) evaluation of the binding of LFA-3 polypeptide-expressing cells to CD2-expressing cells. Jurkat cells are preferred as the $CD2^+$ substrate (see Examples, infra.). The binding characteristics of soluble polypeptides according to the invention may be assayed in several known ways, such as by radiolabeling the polypeptide with, e.g., $^{35}S$, and then contacting the labeled polypeptide with $CD2^+$ cells. Enzymatic labels or rosetting assays such as described by Seed et al. (Proc. Natl. Acad. Sci. USA, 84, pp. 3365–69 (1987)) may also be used.

In another embodiment of this invention, fusion proteins and DNA sequences coding for them are provided. These fusion proteins have an amino-terminal region characterized by the amino acid sequence of a CD2-binding polypeptide of this invention and a carboxy-terminal region comprising a domain of a protein or polypeptide other than LFA-3. Such domains include, for example, the Fc region of an immunoglobulin.

In the preferred fusion proteins of this invention, the CD2-binding polypeptides of this invention are fused to at least a portion of the Fc region of an immunoglobulin. In these fusion proteins, the CD2-binding polypeptides form the amino-terminal portion, and the Fc region forms the carboxy terminal portion.

In these fusion proteins, the Fc region is preferably limited to the hinge region and the $C_H2$ and $C_H3$ domains. More preferably, the Fc region in the fusion proteins of this invention is limited to a portion of the hinge region, the portion being capable of forming intermolecular disulfide bridges, and the $C_H2$ and $C_H3$ domains. See, e.g., FIGS. 12A and 12B.

Figure 11:
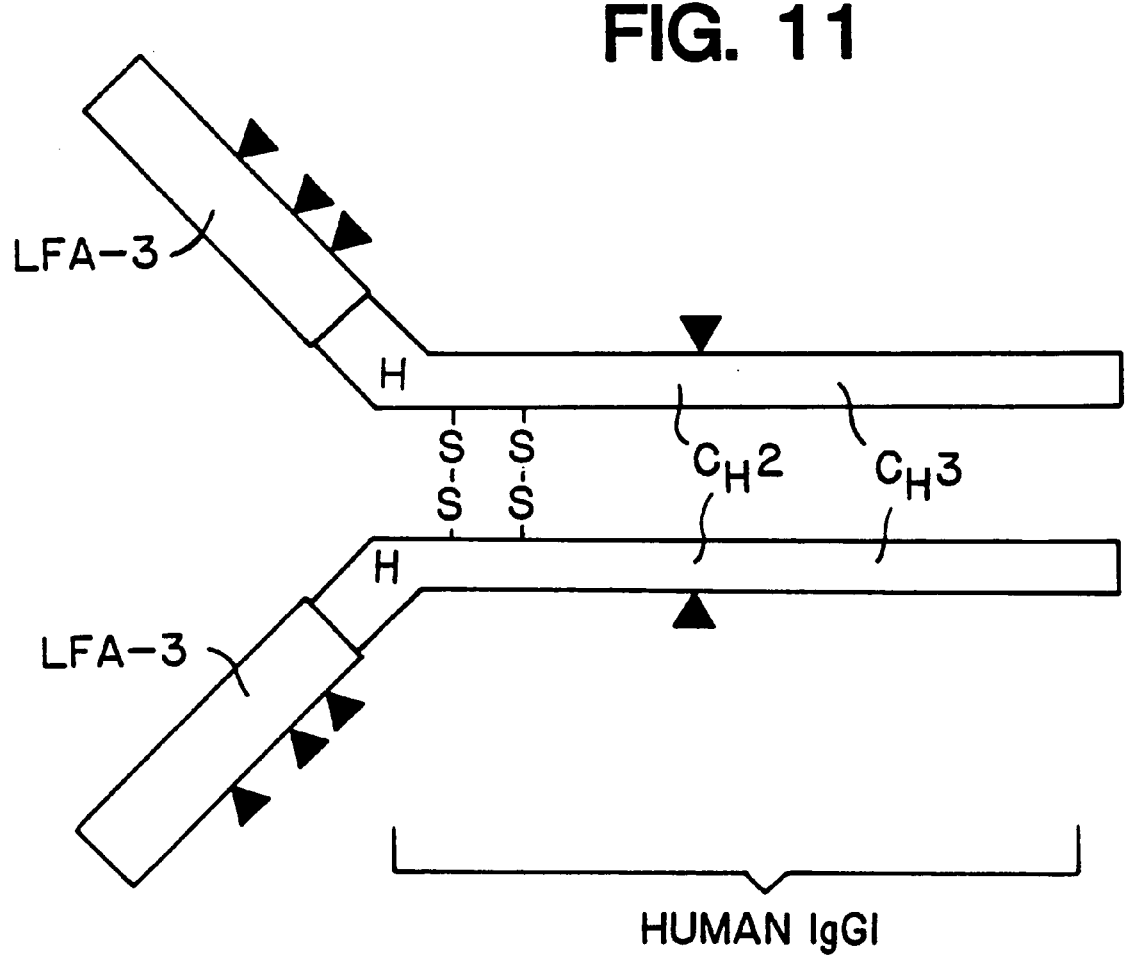
FIG. 11 is a diagram of a dimer of LFA3TIP, depicting the various domains of this LFA-3-Ig fusion protein. As depicted in this figure, "LFA-3" refers to the amino terminal 92 amino acids of mature LFA-3. "H" refers to the ten amino acids of the IgG1 hinge region containing two cysteines to form two intermolecular disulfide bonds. Each disulfide bond is depicted as horizontal double SS. "$C_H2$" and "$C_H3$" refer to the two constant domains present in the FC region, below the hinge region, in human IgG1 molecules.

An example of a useful LFA-3-Ig fusion protein of this invention is LFA3TIP (also referred to as LFA-3(92)IgG), which is secreted into the cell culture medium by COS7 cells containing the expression plasmid pSAB152 (see infra). LFA3TIP consists of the amino terminal 92 amino acids of the mature form of LFA-3 fused to a portion of the hinge region and the $C_H2$ and $C_H3$ constant domains of human IgG1 (see FIG. 11). The fusion protein, LFA3TIP, contains a functional CD2-binding domain of LFA-3 and a sufficient portion of the Fc region of IgG to be recognized by the Fc binding protein, Protein A. LFA3TIP is able to bind to CD2 and inhibit T-cell activation.

It will be apparent that the polypeptides and fusion proteins of this invention may be used in methods to selectively isolate CD2 or CD2-expressing cells, based on the formation of a complex between the CD2-binding domain of those polypeptides and CD2.

In another embodiment of this invention, the polypeptides and fusion proteins of this invention, such as the LFA-3-Ig fusion proteins, may be used to label cells expressing CD2 or a polypeptide containing the LFA-3 binding domain of CD2. For example, the polypeptides and fusion proteins of this invention may be conjugated to a "reporter molecule" which allows detection of the polypeptides or fusion proteins bound to $CD2^+$ cells or polypeptides containing the CD2-binding domain of LFA-3. Owing to the presence of a portion of the immunoglobulin Fc region in the illustrative fusion proteins of this invention, such fusion proteins can be conjugated to the same "reporter molecules" which are commonly conjugated or bound to immunoglobulins in order to detect immunoglobulins bound to antigens, e.g., $^{125}I$, enzyme-conjugated secondary antibodies directed to the Fc region, or biotin-streptavidin based enzyme conjugated molecules. Accordingly an LFA-3-Ig fusion protein of this invention may be conjugated or bound to such reporter molecules via its Fc carboxy-terminal portion. Furthermore, such reporter molecules may be conjugated or bound to the polypeptides or fusion proteins of this invention before or after the polypeptides or fusion proteins have bound to CD2 or to the LFA-3 binding domain of CD2.

It is a further embodiment of this invention that the polypeptides and fusion proteins of this invention can also be used in diagnostic applications to detect the presence or indicate the absence of CD2 or cells or molecules containing the LFA-3-binding domain of CD2.

The polypeptides and fusion proteins of this invention can also be used in therapeutic compositions to inhibit formation of the CD2/LFA-3 complex, when such formation contributes to a pathological state. Alternatively, they may be used therapeutically to mimic the role of LFA-3 in initiating one or more of the T-lymphocyte functional responses dependent on the formation of the CD2/LFA-3 complex (see, e.g., Dustin et al., *J. Exp. Med.*, 165, pp. 677–92 (1987); Springer et al., *Ann. Rev. Immunol.*, 5, pp. 223–52 (1987)). For example, the polypeptides and fusion proteins of this invention may be used in the treatment of acute and chronic inflammation, autoimmune diseases, and for immunomodulation, including treatment of such diseases as systemic lupus erythematosus or lupus vulgaris, rheumatoid arthritis and thyroiditis. Furthermore, the polypeptides and fusion proteins of this invention may be used to inhibit T-cell activation or to inhibit proliferation of peripheral blood lymphocytes.

In these respects, it is recognized that molecules involved in cell—cell adhesion are generally more effective in eliciting a particular response from a cell when the molecules are present in a multimeric form as opposed to a monomeric form of the same protein. Multimeric forms of cell surface adhesion proteins appear to more closely mimic the typical situation in vivo where, e.g., an effector cell will exhibit hundreds or thousands of copies of a particular adhesion protein on its surface which then bind to the many copies of its ligand on a target cell. When many surface molecules become involved in binding, they may act synergistically, so that the affinity of one cell for another is greater than the mere sum of the binding affinities of the individual molecules. Accordingly, an important aspect of this invention concerns the preparation and use of multimeric forms of the CD2-binding polypeptides disclosed herein.

A variety of methods are known in the art to form multimeric forms of protein monomers. Such methods include using crosslinking agents, e.g., glutaraldehyde (e.g., Reichlin, *Methods Enzymol.*, 70, pp. 159–65 (1980)). If thiol residues are present on a polypeptide or polypeptides, such groups may be oxidized to form intermolecular disulfide bonds to achieve multimeric forms of the polypeptide or polypeptides. Thiol residues or thiol-reactive groups may be introduced into a polypeptide using iminothiolane or heterobifunctional cross-linkers, such as N-succinimidyl-3-(2-pyridyldithio)propionate (SPDP), which contains an amine-reactive group and a thiol-reactive group. Coupling of the proteins may then be accomplished through disulfide bonds formed either directly or through homobifunctional cross-linking agents (see, e.g., Srinivasachar et al., *Biochem.*, 28, pp. 2501–09 (1989); Ramakrishnan et al., *Cancer Res.*, 44, pp. 201–08 (1984); Lambert et al., *J. Biol. Chem.*, 260, pp. 12035–41 (1985)). The effectiveness of disulfide bond formation between molecules would of course be limited to the number of thiols available on the polypeptide (naturally occurring or introduced by derivatization as above) and whether such disulfide bond formation adversely affected the affinity of the resulting multimeric form.

If polypeptides or proteins possess carbohydrate groups, such as in glycoproteins, the sugar moieties of such groups may be used in reactions to link one molecule with another (e.g., Liao et al., *J. Biol. Chem.*, 248, pp. 8247–53 (1973); Moroney et al., *Biochem.*, 26, pp. 8390–98 (1987)).

Other multimeric forms of the CD2-binding polypeptides of this invention may be produced by attaching a phosphatidylinositol ("PI") linkage sequence, e.g., as described in PCT patent application PCT/US90/01859, or sequences of C4 binding protein, e.g., as described in PCT patent application PCT/US91/00567. The hydrophobic PI anchor may be used to form micelles exhibiting a plurality of active CD2-binding domains or multimeric forms of the PI-linked LFA-3, in which a plurality of monomers are associated with one another by hydrophobic interactions between the PI linkage sequences of each monomer (in the absence of added lipids or membrane). In this latter case, multimeric PI-linked LFA-3 molecules are usually octamers; though other polymeric forms have been observed (e.g., 6–12 associated monomers). Alternatively, attaching a segment of DNA encoding the PI linkage sequence downstream of a DNA insert encoding a polypeptide of the invention, and transfecting suitable mammalian host cells with this construct, will provide a culture of cells exhibiting numerous copies of the CD2-binding polypeptide on their surfaces (attached by a PI anchor).

Alternatively, multiple copies of monomers of polypeptides and fusion proteins of this invention may be bound to another molecule or substrate or particle. As in the case of the binding of LF08 to Affigel-10 beads (see infra), the formation and use of molecules, compounds or particles comprising multiple CD2-binding domains are within the scope of this invention.

In addition, this invention also includes multimeric forms of LFA-3-Ig fusion proteins. Such multimers may be generated by using those Fc regions, or portions thereof, of Ig molecules which are usually multivalent, e.g., IgM pentamers and IgA dimers. It is of course understood that a J chain polypeptide may be necessary to form and stabilize IgM pentamers and IgA dimers. Alternatively, multimers of LFA-3-Ig fusion proteins may be formed by using a protein with an affinity to the Fc region of Ig molecules, such as Protein A. For example, a plurality of LFA-3-Ig fusion proteins, such as LFA3TIP, may be bound to Protein A-agarose beads to form agarose beads whose surfaces are covered with multiple functional CD2-binding domains of the attached LFA-3-Ig fusion proteins.

In another embodiment, this invention provides multimeric proteins capable of binding to CD2, which comprise (a) two or more of the CD2-binding polypeptides described herein, (b) two or more of the CD2-binding fusion proteins described herein, or (c) one or more of the CD2-binding polypeptides and one or more of the CD2-binding fusion proteins.

The polypeptides of this invention may also be used to design low molecular weight (i.e., usually monomeric molecular weights of less than 1000 daltons) nonpeptidyl or only partial peptidyl CD2-binding molecules useful to inhibit cell—cell adhesion via formation of the CD2/LFA-3 complex. Based on the polypeptides provided herein, such small molecules may be designed which possess the ability to bind CD2 and may consist of moieties other than amino acids and may be produced entirely through synthetic methods. The use of such small molecules as therapeutic or diagnostic agents also falls within the scope of this invention.

Another embodiment of this invention involves the use of the CD2-binding polypeptides and fusion proteins to obtain antibodies recognizing the CD2-binding domain of LFA-3. Both monoclonal antibodies (MAbs) and polyclonal antibodies highly specific to the CD2-binding domain of LFA-3 may be obtained utilizing the polypeptides and fusion proteins of this invention.

Methods for obtaining monoclonal antibodies and polyclonal antiserum to a particular antigen are well known in the art. For producing MAbs, an immortal cell line (typically a myeloma cell line) is fused to lymphocytes (typically splenocytes) from a mammal (e.g., a rabbit) immunized with a particular antigen, i.e., in this case the CD2-binding domain of LFA-3. Such fusions usually generate hybridomas, i.e., immortal clones of hybrid cells which produce antibody molecules specific for a single epitope of the immunizing antigen (see, generally, Kohler et al., *Nature*, 256, pp. 495–97 (1975)). Effective immunization may require that the polypeptide comprising the CD2-binding domain be polymerized or derivatized and mixed with an adjuvant.

It is also necessary to be able to screen the potentially numerous clones of hybridomas generated from the fusions in order to identify those clones which produce antibodies to the CD2-binding domain of LFA-3. For example, such screens may involve assaying the supernatants of cultures of hybridomas for the ability to inhibit CD2-expressing cells from binding to LFA-3 expressing cells. Assays which have been used to screen hybridomas for the production of MAbs to LFA-3 are applicable as primary screens for hybridomas producing MAbs specific for the CD2-binding domain of LFA-3 (see, e.g., Sanchez-Madrid et al., *Proc. Natl. Acad. Sci. USA*, 79, pp. 7489–93 (1982)).

The DNA encoding the CD2-binding polypeptides of this invention and of deletion mutant forms of the LFA-3 gene, such as those described herein, may also be used as plus/minus probes to detect and isolate other DNA sequences encoding the CD2-binding domain of LFA-3.

The deletion mutant forms of the LFA-3 protein, which lack at least amino acids +51 to +60 of mature LFA-3; at least amino acids +41 to +50 of mature LFA-3 or at least amino acids +31 to +40 of mature LFA-3; (and preferably lack all 3 regions) may be used to clear polyclonal antiserum of antibodies which recognize epitopes of LFA-3 other than the epitopes within the CD2-binding domain of LFA-3. Such mutants may be, for example, selected from the group consisting of M57, M55, M56, PIM3 and M100, and combinations thereof. For example, a polyclonal anti-LFA-3 antiserum may be preincubated with a mutant form of the LFA-3 protein encoded by the mutant LFA-3 gene containing the M57 or M100 deletion mutations (FIGS. 1A-1, 1A-2 and 1B and FIGS. 6A-1, 6A-2 and 6B). The polyclonal antibodies recognize and bind LFA-3 epitopes on the mutant LFA-3 protein. However, since the CD2-binding domain is not present, antibodies to this epitope in the polyclonal antiserum will not bind. Precipitation of the complexes that do form will result in an enrichment for any antibodies remaining in the antiserum that are specific for epitopes of the CD2-binding domain.

The CD2-binding domain polypeptides and fusion proteins of this invention may be formulated as pharmaceutical compositions using conventional methods to prepare pharmaceutically useful compositions and combinations. Such compositions preferably include at least one pharmaceutically acceptable carrier. See, e.g., *Remington's Pharmaceutical Sciences,* (E. W. Martin). Pharmaceutical compositions of the present invention typically contain, in addition to the active polypeptide, a pharmaceutically acceptable buffer, preferably phosphate buffered saline, together with a pharmaceutically acceptable compound for adjusting isotonic pressure, such as sodium chloride, mannitol or sorbitol. The pharmaceutically acceptable compositions and methods of this invention are characterized by pharmaceutically effective amounts of a polypeptide according to the invention.

The pharmaceutical compositions and combinations of this invention which comprise LFA-3-Ig fusion proteins may be used, for example, to inhibit the activation of T-lymphocytes or to inhibit the proliferation of peripheral blood lymphocytes (see infra).

The term "combination" as used herein, includes a single dosage form containing at least one polypeptide of this invention and at least one other pharmaceutically active agent, a multiple dosage form wherein the polypeptide and the other active agent are administered separately, but concurrently, or a multiple dosage form wherein the two components are administered separately but sequentially. Alternatively, the polypeptides of this invention and the other active agent may be in the form of a single conjugated molecule. Conjugation of the two components may be achieved by standard cross-linking techniques well known in the art. A single molecule may also take the form of a recombinant fusion protein.

The pharmaceutical compositions and combinations of this invention may be administered to a patient in any pharmaceutically acceptable dosage form, including, but not limited to, those which may be administered to a patient intravenously as a bolus or by continued infusion, intramuscularly, subcutaneously, intracutaneously, intra-articularly, orally or parenterally.

Methods for determining pharmaceutically effective dosages are known to those skilled in the art. The dosage and dose rate will depend on a variety of factors such as the specific composition, the object of the treatment, i.e., therapy or prophylaxis, method of administration, and the judgment of the treating physician.

This invention also relates to the bioanalytic use of CD2-binding polypeptides and fusion proteins, or compositions containing them, for determining the concentration of CD2 proteins or the detection of CD2-expressing cells in a biological sample. These polypeptides and compositions may be used in a manner similar to that of reagents employed in conventional assays. In addition, the polypeptides of this invention may be utilized in diagnostic kits designed to detect the presence and measure the concentration of CD2 or CD2-expressing cells.

In order that this invention may be better understood, the following examples are set forth. These examples are for purposes of illustration only, and are not to be construed as limiting the scope of this invention.

EXAMPLE 1
Preparation of Deletion Mutations in the LFA-3 Gene

In order to map the CD2-binding domain on the LFA-3 protein, a series of deletion mutations of the LFA-3 gene were systematically generated using site-specific mutagenesis by oligonucleotide heteroduplexing. cDNA encoding transmembrane has been isolated and sequenced (see, Wallner et al., U.S. Pat. No. 4,956,281), and a bacteriophage bearing cDNA coding for transmembrane LFA-3 was deposited with American Type Culture Collection in Rockville, Md. (accession number 75107). A plasmid, pHT16-6, containing cDNA encoding transmembrane LFA-3 was obtained from Biogen, Inc. (Cambridge, Mass.) and used in preparing all the deletion mutations. The construction of plasmid pHT16-6 is described in PCT patent publication WO 88/09820, which is herein incorporated by reference. Plasmid pHT16-6 contains a cDNA insert encoding LFA-3 and contains a unique EcoRI site near the 5' end of the LFA-3 coding sequence, a unique BamHI site adjacent the 5' end of the LFA-3 cDNA, a unique HindIII site adjacent the 3' end of the LFA-3 cDNA, two NotI sites 1112 bp apart and bracketing the LFA-3 cDNA, and a unique ScaI site. The cDNA insert of pHT16-6 containing the entire coding region for transmembrane LFA-3 is shown in FIGS. 1A-1 and 1A-2.

In this procedure, seventeen sequences of the LFA-3 coding sequence, each 30 bp long, were selected for deletion. For each proposed deletion, a 30-base antisense oligonucleotide (30-mer) was synthesized which consisted of the complementary 15 bases immediately upstream of (5' to) the proposed deletion and the complementary 15 bases immediately downstream of (3' to) the proposed deletion. Hybridization of a particular synthetic oligonucleotide to a strand of the LFA-3 DNA resulted in a heteroduplex in which a specific sequence of 30 bp would loop out. By this mutagenesis procedure, some of the replication products of the heteroduplex contained deletion mutations lacking the 30 bp region looped out by heteroduplex formation.

The synthetic oligonucleotides used to generate the seventeen deletion mutants depicted in FIGS. 1A-1, 1A-2 and 1B are set forth in the following table:

| Sequence | Complementary to LFA-3 Nucleotides | Segment Deleted |
| --- | --- | --- |
| SEQ ID NO:13 | 109–123 + 154–168 | M53 |
| SEQ ID NO:14 | 139–153 + 184–198 | M54 |
| SEQ ID NO:15 | 169–183 + 214–228 | M55 |
| SEQ ID NO:16 | 199–213 + 244–258 | M56 |
| SEQ ID NO:17 | 229–243 + 274–288 | M57 |
| SEQ ID NO:18 | 259–273 + 304–318 | M58 |
| SEQ ID NO:19 | 289–303 + 334–348 | M59 |
| SEQ ID NO:20 | 319–333 + 364–378 | M60 |
| SEQ ID NO:21 | 349–363 + 394–408 | M61 |
| SEQ ID NO:22 | 379–393 + 424–438 | M62 |
| SEQ ID NO:23 | 409–423 + 454–468 | M63 |
| SEQ ID NO:24 | 439–453 + 484–498 | M64 |
| SEQ ID NO:25 | 469–483 + 514–528 | M65 |
| SEQ ID NO:26 | 499–513 + 544–558 | M66 |
| SEQ ID NO:27 | 529–543 + 574–588 | M90 |
| SEQ ID NO:28 | 559–573 + 604–618 | M91 |
| SEQ ID NO:29 | 589–603 + 634–648 | M92. |

For each heteroduplex, one sample of plasmid pHT16-6 (100 µg) was digested with HindIII (210 units, New England Biolabs) and either EcoRI (300 units, New England Biolabs) or BamHI (300 units, New England Biolabs). Another sample of pHT16-6 (100 µg) was linearized by digestion with ScaI (300 units, New England Biolabs). Digestion products were electrophoresed on 1 percent (w/v) agarose gels in TAE buffer (40 mM Tris/acetate, 1 mM EDTA, pH 8.0), and the desired fragment from each digestion was then electroeluted from the gel (Maniatis et al., *Molecular Cloning: A Laboratory Manual* (Cold Spring Harbor, 1982)). In the case of the ScaI digestion, the linearized pHT16-6 was electroeluted from the gel; in the case of the HindIII/EcoRI or HindIII/BamHI digestions of pHT16-6, the larger of two restriction fragments produced in each case was electroeluted.

A sample of the ScaI linearized pHT16-6 DNA (100 ng) was mixed with a sample of the isolated HindIII/EcoRI or HindIII/BamHI restriction fragment (100 ng) and with 8 picomoles of one of the seventeen antisense oligonucleotides previously phosphorylated with ATP (Maniatis et al., supra). Referring to FIGS. 1A-1, 1A-2 and 1B, since the EcoRI restriction site is located in the M56 region, the HindIII/EcoRI large restriction fragment could not be used to generate deletions of regions M53, M54, M55 and M56. Thus, the HindIII/BamHI large restriction fragment was used in the procedure to generate these four deletions.

In order to form heteroduplexes, a synthetic oligonucleotide, ScaI-linearized pHT16-6, and either HindIII/EcoRI or HindIII/BamHI large fragment of pHT16-6 were mixed in 100 mM NaCl, 80 mM MgCl$_2$, 6.5 mM Tris/Cl, pH 7.6 and boiled for 3 minutes to denature. The denatured DNA was allowed to anneal at 37° C. for 1 hour, then at 4° C. for 1 hour, and finally at 0° C. for 10 minutes.

After annealing, the gaps in the heteroduplexes were filled in and the fragments ligated in a single reaction mixture by adding to the annealed DNA the following constituents to give the indicated final concentrations or amounts: ATP (20 mM); dATP, dTTP, dGTP, dCTP (each at 10 mM); Klenow (large fragment of DNA Polymerase I, 2.5 units, New England Biolabs); T4 DNA ligase (200 units, New England Biolabs). The mixtures were then incubated overnight at 15° C.

After incubation, half of each fill-in/ligation mix was used to transform 100 µl of *E.coli* JA221 (Maniatis et al., supra). Colonies of transformed cells were selected on LB plates supplemented with ampicillin (50 µg/ml) (Maniatis et al., supra).

Colonies of transformants were screened for the presence of a particular deletion by colony hybridization using the particular oligonucleotide used in the heteroduplex to generate the deletion as a probe.

For use as probes, a sample of each oligonucleotide (80 pmol) was labeled using $^{32}$P-ATP by standard procedures. The labeled oligonucleotides were precipitated with 2 M ammonium acetate (Maniatis et al., supra). Labeled probe was added to the hybridization buffer at a final activity of approximately 5×10$^5$ CPM/ml of hybridization mixture. Hybridizations were carried out on nitrocellulose filters at 60° C. for about 8 hours. After washing the filters in 0.5×SSC buffer at 60° C., autoradiography was performed and positive colonies scored (Maniatis et al., supra). The generation of the desired deletion mutations was confirmed by DNA sequence analysis (Maxam and Gilbert, in *Methods in Enzymology* (Grossman and Moldave, eds.), 65, pp. 499–560 (1980)) of plasmid DNA in colonies scoring positive according to hybridization results.

These procedures produced plasmids, each containing one of the 30 bp deleted sequences listed above and depicted in FIGS. 1A-1, 1A-2 and 1B. The plasmid containing the M57 deletion in the LFA-3 coding sequence was designated plasmid pLFA3M57-4A.

EXAMPLE 2
Construction of Recombinant Expression Plasmids

Plasmids prepared according to Example 1 with successfully deleted 30 bp segments from the LFA-3 coding sequence were used for construction of expression vectors. Aliquots of 100 µg of plasmids having deleted segments (see FIGS. 1A-1, 1A-2 and 1B) M54, M55, M56, M57, M58, M63 and M65, respectively, were digested with NotI endonuclease (100 units, New England Biolabs, Beverly, Mass.). For M57, M63 and M65, the 5' overhangs were filled in using a standard Klenow (New England Biolabs) reaction mix (Maniatis et al., supra) to generate blunt ended restriction fragments. The fragments were purified from 0.7% TAE agarose gels by electroelution.

The gel-purified, blunt-ended, NotI fragments were then individually cloned into the SmaI site of the eukaryotic expression vector pBG368PY (Dailey et al., *J. Virol.*, 54, pp. 739–49 (1985)) using T4 ligase at 15° C. overnight. NotI fragments of M54, M55, M56, and M58 were gel purified as described above and ligated to NotI-digest expression vector, PMDR902. The resulting ligations were used to transform *E.coli* JA221 and positive colonies of transformants containing the recombinant plasmids carrying the desired inserts were identified by colony hybridization, as described above. The orientation of the M57, M63 and M65 inserts in the vector was confirmed by EcoRI digestion, generating 6600, 4000 and 200 bp fragments for correctly oriented inserts, which were separated on 0.7% agarose gel. For plasmids containing M54, M55, M56 and M58 inserts, the orientation was determined by PvuII digestion analysis, where the correct orientation generated fragments of 6599 bp, 1185 bp and 506 bp. All fragments were verified by DNA sequencing (Maxam and Gilbert, supra).

The recombinant expression plasmids carrying DNA encoding the M54, M55, M56, and M58 LFA-3 deletion mutations were linearized with AatII and electroporated into Chinese Hamster Ovary (CHO) cells according to the published protocol of J. Barsoum (*DNA Cell Biol.*, 9, pp. 293–300 (1990)). Plasmids carrying DNA encoding the M57, M63 and M65 deletion mutations were linearized using NruI and electroporated into CHO cells as above, except that 19 $\mu$g of the NruI-digested DNA was ethanol precipitated overnight at -20° C. with 1 $\mu$g of EcoRI-digested SV2 DNA (DHFR$^+$) and 380 $\mu$g of sonically disrupted salmon sperm DNA. CHO cells ($1 \times 10^7$) were electroporated with the coprecipitated DNA at 280 volts using a BioRad Gene Pulser.

After electroporation, cells were seeded into two 100 mm plates in alpha$^+$ MEM, 10% fetal calf serum (FCS), 4 mM L-glutamine, penicillin/streptomycin, then incubated for 48 hours at 37° C. The cells in the plates were then divided into five 100 mm plates containing alpha$^-$ MEM, 10% FCS, 4 mM L-glutamine, penicillin/streptomycin, and incubated for five days at 37° C. The cells were then fed with alpha$^-$ Complete Medium supplemented with 200 nM methotrexate for M57, M63 and M65, and 50 nM methotrexate for M54, M55, M56 and M58. Each plate was grown to 90% confluency then assayed by FACS (Fluorescence-Activated Cell Sorter) to determine whether any of the CHO cultures transfected with the LFA-3 deletion mutations expressed the mutant forms of LFA-3.

EXAMPLE 3
FACS Analysis of Transfected Cells

Transfected CHO cells, prepared in Example 2 and grown in the presence of methotrexate to 90% confluency, were rinsed twice with HANKS BSS medium (Ca$^{++}$ and Mg$^{++}$ free, pH 7.0) and removed with HANKS (Ca$^{++}$ and Mg$^{++}$ free, 5 mM EDTA, pH 7.0) medium. Approximately $2 \times 10^5$ cells were resuspended in 100 $\mu$l of a solution of cold (0° C.) wash buffer (PBS, 0.1% NaN$_3$, 0.5% bovine serum albumin (BSA), pH 7.2), and a primary antibody was added. The primary antibody was either anti-LFA-3 MAb TS2/9 ascites fluid (see, e.g., Sanchez-Madrid et al., *Proc. Natl. Acad. Sci. USA*, 79, pp. 7489–93 (1982), obtained from Dana Farber Cancer Inst., Boston, Mass.); the anti-LFA-3 MAb 7A6 (obtained from Biogen, Inc., Cambridge, Mass.; 1.6 $\mu$g/ml); or anti-LFA-3 polyclonal rabbit antiserum 202 (obtained from Biogen, Inc.). All the primary antibodies are known to block CD2 adhesion to LFA-3. The amount of primary antibody used was typically between 1 and 2 $\mu$l. Cells were incubated at 0° C. for 45 minutes and washed twice with wash buffer.

A fluorescein-labeled secondary antibody was then added and the mixture incubated for 30 minutes at 0° C. For analysis with the monoclonal antibodies, the secondary antibody was fluorescein (DTAF)-conjugated affinity purified goat anti-mouse F(ab)$_2$ IgG (H+L) (Jackson Immunoresearch Laboratories, Inc., West Grove, Calif.); for use with the polyclonal rabbit antiserum 202, the secondary antibody was fluorescein isothiocyanate (FITC) goat anti-rabbit IgG (H+L) (Fisher Biotech, Pittsburgh, Pa.).

After incubation with the secondary antibody, cells were overlayed with 300 $\mu$l FCS, washed twice in wash buffer, resuspended in 300 $\mu$l×PBS and transferred to Falcon 2052 tubes to be read on the cell sorter.

Figure 2B:
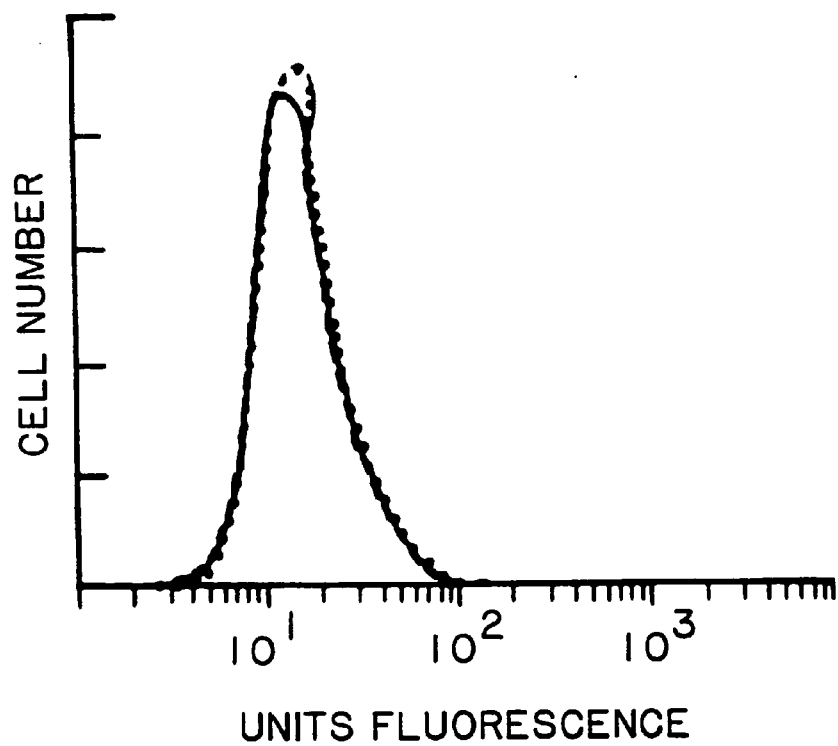
Figure 2C:
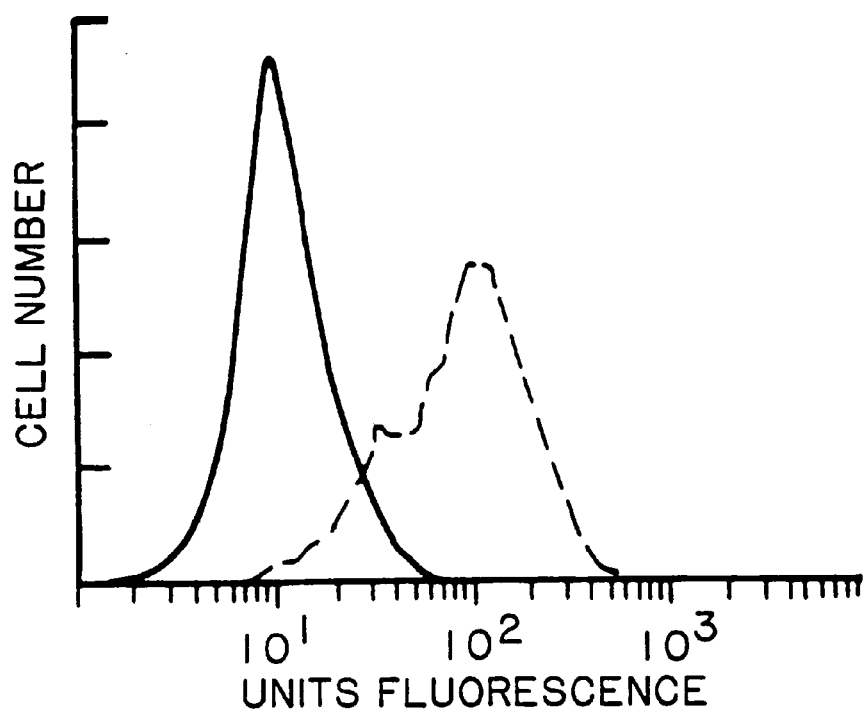
Figure 2D:
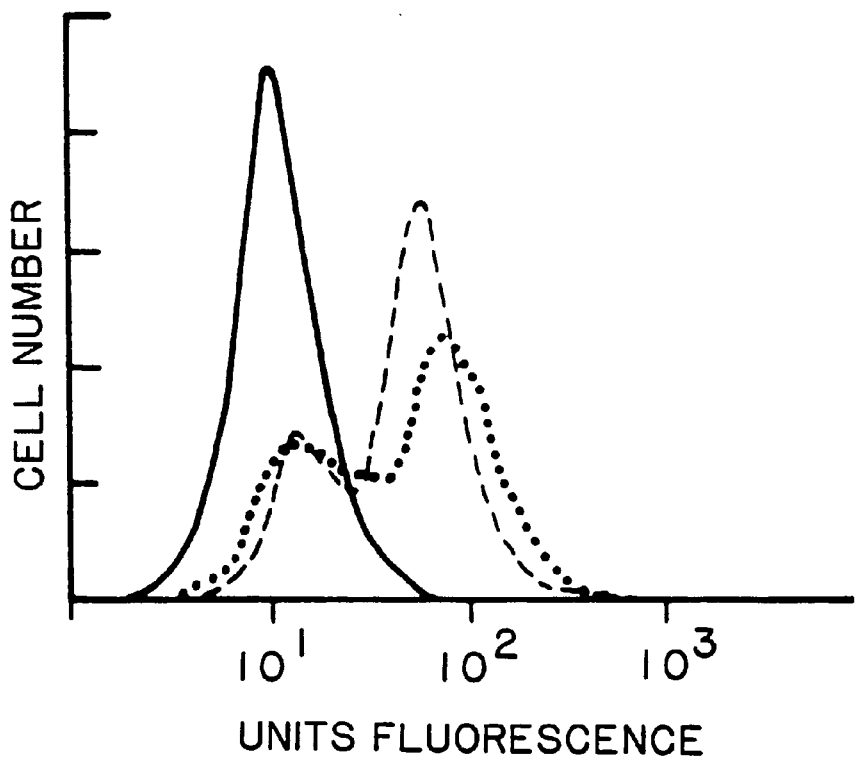
Figure 2E:
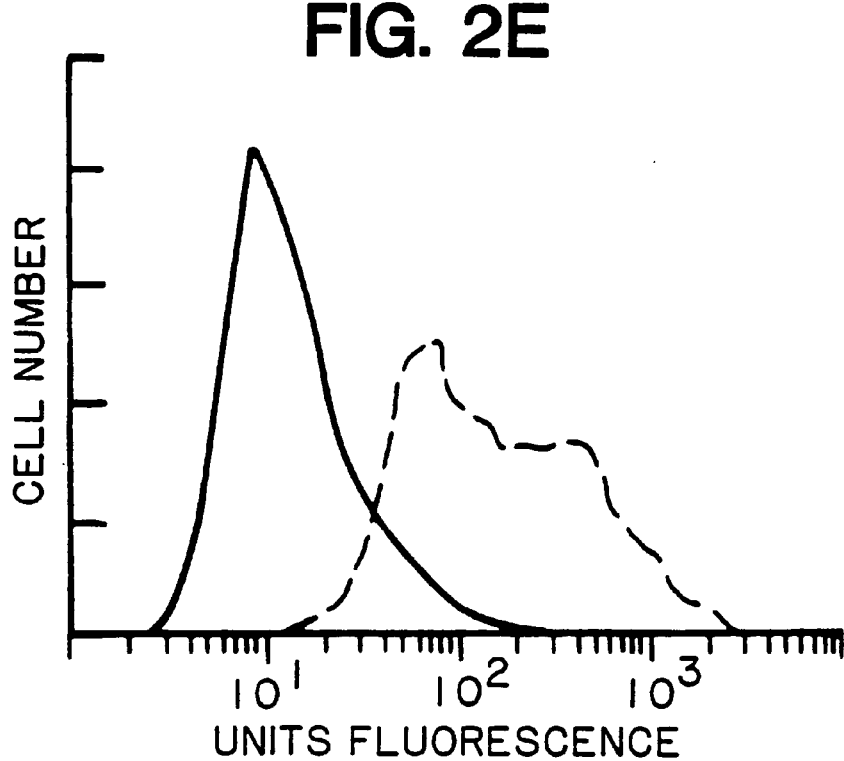
Figure 2F:
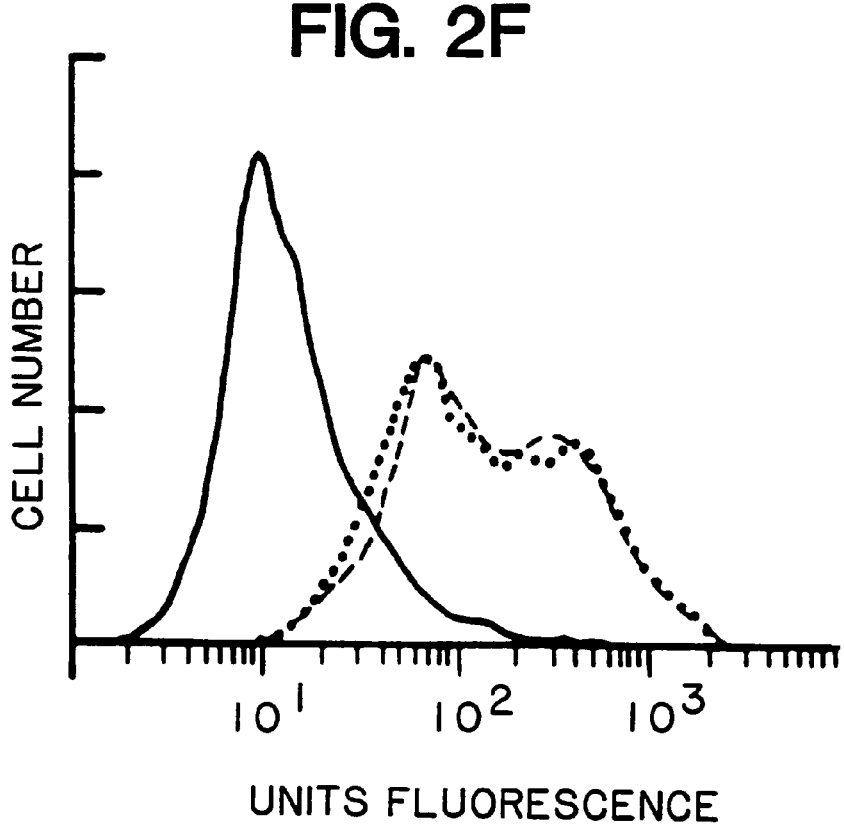
Figure 2G:
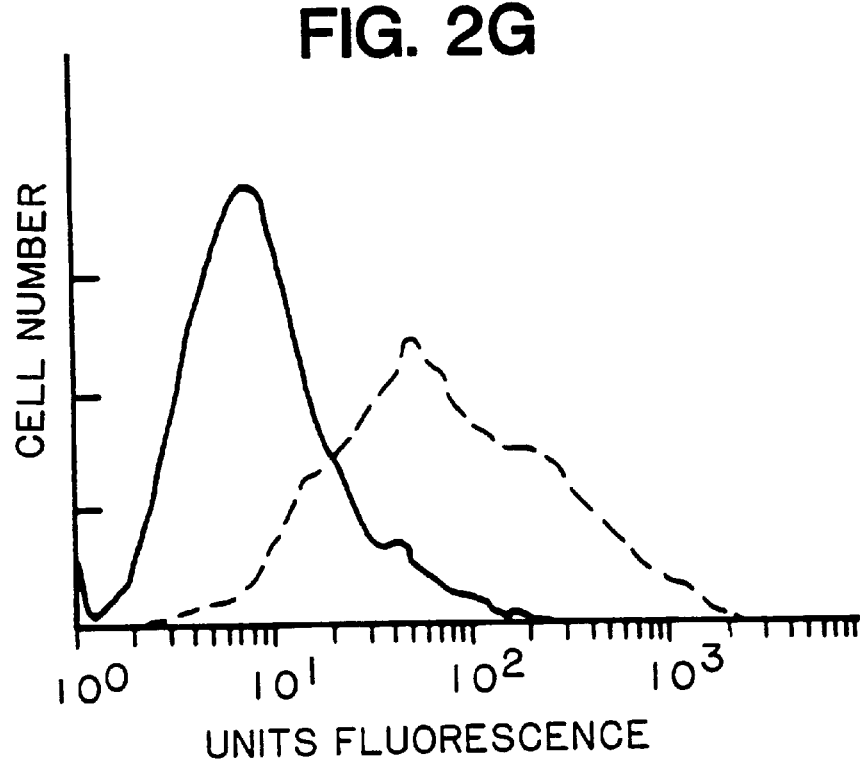
Figure 2H:
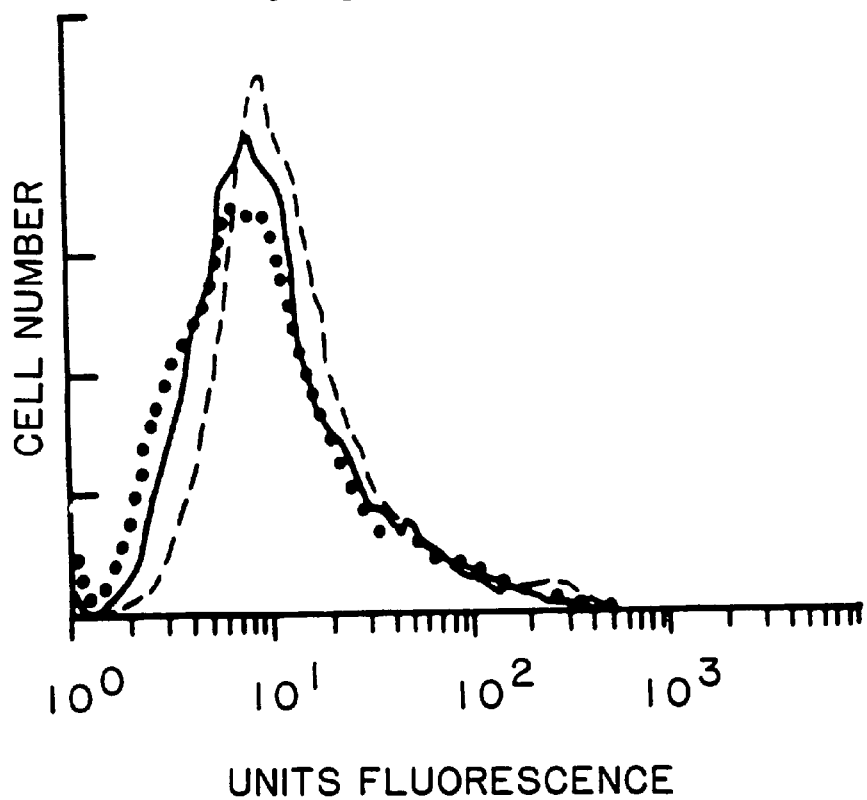
Figure 2I:
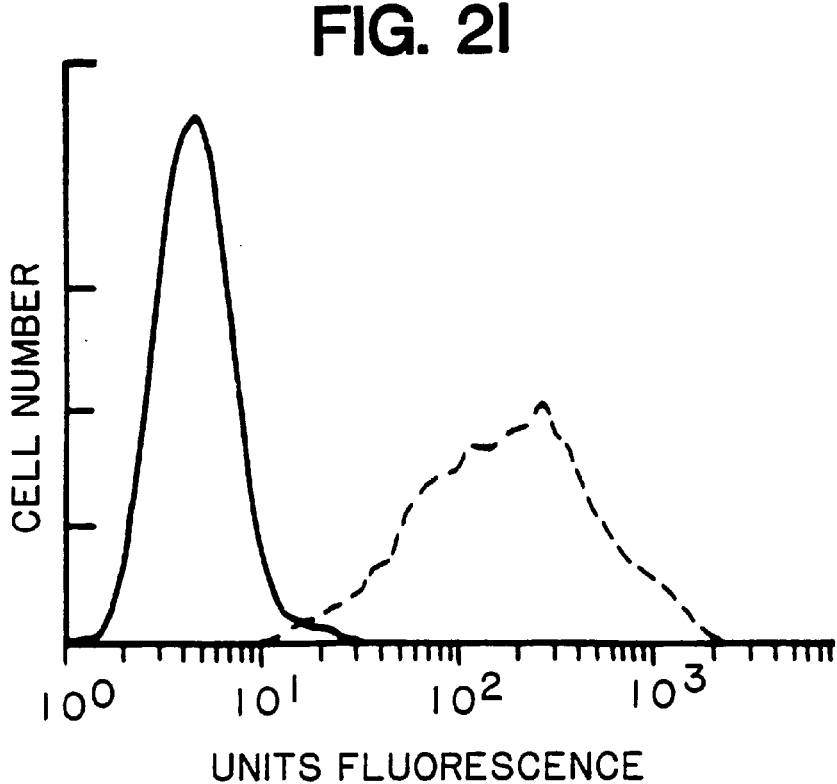
Figure 2J:
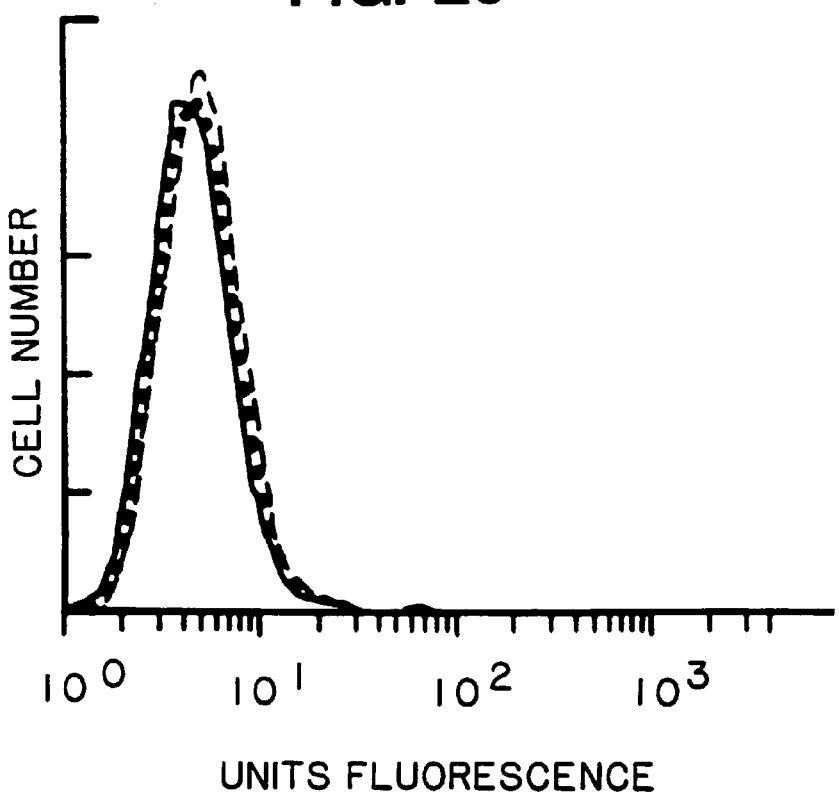
Figure 2K:
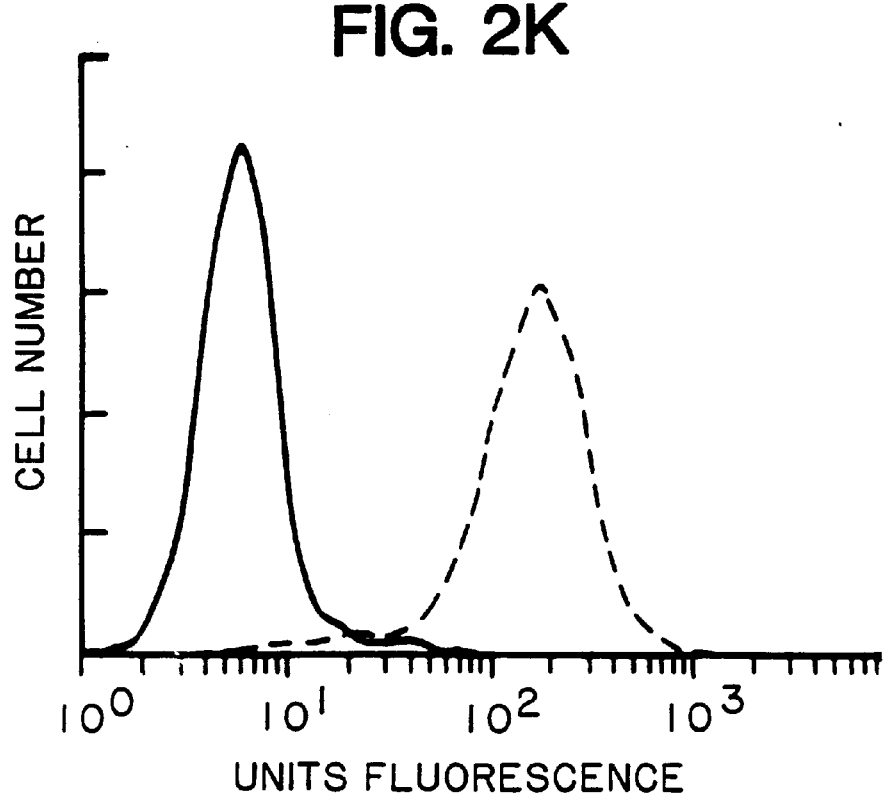
Figure 2L:
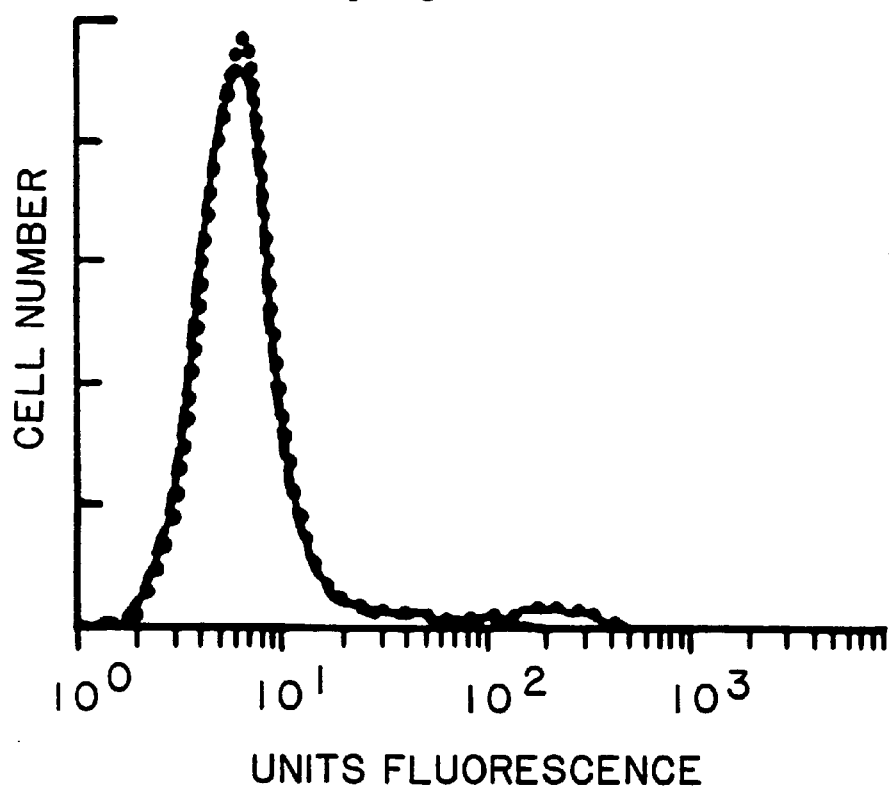
Figure 2M:
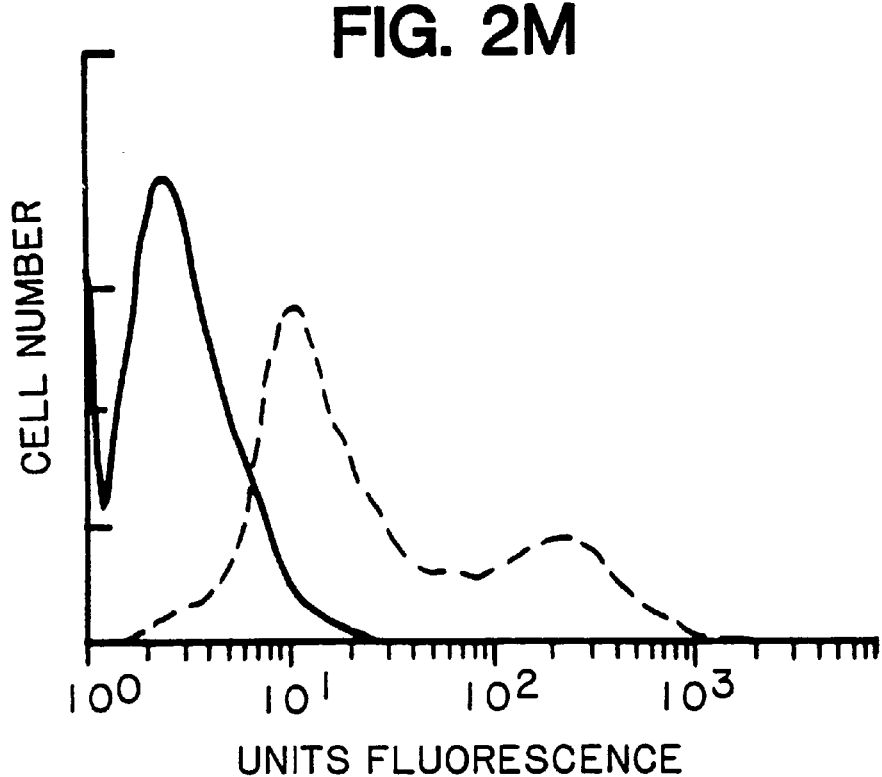
Figure 2N:
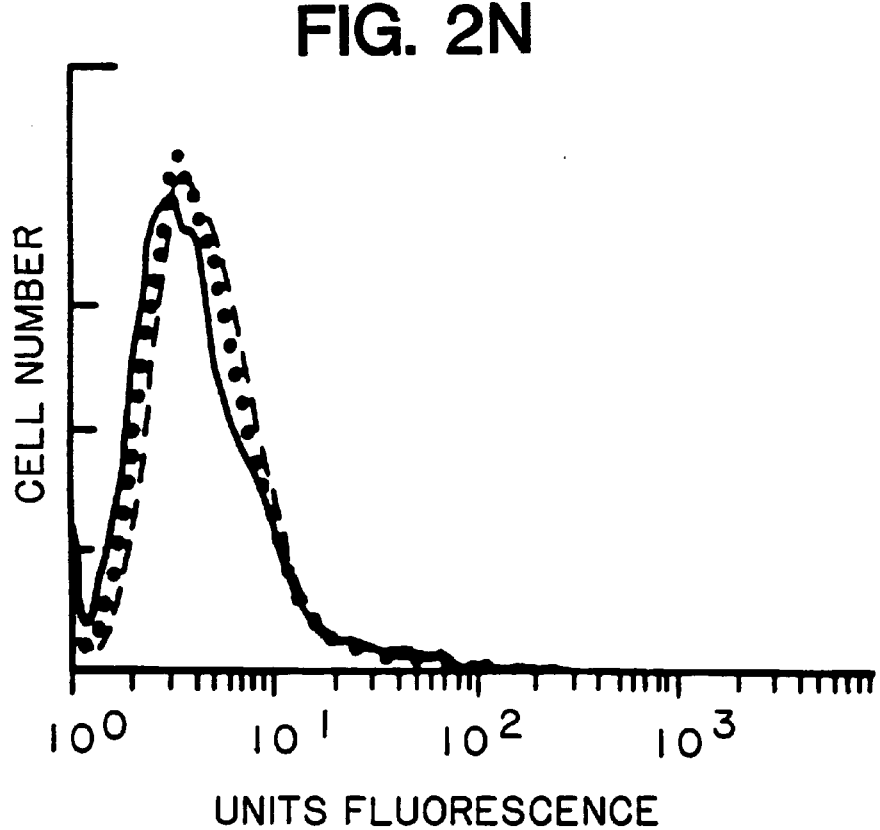

Referring to FIGS. 2A and 2B, the FACS analyses indicated that cells transfected with expression vectors containing deletion mutations M57 (FIGS. 2A and 2B), M65 (FIGS. 2C and 2D), M63 (FIGS. 2E and 2F), M54 (FIGS. 2G and 2H), M55 (FIGS. 2I and 2J), M56 (FIGS. 2K and 2L), and M58 (FIGS. 2M and 2N) expressed a surface protein that was recognized by the anti-LFA-3 polyclonal antiserum 202 (FIGS. 2A, 2C, 2E, 2G, 2I, 2K, 2M). However, the anti-LFA-3 MAbs TS2/9 and 7A6 bound only to transfectants carrying the M65 and M63 deletion mutants and not to transfectants lacking the M57, M54, M55, M56, or M58 regions (compare FIGS. 2B, 2H, 2J, 2L, 2N with 2D, 2F). These results indicated that the M54, M55, M56, M57 and M58 segments, which were deleted from the LFA-3 protein in, respectively, the deletion mutations M54, M55, M56, M57 and M58 (see FIGS. 1A-1, 1A-2 and 1B), were important in CD2 recognition of the LFA-3 molecule.

EXAMPLE 4
Jurkat Cell Binding Assay

CHO cells transfected with the M57 deletion mutation ("M57/CHO" cells), CHO cells transfected with plasmid p24 (see, Wallner et al., PCT patent application WO 90/02181) expressing PI-linked LFA-3 ("P24/CHO" cells, positive control), and normal CHO cells (negative control) were tested for the ability to bind Jurkat cells expressing CD2.

M57/CHO cells, P24/CHO cells and CHO cells ($1 \times 10^5$) were added to separate wells of a 6-well plate (Corning) and washed twice with RPMI Complete Medium. Jurkat cells (CD2$^+$), obtained as a gift from Dr. Timothy Springer (Dana Farber Cancer Inst., Boston, Mass.) were washed three times with a solution of RPMI, 10% FCS, 4 mM L-glutamine, and then $5 \times 10^6$ cells were added to each well and incubated for 4 hours at 0° C. Cells were then washed gently three times with RPMI and examined under the microscope at 40× and 100× magnification for cell-cell binding.

Figure 3A:
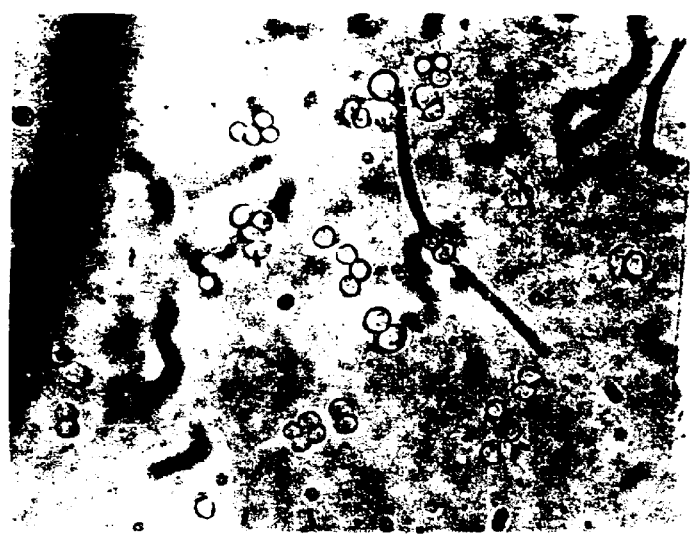
FIGS. 3A, 3B and 3C taken together depict the results of a Jurkat cell binding experiment. The photomicrographs show Jurkat cells expressing CD2 mixed with normal CHO cells (negative control) (FIG. 3A), M57/CHO cells (FIG. 3B) and P24/CHO cells expressing PI-linked LFA-3 (positive control) (FIG. 3C).
Figure 3B:
Figure 3C:
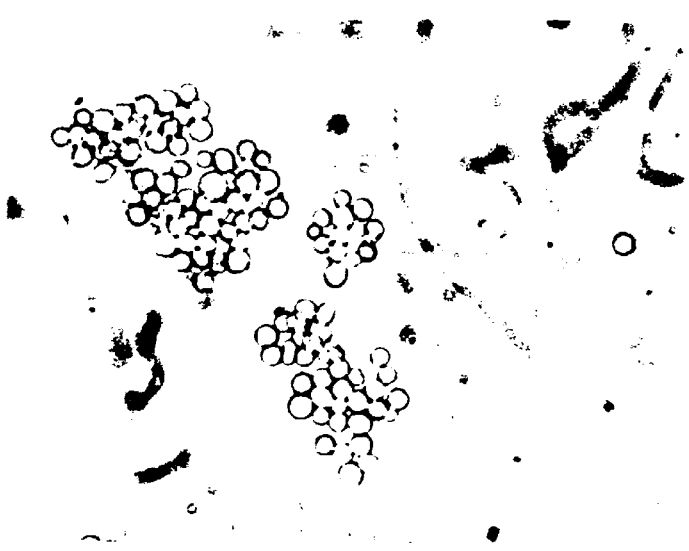

Referring to FIG. 3, whereas positive control cells expressing PI-linked LFA-3 bound Jurkat cells expressing CD2 (FIG. 3C), M57/CHO cells failed to bind Jurkat cells (FIG. 3B), as did nontransfected (LFA-3$^-$) CHO cells (FIG. 3A).

EXAMPLE 5
Northern Blot Analysis of mRNA from M57/CHO Cells

The mRNA of M57/CHO cells was analyzed by Northern blot as a further confirmation that the failure of the monoclonal antibodies, i.e., MAbs TS2/9 and 7A6, to bind to the M57/CHO cells was due to the surface LFA-3 mutant lacking the M57 CD2-binding region rather than to inefficient expression of the mutant LFA-3 gene.

RNA from about $1 \times 10^7$ M57/CHO cells on a 100 mm plate was isolated as follows: Growth media were removed and 2 ml extraction buffer (50 mM Tris-Cl (pH 7.5), 1% SDS, 5 mM EDTA, proteinase K added to 100 $\mu$g/ml immediately prior to use) was added. The plate was incubated 20 minutes at 37° C. with gentle shaking. A viscous cell lysate developed and was collected in a 50 ml test tube. An equal volume of phenol:chloroform:ether (50:50:1) was added and the mixture vortexed briefly. The mixture was homogenized on a Polytron mixer (Kinematica, Switzerland) for 15 seconds at highest speed to shear the DNA. The mixture was poured into a 15 ml Corex tube and centrifuged at 10,000 rpm, 10 minutes at 4° C.

After centrifuging, the aqueous phase was collected and NaCl was added to 0.25 M, followed by 1 volume of isopropanol. This mixture was placed on dry ice for 10 minutes, defrosted and centrifuged 15 minutes at 10,000 rpm and 4° C.

The pellet was resuspended in 2.9 ml distilled water and vortexed. 0.9 ml of 12 M LiCl was added (to 2.8 M) and the suspension allowed to stand at least four hours at 4° C. 5S RNA and DNA remained in solution; other RNA fractions precipitated. This solution was centrifuged for at least 15 minutes at 10,000 rpm at 4° C.

The pellet was resuspended in 360 µl distilled water and transferred to an Eppendorf tube. 40 µl 3 M NaAc (pH 5.2) and 1 ml ethanol were added, then the mixture was cooled at −70° C. for 5 minutes, cooled at −20° C. for 15 minutes, centrifuged, rinsed with ethanol, and resuspended in 400 µl 0.3 M NaAc. Ethanol (1 ml) was added and the precipitation was repeated. The RNA recovered after centrifuging was resuspended 100 µl distilled water.

Figure 4:
FIG. 4 depicts a Northern gel analysis of LFA-3 gene transcripts synthesized in M57/CHO cells. Filters containing mRNA samples from CHO negative control cells (lane 1), M57/CHO cells (lane 2) and M16.3/CHO positive control cells (lane 3) were probed with a NotI restriction fragment of plasmid pLFA3M54, containing nucleotides 1–153 and 184–1040 of the LFA-3 cDNA sequence (see FIGS. 1A-1, 1A-2 and 1B), labeled with $^{32}$P by nick-translation.
Figure 7A:
FIGS. 7A, 7B, 7C and 7D taken together show results of Jurkat cell-binding experiments in which Jurkat cells expressing CD2 were mixed with (a) normal CHO cells, (b) M100/CHO cells, (c) M101/CHO cells, or (d) M102/CHO cells.
Figure 7B:
Figure 7C:
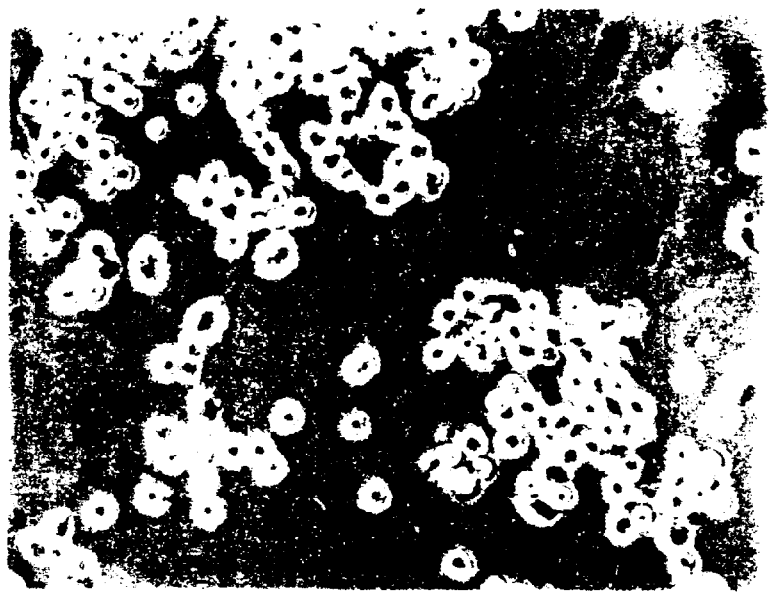
Figure 7D:

10 µg of the RNA were electrophoresed on a 1% agarose-formaldehyde gel, transferred to a GeneScreen nitrocellulose membrane (New England Nuclear) and hybridized to a $^{32}$P-labeled probe. As a control, RNA extracted from the cell line M16.3/CHO (expressing recombinant soluble LFA-3, obtained from Biogen, Inc., Cambridge, Mass.) was analyzed on the same Northern blot. The Northern blot analysis (FIG. 4) indicated efficient synthesis of the M57 RNA in the M57/CHO cells.

EXAMPLE 6

Immunoprecipitation of LFA-3 Deletion Mutant

To verify the loss of specific antibody binding domains in the mutant LFA-3 expressed on the surface of M57/CHO cells, M57/CHO transfectants, untransfected CHO cells, and P24/CHO transfectants (which express PI-linked LFA-3) were surface labeled with $^{125}$I, and each of the three primary antibody preparations (i.e., polyclonal antiserum 202, MAb TS2/9 and MAb 7A6) were used to immunoprecipitate LFA-3 after detergent disruption of the surface membrane.

About $10^7$ (each) of M57/CHO cells, normal CHO cells and P24/CHO cells suspended in PBS$^-$ (i.e., PBS without Ca$^{++}$ and Mg$^{++}$) supplemented with 5 mM EDTA were washed three times with PBS$^-$ and resuspended in 0.5 ml PBS. Washed cells were added to glass tubes (12×75 mm$^2$) previously coated with a solution of 50 µg 1,3,4,6-tetrachloro-3α,6α-diphenylglycoluril (Iodo-Gen, Pierce Bio-Research, Rockford, Ill.) in 100 µl CHCl$_3$ and dried in nitrogen. Just before use, the tubes were rinsed with PBS, and then $^{125}$Iodine (1 mCi) was added and the tubes incubated on ice for 30 minutes, with swirling every 10 minutes.

After incubation, the iodinated cells were added to 10 ml alpha$^-$ MEM, 10% FCS, 4 mM L-glutamine. The cells were spun down, washed twice with 5 ml of the same medium, and then resuspended in 1 ml PBS and centrifuged again. The washed cells were then lysed by resuspension in 1 ml DOC buffer (20 mM Tris/Cl, pH 7.3; 50 mM NaCl, 0.5% deoxycholate (DOC); 0.5% NP40) containing 20 µl of protease inhibitor PMSF (Sigma Chemical Co., St. Louis, Mo., 17 mg/ml in ethanol), followed by incubation for 30 minutes on ice. The lysate was then microcentrifuged for 10 minutes at 4° C., and the supernatants containing the $^{125}$I-labeled surface molecules removed.

Lysates from the foregoing iodinations were precleared by contacting with 50 µl of protein A-Sepharose and incubating on a rocker for 1 hour at room temperature. 100 µl of lysate was removed for each sample and mixed with 300 µl of DOC buffer. This mixture was centrifuged and the resulting cleared supernatant removed to a new tube.

Primary antibody was added to samples of each of the cleared supernatants: Polyclonal anti-LFA-3 antiserum 202 was used at a final concentration 40 µg/ml; MAbs TS2/9, 7A6 and a control monoclonal antibody, MOPC-21 (IgG1, not specific to LFA-3) were used at 5 µg/ml. 100 µl DOC and 2 µl protease inhibitor PMSF were added, and the mixtures incubated on a rocker for 2 hours at room temperature 25° C. or overnight at 4° C.

After incubation, 30 µl of protein A-Sepharose (for polyclonal antiserum 202 samples) or 15 µl of anti-mouse IgG-agarose (Sigma Chemical Co.) (for MAb samples) was added to the samples, followed by incubation on a rocker for 2 hours at room temperature. The mixtures were then centrifuged for 2 minutes, and the supernatants carefully removed and discarded. 1 ml of DOC buffer was then added, and the pellets resuspended by vortexing. The resuspended material was then washed 3 times with DOC buffer.

To prepare the samples for analysis by polyacrylamide gel electrophoresis, 30 µl of SDS sample buffer was added, the sample heated at 65° C. for 15 minutes. The sample was then centrifuged for 2 minutes, and the supernatant removed and saved for electrophoresis. 15 µl of the supernatant was run on a denaturing 10–20% gradient polyacrylamide gel (Daiichi system, Enprotech), and autoradiography performed to identify immunoprecipitated surface proteins.

FIG. 5 is an autoradiograph of an SDS polyacrylamide gel showing antibody-precipitated LFA-3 surface proteins from M57/CHO, normal CHO, and P24/CHO cells. This gel revealed that TS2/9, 7A6 and the polyclonal antiserum 202 precipitated LFA-3 from the CHO cells expressing the PI-linked LFA-3 (lanes 9, 10, 11). In contrast, only polyclonal antiserum 202 precipitated the LFA-3 surface protein from M57/CHO cells expressing the deletion mutant M57 LFA-3 gene (lane 4).

EXAMPLES 7 AND 8

The 10-amino acid region removed in the M57 deletion mutant (see FIGS. 1A-1, 1A-2 and 1B) is adjacent to but does not contain a N-linked glycosylation site. To investigate whether the region of the M57 deletion is involved directly in CD2-binding or indirectly disrupts CD2-binding by causing a conformational change in the CD2-binding domain of LFA-3, two additional experiments were performed.

First, three large deletion mutants were generated, each of which lacked a span of 59 amino acids compared to the native LFA-3 molecule. The regions deleted are shown by underlining in FIG. 6A-1, 6A-2 and 6B and were designated M100, M101 and M102. The object of this experiment was to determine whether the conformational changes inherent in the large M101 and M102 deletions would alter recognition of the M57 region (see FIGS. 1A-1, 1A-2 and 1B) and to demonstrate that the entire CD2 binding domain was encompassed in the M100 region.

Second, a synthetic oligopeptide, LF08, having the amino acid sequence (SEQ ID NO:7) Lys Asn Arg Val Tyr Leu Asp Thr Val Ser Gly Ser Leu Thr Ile Tyr (amino acids +50−+65 of mature LFA-3 (see FIGS. 1A-1, 1A-2, and 1B)) was isolated and fixed to a solid substrate, then used in a Jurkat cell resetting assay to determine if CD2-expressing cells would recognize the isolated M57 region of LFA-3 (see FIGS. 1A-1, 1A-2 and 1B).

Preparation of Large Deletion Mutants

FIGS. 6A-1, 6A-2 and 6B depict the amino acid sequence and nucleotide sequence of transmembrane LFA-3 and shows with underlining the three regions, designated M100, M101 and M102, which were deleted from LFA-3 cDNA to yield genes capable of directing the expression of three large deletion mutants.

Following the procedure used in Example 1, a 30-base antisense oligonucleotide was synthesized which consisted of sequences complementary to the 15 bases of the sense strand upstream of (5' to) and to the 15 bases downstream of (3' to) the desired deletion region. The synthetic oligonucleotides used to generate the large deletion mutations are shown below:

| Sequence | Complementary to LFA-3 Nucleotides | Segment Deleted |
| --- | --- | --- |
| SEQ ID NO:30 | 109–123 + 304–318 | M100 |
| SEQ ID NO:31 | 289–303 + 484–498 | M101 |
| SEQ ID NO:32 | 469–483 + 634–648 | M102. |

Heteroduplexing was carried out as described in Example 1, except that 200 ng of LFA-3 cDNA was used. Colony hybridizations were carried out using $1\times10^6$ CPM/ml $^{32}$P-ATP kinased oligonucleotides at 65° C. and washed with 0.5×SSC at 60° C. Positives were screened by EcoRI digestion and isolation of 2900 bp and 500 bp fragments on a 0.7% TAE agarose gel.

Construction of expression vectors was performed by excising the LFA-3 cDNA from deletion mutation plasmids prepared above with NotI. Aliquots of 50 μg of a eukaryotic expression plasmid PMDR902 (obtained from Biogen, Inc., Cambridge, Mass.) were digested with 50 units of NotI, and the isolated NotI fragments (0.06 pmol), containing the deletion mutations M100, M101 and M102, were ligated to 0.02 pmol PMDR902 DNA, and the ligated products were used to transform E.coli JA221.

Positive clones were screened by colony hybridization using oligonucleotides 18, 19 and 20, having the sequences of SEQ ID NO:30, SEQ ID NO:31 and SEQ ID NO:32, respectively, as probes. The orientation of the inserts was determined by PvuII restriction analysis, which generated bands of approximately 6599, 1737 and 500 bp on 20.7% TAE agarose gel for correctly oriented constructs. The sequence was confirmed by DNA sequencing as described above. The resulting recombinant expression plasmids containing the M100, M101 and M102 deletion mutations were designated pPMDRM100-4, pPMDRM101-1 and pPMDRM102-8, respectively. The resulting expression plasmids were electroporated into CHO cells as in Example 2, except the cells were split into medium containing 25 nM and 50 nM methotrexate.

The M100/CHO, M101/CHO and M102/CHO transfectants were subjected to a Jurkat cell binding assay, as described in Example 4 above. The results are shown in FIG. 7. M101/CHO cells (FIG. 7C) and M102/CHO cells (FIG. 7D), which express a surface protein having the intact M57 CD2-binding region of LFA-3, showed clumping characteristic of Jurkat/CHO cell binding. CHO control cells (FIG. 7A) and M100/CHO cells (FIG. 7B) showed no such clumping, indicating the absence of a surface structure on the CHO cell surface recognized by Jurkat cells.

Jurkat Binding to Immobilized LF08 Peptide 1.4 mg of the synthetic peptide LF08 (SEQ ID NO:7) or control hepatitis B peptide MXC-01 (SEQ ID NO:4) at 2 mg/ml in deionized water was coupled to 100 μl agarose gel beads (Affi-Gel 10, BioRad, Richmond, Calif.) according to the following protocol: 100 μl of Affi-Gel 10 slurry was transferred to a small Buchner funnel and the solvent drained. The beads were washed with three bed volumes of cold (4° C.) deionized water, transferred to 700 μl of the LF08 solution, and then incubated for 4 hours at 4° C. on a rocker. A spectrum taken of the supernatant, before and after coupling of LF08, indicated that a coupling efficiency of 80% had been achieved.

After coupling, unreacted coupling sites were blocked by incubating the LF08 beads or MXC-01 beads with ethanolamine/HCl (93 mN, pH 7.9) overnight at 4° C. with gentle shaking. The blocked beads were then washed three times with PBS supplemented with 0.5 M NaCl and three times with PBS supplemented with 10% FCS.

Figure 8A:
FIGS. 8A, 8B and 8C taken together show Jurkat cell binding by LF08/AffiGel-10 beads (see Example 8, infra). LF08/AffiGel-10 beads were mixed with Jurkat cells and the cell-bead binding observed under a microscope (FIGS. 8A and 8B). For comparison (negative control), a non-LFA-3 peptide from hepatitis B (i.e., "MXC 01", (SEQ ID NO:4) Thr Lys Pro Asp Leu Val Asp Lys Gly Thr Glu Asp Lys Val Val Asp Val Val Arg Asn) was fixed to Affigel-10 beads, the beads mixed with Jurkat cells, and cell-bead binding recorded in FIG. 8C.
Figure 8B:
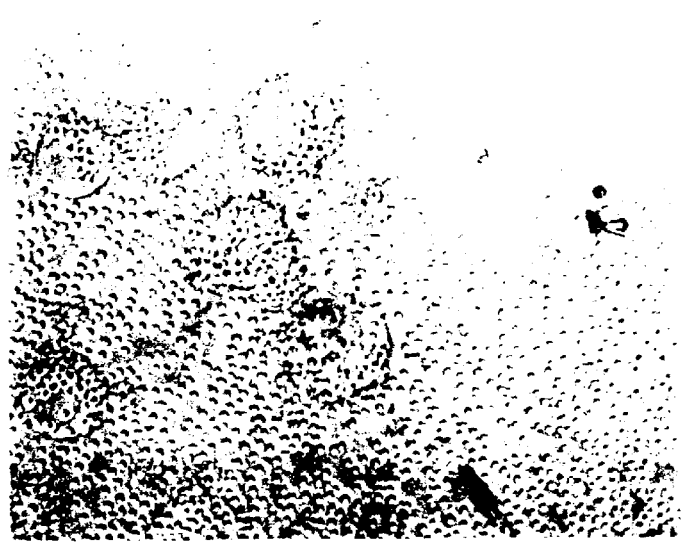
Figure 8C:

Jurkat cells ($2\times10^5$) were washed twice with RPMI, 4 mM L-glutamine, 10% PBS and combined with 2.5 or 15 μl of LF08/Affi-Gel 10 beads or MXC-01/Affi-Gel 10 beads to a final volume of 20 μl. The mixture was incubated for 30 or 60 minutes at room temperature. After incubation, the cells were transferred to 200 μl RPMI in a 96-well flat bottom plate (Corning), and observed under a microscope at 40× and 100×. FIGS. 8A and 8B show characteristic results of contacting the LF08/Affigel beads with Jurkat cells, resulting in binding of coated beads to the surface of Jurkat cells. FIG. 8C shows characteristic results of the MXC-01/Affigel beads failing to bind to the surface of Jurkat cells.

EXAMPLES 9 AND 10

A further deletion mutant was prepared which provided a PI-linked surface polypeptide on CHO cells having the N-terminal 89 amino acids of native LFA-3. Referring to FIGS. 9A and 9B, the nucleotides deleted from cDNA encoding PI-linked LFA-3 are shown by the underlined region, PIM3. The PIM3 nucleotides were deleted using the same heteroduplex deletion mutagenesis strategy described above (Example 1). In this case, a 30-base antisense oligonucleotide (oligonucleotide 320.03), having the 5'-3' sequence (SEQ ID NO:8) TAATGGATTG CTAAGAAAGA ACTTCATGGT, was used for deletion mutagenesis.

Plasmid p24 (100 ng), containing the cDNA encoding PI-linked LFA-3 was digested with NotI, and the large restriction fragment (lacking the PI-linked LFA-3 coding sequence) was isolated. Additional p24 DNA was linearized with ScaI. The large NotI restriction fragment and the ScaI-linearized DNA were denatured, mixed with oligonucleotide 320.03, and allowed to reanneal as described in Example 1. After annealing, the gaps in the heteroduplexes were filled in, and the fragments ligated as described in Example 1.

The filled-in, ligated heteroduplexes were then transformed into E.coli JA221 and the transformants screened by colony hybridization using a $^{32}$P-labeled 320.03 oligonucleotide ($1\times10^6$ cpm/ml) at 60° C. as described above. The hybridization filters were washed in 0.5× SSC at 65° C. and positive colonies identified by autoradiography. Plasmid DNA was isolated from each of the positive colonies, and digested with NotI. Digestion of one of the plasmids, pPIM3-6, with NotI yielded fragments of 2648 and 640 bp, confirming that pPIM3-6 contained the desired PIM3 deletion in the PI-linked LFA-3 coding sequence.

The 640 bp NotI fragment of pPIM3-6 was cloned into the NotI site of the expression vector PMDR902 (a gift of Dr. M. D. Rosa, Biogen, Inc., Cambridge, Mass.) and used to transform E.coli JA221 cells. Transformants were screened by colony hybridization using the $^{32}$P-labeled 320.03 oligonucleotide as probe. Plasmids from positive colonies were then isolated, and the orientation of the DNA insert determined by restriction enzyme analysis using PvuII. Recombinant plasmid pPMDRM3-10 contained PvuII fragments of 6399, 1634 and 495 bp, indicating that this plasmid contained the mutated PI-linked LFA-3 gene in the proper orientation for expression in the PMDR902 vector.

Expression of PIM3 Deletion Mutant pPMDRM3-10 was electroporated into CHO DHFR$^-$ cells and amplified with 25 and 50 nM methotrexate as described above. Cells from plates containing confluent growth were assayed by FACS using MAbs TS2/9 and 7A6 as described above. The PIM3 deletion mutant form of LFA-3 expressed in a cell line designated PIM3.25.2 exhibited epitopes involved with CD2/LFA-3 complex formation.

To determine whether the protein recognized by TS2/9 and 7A6 on PIM3.25.2 cells was PI-linked, the protein expressed on the surface of PIM3.25.2 cells was tested for its susceptibility to release by treatment with phosphatidylinositol-specific phospholipase C (PI-PLC, obtained from Biogen, Inc.). Cells of PIM3.25.2 were grown to 70 percent confluency in two 100 mm culture plates and removed with PBS supplemented with EDTA (5 mM) as described above. One-third of these cells was treated with PI-PLC (1 µl; Biogen, Inc.) at 37° C. for 45 minutes in 100 µl of alpha$^-$ MEM supplemented with 10% FCS, L-glutamine (2 mM), pen-strep mix (1X), and 25 nM methotrexate. The cells were then centrifuged for 15 seconds in an Eppendorf microcentrifuge and washed two times in FACS buffer (PBS, 0.5% BSA, 0.1% sodium azide, pH 7.2). The washed cells were then resuspended in FACS buffer containing FITC-labeled goat anti-mouse IgG (1:50 dilution from serum). The cells were then washed twice with FACS buffer, resuspended in 300 µl of PBS and transferred to Falcon 2052 tubes for FACS analysis.

Figure 10A:
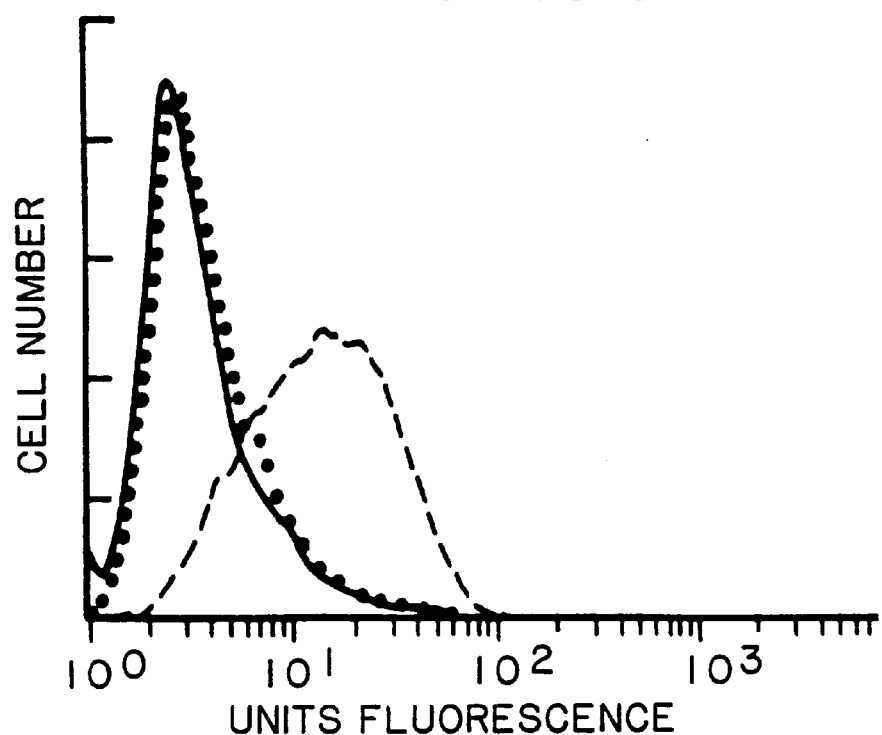
FIGS. 10A and 10B taken together depict results of immunofluorescence flow cytometry by FACS analysis of transfected CHO cells expressing a mutant form of PI-linked LFA-3 encoded by deletion mutation PIM3. Transfected cells (PIM3.25.2 cells) expressed a surface protein that was recognized by anti-LFA-3 MAb TS2/9 (FIG. 10A, dashed line) and that was susceptible to release from the cell surface by PI-PLC treatment (FIG. 10A, dotted line).
Figure 10B:
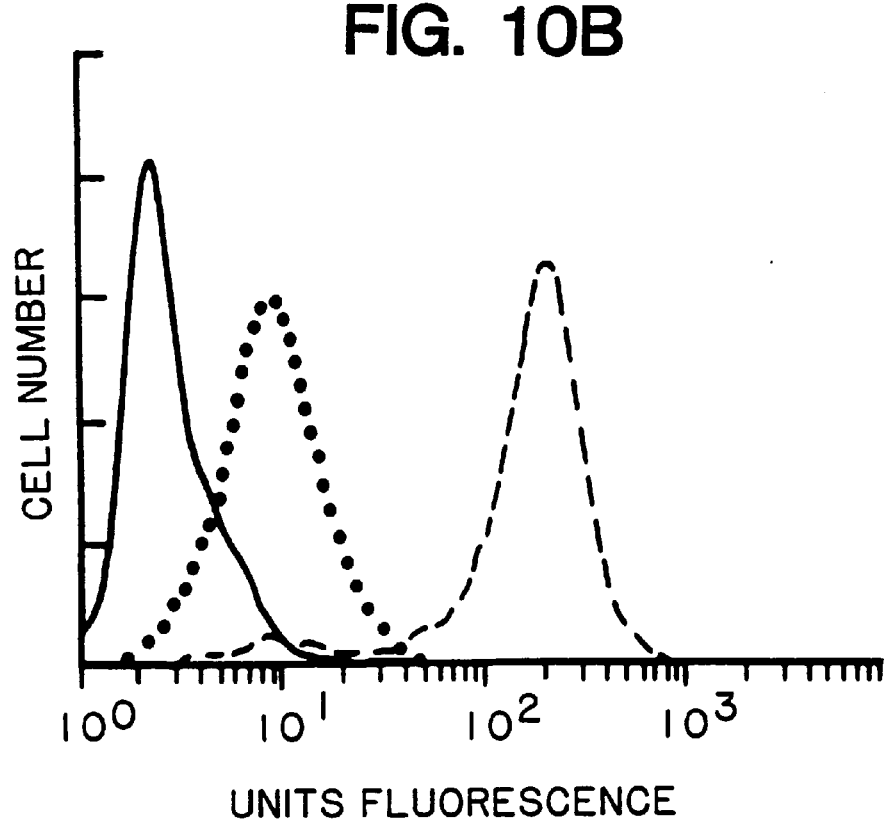

Referring to FIGS. 10A and 10B, cells of PIM3.25.2 clearly express a protein on their cell surface that is recognized by TS2/9 (FIG. 10A, dashed line) and is also susceptible to release from the cell surface by PI-PLC treatment (FIG. 10A, dotted line). Since the PIM3 protein expressed in cells of clone PIM3.25.2 possesses LFA-3 epitopes recognized by MAb TS2/9, which blocks CD2/LFA-3 complex formation, it was concluded that the 89 amino acid N-terminal region of the mature LFA-3 molecule contains the conformational requirements necessary for CD2/LFA-3 complex formation.

To increase expression of the PIM3 mutant LFA-3 protein, the PIM3.25.2 clone was amplified in alpha$^-$ MEM supplemented with 10% FCS in 50, 100 and 200 nM of methotrexate. Cells were plated in 96-well microtiter plates at a concentration of 20 cells/ml, grown to confluency (12–17 days) and expanded to 100 mm plates for subsequent FACS analysis as described for PIM3.25.2, except that expression of the PIM3 mutant form of LFA-3 was monitored using the 7A6 MAb (FIG. 10B, dashed line). The results of the FACS analysis indicated that the amplified cell line, PIM3.25.2.100.12, expressed approximately ten-fold higher amounts of the PIM3 mutant form of PI-linked LFA-3. Treatment of the PIM3.25.2.100.12 cells with PI-PLC released about 80% of the PIM3 mutant LFA-3 (FIG. 10B, dotted line).

EXAMPLE 11

Construction of Plasmid pSAB144 pSAB144 contains the human IgG1 constant region sequences excluding the $C_H1$ region and the first cysteine of the amino terminal portion of the hinge region. The human IgG1 heavy chain constant region was isolated from a partial Sau3A human fibroblast genomic library (EMBL/5X, a gift of Dr. Mark Pasek). The library DNA was cleaved with HindIII and PvuII. DNA fragments corresponding to approximately 3 kb were ligated to the vector fragment of pSP65 (Promega, Madison, Wis.) generated by cleavage of pSP65 using HindIII and HincII. The resulting plasmid was designated pAB1. Plasmid pAB1 was used as a source of DNA encoding the IgG1 heavy chain constant region.

In order to isolate a cDNA copy of the IgG1 heavy chain region, RNA was prepared from COS7 cells which had been transiently tranfected by the plasmid VCAM1-IgG1 (also known as pSAB133). Construction of plasmid VCAM1-IgG1 is described in PCT patent application WO 90/13300. The RNA was reverse transcribed to generate cDNA using reverse transcriptase and random hexamers as the primers. After 30 min. at 42° C., the reverse transcriptase reaction was terminated by incubation of the reaction at 95° C. for 5 min. The cDNA was then amplified by PCR (Polymerase Chain Reaction, see, e.g., Sambrook et al., *Molecular Cloning*, Vol. 3, pp. 14.1–14.35 (Cold Spring Harbor; 1989)) using the following kinased primers:

370-31:
(SEQ ID NO:34): 5'TCGTC GAC AAA ACT CAC ACA TGC C,
(SEQ ID NO:35) asp lys thr his thr cys
which contains a SalI site, and 370-32 (SEQ ID NO:36):
5' GTAAATGAGT GCGGCGGCCG CCAA,
which encodes the carboxy terminal lysine of the IgG1 heavy chain constant region, followed by a NotI site.

The PCR amplified cDNA was purified by agarose gel electrophoresis and glass bead elution for cloning in plasmid pNN03. Plasmid pNN03 was constructed by removing the synthetic polylinker sequence from the commercially available plasmid pUC8 (Pharmacia, Piscataway, N.J.) by restriction endonuclease digestion and replacing the synthetic polylinker sequence with the following novel synthetic sequence (SEQ ID NO:37):

GCGGCCGCGG TCCAACCACC AATCTCAAAG CTTGGTACCC GGGAATTCAG ATCTGCAGCA TGCTCGAGCT CTAGATATCG ATTCCATGGA TCCTCACATC CCAATCCGCG GCCGC.

The purified PCR amplified cDNA fragment was ligated to pNN03 which had been cleaved with EcoRV, dephosphorylated, and purified by low melt agarose gel electrophoresis. The ligation reaction was used to transform *E.coli* JA221 and the resulting colonies were screened for a plasmid containing an insert of approximately 700 bp. The identity of the correct insert was confirmed by DNA sequence analysis, and the plasmid was designated pSAB144.

Construction of Plasmid pSAB149

The plasmid pSAB149 was constructed as follows. The LFA3-encoding plasmid pHT16-6 was subjected to PCR amplification using oligonucleotides 320-04 and 320-05. oligonucleotide 320-04 includes a NotI site and the nucleotides corresponding to amino acids 1 through 7 of the LFA-3 signal sequence:

(SEQ ID NO:38) 5' GAGGCGGCCG CC ATG GTT GCT GGG AGC GAC GCG, (SEQ ID NO:39) met val ala gly ser asp ala.

Oligonucleotide 320-05 corresponds to the LFA-3 amino acids 86–92 and includes a SalI site (SEQ ID NO:40): 5' AAGTCGACAT AAAGAAAGAA CTTCAT. The amplified DNA fragment was ligated to the vector fragment of pNN03, cleaved by EcoRV.

Construction of pSAB132 pJOD-S (Barsoum, J., *DNA and Cell Biol.*, 9, pp. 293–300 (1990)) was modified to insert a unique NotI site downstream from the adenovirus major late promoter so that NotI fragments could be inserted into the expression vector. pJOD-S was linearized by NotI cleavage of the plasmid DNA. The protruding 5' termini were blunt-ended using Mung Bean nuclease, and the linearized DNA fragment was purified by low melting temperature agarose gel electrophoresis. The DNA fragment was religated using T4 DNA ligase. The ligated molecules were then transformed into *E.coli* JA221. Colonies were screened for the absence of a NotI site. The resulting vector was designated pJOD-S delta NotI. pJOD-8 delta Not1 was linearized using SalI and the 5' termini were dephosphorylated using calf alkaline phosphatase. The linearized DNA fragment was purified by low melting temperature agarose gel electrophoresis and ligated in the presence of phosphorylated oligonucleotide ACE175, which has the following sequence: (SEQ ID NO:41) TCGACGCGGC CGCG. The ligation mixture was transformed into *E.coli* JA221, and colonies were screened for the presence of a plasmid having a NotI site. The desired plasmid was named pMDR901.

In order to delete the two SV40 enhancer repeats in the SV40 promoter which controls transcription of the DHFR cDNA, pMDR901 and pJODΔe-tPA (Barsoum, *DNA and Cell Biol.*, 9, pp. 293–300 (1990)) were both cleaved with AatII and DraIII. The 2578 bp AatII-DraIII fragment from pMDR901 and the 5424 bp AatII-DraIII fragment from pJODΔe-tPA were isolated by low melting temperature agarose gel electrophoresis and ligated together. Following transformation into *E.coli* JA221, the resulting plasmid, pMDR902, was isolated. pSAB132 was then formed by eliminating the EcoRI-NotI fragment of pMDR902 containing the adenovirus major late promoter and replacing it with an 839 bp EcoRI-NotI fragment from plasmid pCMV-B (Clontech, Palo Alto, Calif.) containing the human cytomegalovirus immediate early promoter and enhancer.

Construction of pSAB152 pSAB144 was cleaved with SalI and NotI, and the 693 bp fragment isolated. pSAB149 was cleaved with SalI and NotI and the 365 bp fragment was isolated. The two fragments were ligated to pSAB132, which had been cleaved with NotI, and the 5' termini dephosphorylated by calf alkaline phosphatase. The resulting plasmid, pSAB152, contained the DNA sequence encoding the LFA-3 signal sequence, the amino terminal 92 amino acids of mature LFA-3, ten amino acids of the hinge region of IgG1 and the $C_H2$ and $C_H3$ constant domains of IgG1 (see FIG. 12). *E.coli* JA221 transformed with pSAB152 is deposited with American Type Culture Collection, Rockville, Md. (accession no. 68720).

Construction of pNNM57-14

As mentioned in Example 1, plasmid pLFA3M57-4A contains a DNA sequence encoding LFA-3 with a deletion of the 30 bp M57 region (i.e., nucleotides 244–273 of SEQ ID NO:9). This coding sequence of pLFA3M57-4A was subjected to PCR amplification using oligonucleotide 320-04 (SEQ ID NO:38) and oligonucleotide 320-05 (SEQ ID NO:40) in order to amplify the DNA encoding the signal sequence and the first 82 amino acids of the M57 deletion mutant of LFA-3. The PCR amplified DNA was purified by low melting temperature agarose gel electrophoresis.

The purified, PCR amplified DNA was then ligated into the EcoRV site of plasmid pNN03. The ligated DNA was transformed into *E.coli* JA221, and the resulting transformants screened (by NotI digestion) for a plasmid containing an approximately 300 bp insert. The identity of the desired insert was confirmed by DNA sequence analysis. The desired plasmid containing the approximately 300 bp insert was designated pNNM57-14.

Construction of pM57Ig-5

Plasmid pNNM57-14 was cleaved with NotI and SalI, and the 310 bp fragment isolated by low melting temperature agarose gel electrophoresis. This fragment and the 693 bp SalI-NotI fragment of pSAB144 (see supra) were ligated to NotI-digested, calf alkaline phosphatase-treated pSAB132 (see supra). The ligation mixture was used to transform *E.coli* JA221, and transformant colonies were screened by hybridization using a $\tau$-$^{32}$P-ATP labeled oligonucleotide having the sequence of SEQ ID NO:17. The desired orientation of the inserts in pSAB132 was confirmed by the identification of a 6913 and a 2029 bp fragment upon digestion with PvuII. The resulting plasmid was designated pM57Ig-5. DNA sequence analysis confirmed that pM57Ig-5 contains a DNA sequence encoding the LFA-3 signal sequence, the first 82 amino acids of the M57 deletion mutant of LFA-3, ten amino acids of the hinge region of human IgG1 and the $C_H2$ and $C_H3$ constant domains of IgG1.

EXAMPLE 12

Production of LFA3TIP From Transiently Transfected COS7 Cells

To produce the LFA-3-Ig fusion protein, LFA3TIP (also referred to as LFA-3(92)IgG), plasmid pSAB152 DNA was transfected into COS7 cells by electroporation as follows. Four aliquots of 200 μg each of pSAB152 DNA each were ethanol precipitated with 350 μg of sonicated salmon sperm DNA. DNA was pelleted and resuspended in 0.8 ml of 1xHEBS (20 mM Hepes/pH 7.05, 137 mM NaCl, 5 mN KCl, 0.7 mM $Na_2HPO_4$, 6 mM dextrose). COS7 cells from 4 confluent T150 flasks (8×10$^7$ cells) were removed by trypsin treatment in DMEM (Gibco, Gaithersburg, Md.), 10% fetal bovine serum, 4 mM glutamine. Cells from each flask were transferred to individual 15 ml Corning polypropylene tubes and pelleted at 1000 rpm for 4 minutes at room temperature in an IEC centrifuge. Medium was aspirated, and cells resuspended in the DNA-HEBS solution and transferred to a Bio-Rad (Richmond, Calif.) electroporation cuvette. The cuvettes were set in a Bio-Rad Gene Pulser and pulsed at 280 volts and 960 μFd capacitance. Cells were resuspended in 10 ml of DMEM medium and pelleted in an IEC centrifuge as described above. All cells were seeded into a 2 liter cell factory in DMEM medium, and culture medium was harvested after 72 hours for purification of LFA3TIP protein.

The concentration of secreted LFA3TIP in transfected COS7 culture medium was determined by ELISA. Fisher 96 flat bottom well plates (Corning 2580) were coated with 50 μl of goat anti-human IgG (H+L) (Jackson Immuno Research, West Grove, Pa., Catalogue No. 109-005-088) diluted at 5 μg/ml in 1xPBS. These plates were incubated at 4° C. overnight. Plates were washed the next day 6 times with d$H_2$O and blocked with 150 μl/well of block buffer (2% normal goat serum in 1xPBS). Buffer was removed after a 2 hour incubation at room temperature and conditioned medium was added at various dilutions. As a control to create a standard curve, a series of dilutions of whole human IgG (Jackson Immuno Research, West Grove, Pa., Catalogue No. 099-000-603) was included on the same plate. After a one hour incubation at room temperature, plates were washed 4 times with 0.01% Tween 20 in 1xPBS, and 50 μl/well of a 1:5000 serum dilution of alkaline phosphatase-conjugated anti-human IgG specific for Fc fragment (Jackson Immuno Research, West Grove, Pa., Catalogue No. 109-055-098) was added to each well. After one hour, plates were washed 6 times with 0.1% Tween 20.

Plates were developed with a solution containing a 1:10 dilution of 10 mM $Ca^{2+}$, $Mg^{2+}$ in 10% diethanolamine, pH 9.6, plus 5 mg/ml 4-nitrophenylphosphate (Boehringer Mannheim Biochemicals, Indianapolis, Ind., catalogue no. 738-352). The reaction was stopped using 3 N NaOH and plates read at 405 nM on a Microdevices microplate reader.

Production of LFA3TIP from a Stably Transformed CHO Cell Line

A recombinant LFA3TIP expression vector was constructed as described below, which can be stably maintained in CHO cells to achieve continuous expression of LFA3TIP.

A NotI fragment containing the LFA3TIP coding sequence of pSAB152 was purified by low melting temperature agarose gel electrophoresis. The fragment was ligated into the NotI cloning site of the expression plasmid pMDR902 (see Example 11). The resulting ligations were used to transform *E.coli* JA221, and colonies containing the desired, correctly oriented, insert were identified by the presence of 6599, 2058, and 487 bp fragments upon digestion with PvuII. The identity of the correct insert in pMDR902 was confirmed by DNA sequence analysis. The resulting recombinant expression plasmid was designated pMDR(92)Ig-3.

The recombinant expression plasmid pMDR(92)Ig-3 was electroporated into CHO cells according to the published protocol of J. Barsoum (*DNA Cell Biol.*, 9, pp. 293–300 (1990)), with the following changes. 50 μg of AatII-digested plasmid DNA and 350 μg of sonicated salmon sperm DNA were used in the electroporation protocol. In addition, cells were selected in alpha⁻ complete medium supplemented with 25 or 50 nM methotrexate (MTX).

To determine expression levels of secreted LFA3TIP, clones were transferred to a flat bottom 96 well microtiter plate, grown to confluency and assayed by ELISA (see infra). One clone grown in the presence of 25 nM MTX, LFA3TIP.25.11, expressed 5–10 μg of LFA3TIP per ml of culture medium. This clone was expanded and amplified further. Amplification was carried out by seeding 1 cell per well in a F96 well plate with complete medium supplemented with 50 or 100 nM MTX. Clones were grown to confluency and assayed by ELISA. Two clones, LFA3TIP.25.11.50.10A and LFA3TIP.25.11.50.5B, secreted higher levels (i.e., 50–60 μg of LFA3TIP per ml of culture medium) of LFA3TIP and were expanded for further study and purification.

The concentration of secreted LFA3TIP in medium of cultures of CHO cells carrying pMDR(92)Ig-3 (i.e., conditioned medium) was determined by ELISA.

Wells of Immulon 2 plates (Dynatech, Chantilly, Va.) were each coated with anti-LFA3 MAb TS2/9 (gift of Dr. Timothy Springer) with 50 μl of anti-LFA3 TS2/9 MAb diluted to 25 μg/ml in 0.05 M sodium carbonate/bicarbonate buffer, pH 9.6, covered with Parafilm, and incubated overnight at room temperature. The next day, plates were washed 6 times with deionized water and blocked with 150 μl/well of a block buffer (5% fetal calf serum in 1×PBS), which had been filtered through a 2 micron filter. The buffer was removed after a 2 hour incubation at room temperature, and conditioned medium was added at various dilutions. As a control to create a standard curve, a series of dilutions of LFA-3 (50 μl per well) was also included. Typically, the well containing the most concentrated LPA-3 standard contained 50 μl of an LFA-3 solution containing 10 ng of LFA-3 in 1×PBS. Block buffer diluted in 1×PBS constituted the negative control. The samples and controls were incubated at room temperature for one hour.

The plates were then washed 6 times with deionized water. Each well was then filled with 50 μl of a 1:5000 dilution of rabbit polyclonal anti-LFA-3 antiserum (e.g., antiserum 202, supra) in 5% fetal calf serum in 1×PBS. After one hour at room temperature, the polyclonal anti-LFA-3 antiserum was removed and the wells were washed 4 times with a solution of 0.05% Tween-20 in 1×PBS. Each well was then filled with 50 μl of HRP-goat anti-rabbit IgG(H+L) (Jackson Immuno Research Laboratories, Inc., West Grove, Pa.; Catalogue No. 111-035-045) at a 1:10,000 dilution in the block buffer containing 2% whole mouse serum (Cappel, Catalogue No. 5011-1380). The plates were then incubated at room temperature for 50–60 minutes.

The HRP-goat anti-rabbit IgG(H+L) solution was removed, and the wells were washed 6 times with 0.05% Tween-20 in 1×PBS. Then, 50 μl of HRP-substrate buffer was added to each well at room temperature. HRP-substrate buffer was prepared as follows: 0.5 ml of 42 mM 3,3',5,5'-tetramethylbenzidine (TMB), (ICN Immunobiologicals, Lisle, S.C., Catalogue No. 980501) in DMSO (Aldrich) was slowly added to 50 ml of substrate buffer (0.1 M sodium acetate/citric acid, pH 4.9); followed by addition of 7.3 μl of 30% hydrogen peroxide (Sigma, Catalogue No. H-1009).

The development of a blue color in each well was monitored at 650 nm on a microtiter plate reader. After 7–10 minutes, the development was stopped by the addition of 50 μl of 2 N sulfuric acid. The resulting yellow color was read at 450 nm on a microtiter plate reader. A negative control well was used to blank the machine.

Production of M57IgG

A fusion protein consisting of LFA3TIP lacking the ten amino acid M57 region of LFA-3 (M57IgG) was produced substantially as described above for LFA3TIP.

EXAMPLE 13

Purification of LFA3TIP

The COS7(pSAB152) conditioned culture medium was concentrated 10-fold using an AMICON S1Y30 spiral cartridge system (AMICON, Danvers, Mass.). The concentrate was divided into 4×50 ml aliquots and batch-adsorbed with 200 μl per aliquot of Protein-A Sepharose 4B (SIGMA, St. Louis, Mo.) overnight at 4° C. The beads were pelleted at 1000 rpm in a clinical centrifuge, combined, and then packed into a 5 mm diameter column. The resin was washed with 20 ml of PBS supplemented with 500 mM NaCl followed by 20 ml of PBS. The bound proteins were eluted in 150 μl fractions with 50 mM glycine, 250 mM NaCl (pH 3.0) into tubes containing 15 μl of 1 M HEPES, pH 7.8. 10 μl of each fraction was run on 12% nonreducing SDS-PAGE gels. The fractions containing the eluted protein were pooled and subjected to Superose-12 gel filtration chromatography developed in PBS (Pharmacia/LKB, Piscataway, N.J.).

Aliquots of 10 μl of the peak protein fractions (determined by measuring the O.D. at 280 nm) were run on 12% SDS-PAGE gels under nonreducing conditions and the fractions containing LFA3TIP with a low concentration of contaminating proteins, as determined on the SDS-PAGE gels and by Western blot analysis (see, e.g., Towbin et al., *Proc. Natl. Acad. Sci. USA*, 74, pp. 4350–54 (1979); *Antibodies: A Laboratory Manual*, pp. 474–510 (Cold Spring Harbor Laboratory, 1988)), were pooled and concentrated in a YM30 Centricon (AMICON, Danvers, Mass.). LFA-3 was detected on Western blots using rabbit anti-LFA-3 polyclonal antiserum 202 (see Example 3, supra) and goat anti-rabbit IgG, which was labeled with horseradish peroxidase (Sigma, St. Louis, Mo.). Blots were developed using the Amersham ECL detection kit (RPN 2106, Amersham, Arlington Heights, Ill.). The final pool was run on 12% SDS-PAGE gels under nonreducing conditions to assess the purity. A UV absorbance spectrum was run to determine the concentration. All preparations purified with Protein A were found to contain a single contaminant, which most likely is bovine IgG, present in the fetal calf serum of the culture medium, and which copurifies with the LFA3TIP.

The purity of LFA3TIP was determined by denaturing and nondenaturing SDS-PAGE (FIG. 13). The results of the SDS-PAGE analysis indicated that LFA3TIP, purified from the culture medium of COS7 cells carrying plasmid pSAB152, is present in the cell culture medium as a dimer of two monomeric LFA-3-Ig fusion proteins, connected by disulfide bonds.

The fact that LFA3TIP is found in the cell culture medium suggests that, as with LFA-3, the signal peptide sequence operates normally, i.e., the signal peptide is cleaved from the amino terminal region of the LFA-3 domain of LFA3TIP in the process of secreting LFA3TIP protein across the cell membrane.

Purification of M57IgG

M57IgG was purified from conditioned culture medium substantially as described above for LPA3TIP. Similar contaminants were observed.

EXAMPLE 14

FACS Analysis of LFA3TIP Binding

Jurkat cells were transferred into several Eppendorf tubes at $1 \times 10^5$ cells/tube. Cells were pelleted for 10 seconds in an Eppendorf microcentrifuge, the medium was aspirated off, and pellets were resuspended in 100 μl of LFA3TIP or anti-CD2 monoclonal antibody (MAb) TS2/18 (Sanchez-Madrid et al., *Proc. Natl. Acad. Sci. USA*, 79, pp. 7489–7493 (1982)), both at 10 μg/ml in FACS buffer (PBS, 0.1% $NaN_3$, 0.5% BSA pH 7.2). Cells were incubated on ice for 30 minutes, washed twice with FACS buffer, and incubated with 100 μl of the appropriate secondary antibody to detect MAbs bound to the Jurkat cells. FITC conjugated goat anti-mouse IgG (H+L) F(ab')$_2$ (Jackson Immunoresearch) was used to detect the anti-CD2 MAb, TS2/18, and R-Phycoerythrin conjugated AP goat anti-human IgG F(ab')$_2$ (Jackson Immunoresearch) was used to detect LFA3TIP bound to Jurkat cells. The FITC goat anti-mouse IgG F(ab')$_2$ was diluted to a 1:50 concentration in FACS buffer, and the R-Phycoerythrin conjugated AP goat anti-human IgG F(ab')$_2$ was diluted by 1:20 in FACS buffer. Cells were incubated for 30 minutes on ice, washed 2 times and resuspended in 300 μl of 1×PBS and fluorescence detected on a cell sorter.

For competition studies, Jurkat cells were pelleted in Eppendorf tubes as described above and LFA3TIP was added at a concentration of 10 μg/ml in FACS buffer. Cells were incubated for 30 minutes on ice and washed twice with FACS buffer. Pellets were then resuspended in 100 μl of a 1:100 dilution (in FACS buffer) of anti-CD2 MAb-containing ascites fluids: $T11_1$, $T11_2$ or $T11_3$ (all were gifts of Dr. Ellis Reinherz, Dana Farber Cancer Institute, Boston, Mass.). Cells were incubated for 30 minutes on ice, washed twice and resuspended in a 1:20 dilution of R-phycoerythrin conjugated AP goat anti-human IgG F(ab')$_2$ to detect bound LFA3TIP. After a 30 minute incubation on ice, cells were washed twice and resuspended in 300 μl of 1×PBS and analyzed in a cell sorter.

Figure 14A:
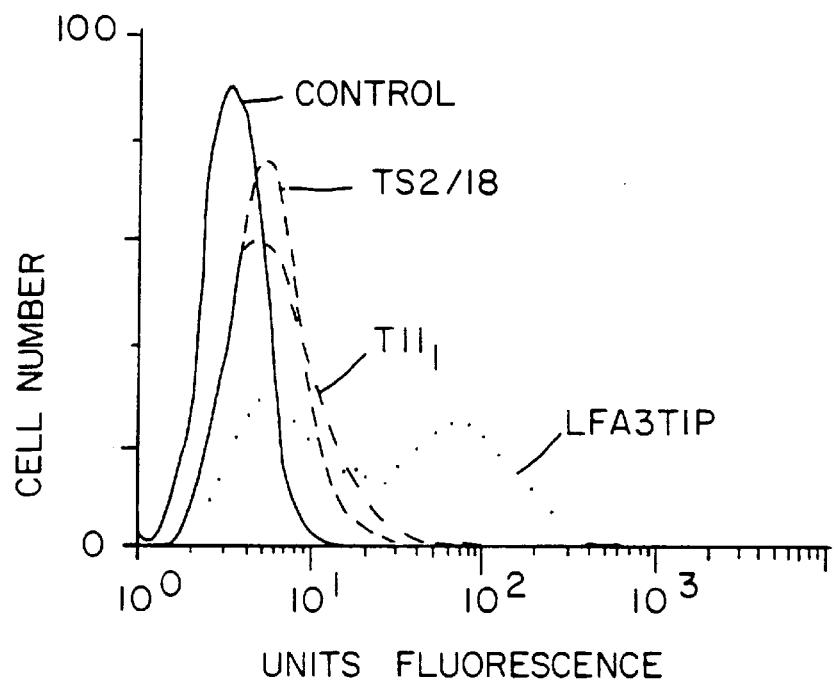
FIGS. 14A and 14B taken together depict results of immunofluorescence flow cytometry by FACS analysis of Jurkat cells incubated with LFA3TIP plus R-Phycoerythrin conjugated anti-human IgG F(ab')$_2$ (dotted lines) in the presence of anti-CD2 MAb TS2/18 plus FITC conjugated goat anti-mouse IgG(H+L) F(ab')$_2$ (small dots in FIG. 14A) or anti-CD2 ascites fluid T11$_1$ (dashes in FIG. 14A), T11$_2$ (dashes in FIG. 14B) or T11$_3$ (small dots in FIG. 14B), plus FITC conjugated goat anti-mouse IgG(H+L) F(ab')$_2$.

The TS2/18 monoclonal antibodies and the monoclonal antibodies in ascites fluid $T11_1$ are specific for the LFA-3 binding domain of CD2. Thus, these antibodies are expected to bind to CD2 molecules on the surface of Jurkat cells and occupy the same site at which LFA3TIP binds. Accordingly, when Jurkat cells were incubated first with an excess of TS2/18 MAb or $T11_1$ ascites fluid, few if any domains are expected to be available for R-Phycoerythrin conjugated LFA3TIP to molecules to bind. As shown in FIG. 14A, preincubation of Jurkat cells with either the TS2/18 NAB or $T11_1$ ascites fluid resulted in few cells being labeled with LFA3TIP. A signal nearly identical to unstained control cells was observed. In contrast, in the absence of either TS2/18 or $T11_1$ ascites fluid, LFA3TIP bound to Jurkat cells and labeled a significant proportion of the cells (FIG. 14A).

Figure 14B:
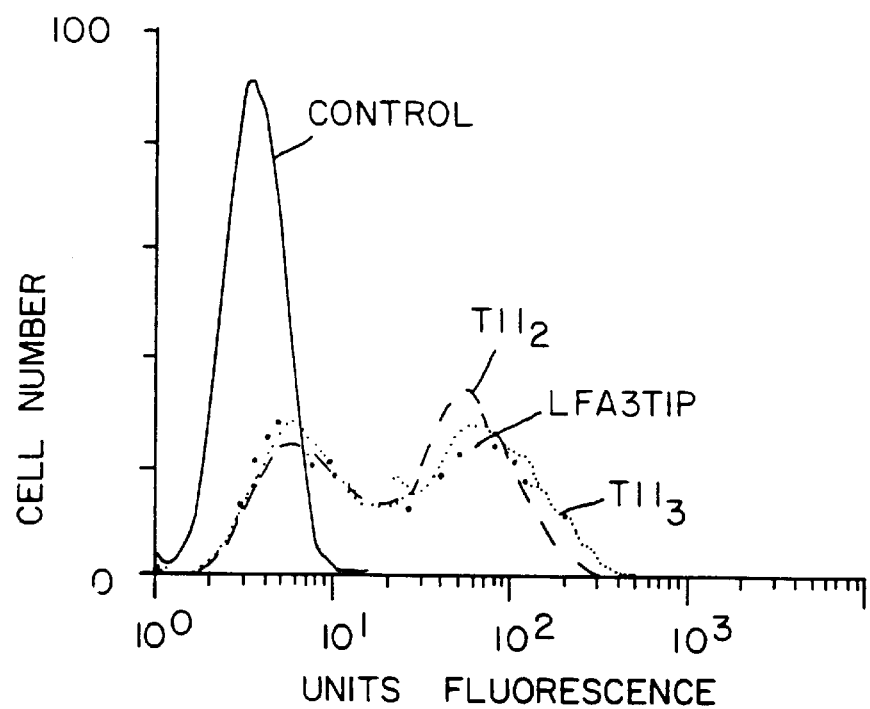

The MAbs present in $T11_2$ and $T11_3$ ascites fluid are specific for CD2, but recognize epitopes distinct from the epitope of CD2 involved in CD2/LFA-3 complex formation. As shown in FIG. 14B, preincubation of Jurkat cells with either $T11_2$ or $T11_3$ ascites fluid did not prevent LFA3TIP from binding to the Jurkat cells. The results shown in FIG. 14A and 14B indicate that LFA3TIP possesses the functional CD2-binding domain LFA-3.

EXAMPLE 15

Mixed Lymphocyte Reaction

A functional assay for the formation of the CD2/LFA-3 complex and T-cell activation is the mixed lymphocyte reaction ("MLR") (see, e.g., Krensky et al., *J. Immunol.*, 131(2), pp. 611–616 (1983); Bradley, "Mixed Lymphocyte Responses", in *Selected Methods in Cellular Immunology* (Mishell and Shiigi, eds.), pp. 162–164 (W. H. Freeman & Co., San Francisco 1980). This assay is based on the activation of T-lymphocytes in a population of peripheral blood lymphocytes ("PBLs") when the T-lymphocytes ("responder cells") recognize alloantigens in nonproliferating allogenic PBLs ("stimulator cells"). Such activation occurs due to cell to cell adhesion, mediated in part by the binding of CD2 molecules on the T-lymphocytes to the LFA-3 molecules on the allogeneic PBLs.

PBLs were purified from 30 ml blood of two allogeneic human donors over a Ficoll-Paque gradient (Pharmacia, Piscataway, N.J. catalog no. 17-0840-02). Blood was diluted at a 1:2 ratio in RPMI medium and overlayed on a Ficoll gradient at a 2:1 ratio (30 ml blood:15 ml Ficoll). Cells were centrifuged through the gradient in a Sorvall RT6000 centrifuge at 1600 rpm, 20° C., for 30 minutes. The interface containing PBLs was collected into 50 ml polypropylene centrifuge tubes (Corning 25331) and topped with RPMI medium. The cells were then pelleted by centrifugation in a Sorvall RT6000 centrifuge at 1400 rpm, 4° C., for 15 minutes. The cells of the pellets were washed twice with 50 ml RPMI and pelleted as described above. PBLs were resuspended in RPMI complete medium (RPMI, 10% Hyclone FCS, 4 mM glutamine, Pen-Strep) to a concentration of $3 \times 10^6$ cells/ml. To produce stimulator cells, PBLs from one of the donors were irradiated at 2000 rads in a Gammacell Irradiator and brought to a final concentration of $3 \times 10^6$ cells/ml.

Figure 15:
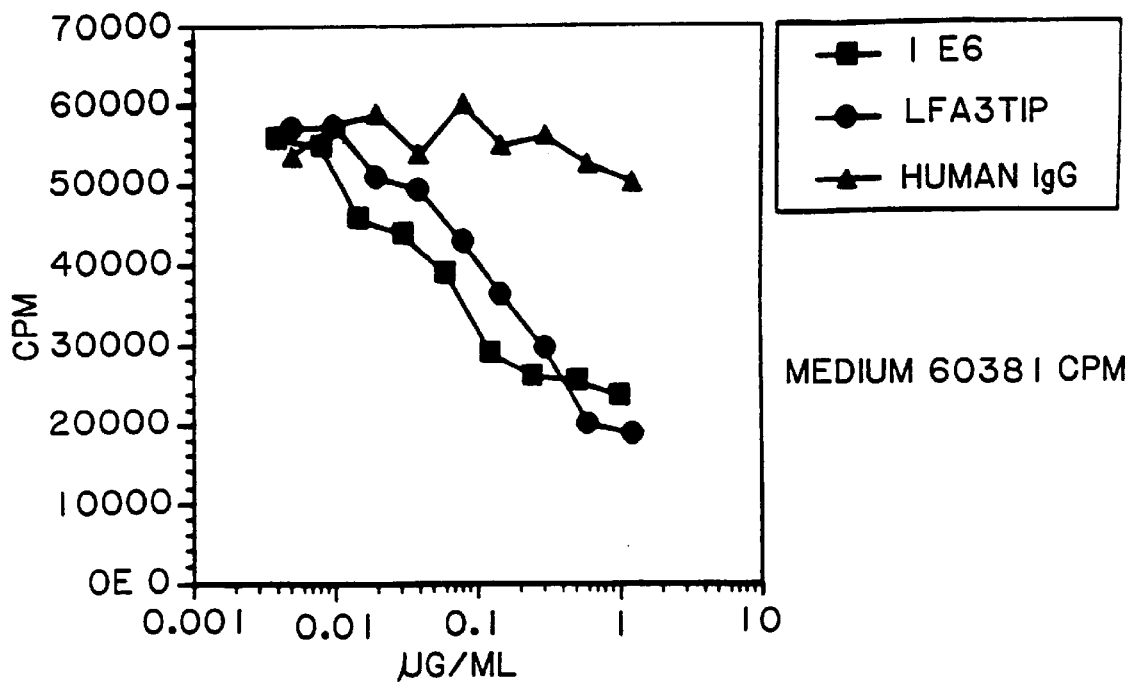
FIG. 15 depicts the results of a human allogeneic mixed lymphocyte reaction (MLR) assay for T-cell activation as measured by $^3$H-thymidine incorporation into T-cells in the presence of anti-LFA-3 MAb 1E6 (closed squares), LFA3TIP (closed circles) and nonspecific human IgG1 (closed triangles).

Antibodies or LFA3TIP samples were added at the concentrations indicated in FIG. 15 to a polystyrene 96 round bottom well plate (Corning 25850). The highest concentration used for both the MAbs and LFA3TIP was 5 μg/ml. All dilutions and incubations were done in RPMI complete medium. Responder cells (nonirradiated) and irradiated stimulator cells were added to wells at a 1:1 ratio at a final concentration of $1.5 \times 10^5$ cells per well each and plates were incubated for five days at 37° C. On the fifth day, cells were pulsed with 1 μCi [methyl-$^3$H] thymidine (New England Nuclear, Boston, Mass., NET-027) for fifteen hours, and harvested on a Tomtech 96 well harvester. Proliferation of the nonirradiated population of T-lymphocytes was measured by determining incorporation of the $^3$H-thymidine into the cells, indicating uptake of the labeled thymidine during T-lymphocyte proliferation. Using this MLR assay, a variety of MAbs and CD2-binding molecules were tested for their effect on CD2/LFA-3 complex formation and T-cell activation.

The anti-LFA-3 MAb 1E6 (produced by hybridoma 1E6-2C12, ATCC accession no. HB 10693) is specific for the CD2-binding domain of LFA-3. As shown in FIG. 15, when 1E6 MAbs were present in the MLR assay, a dose dependent inhibition of T-cell activation was observed. This result is consistent with the view that 1E6 MAbs bind the CD2-binding domain of LFA-3, prevent CD2/LFA-3 complexes from forming between stimulator and responder cells, and thereby inhibit activation of T-cells in the responder cell population.

LFA3TIP exhibited a similar dose dependent inhibition of T-cell activation in the MLR assay (see FIG. 15). To exclude the possibility that the IgG portion of the 1E6 MAbs or LFA3TIP contributed to the observed inhibition of T-cell activation, non-specific human IgG1 (Pierce, Rockford, Ill.) was tested in the MLR assay. As shown in FIG. 15, the nonspecific human IgG did not exhibit the dose dependent inhibition of T-cell activation seen with LFA3TIP or the 1E6 MAbs.

Taken together, these results demonstrate that the inhibitory activity of LFA3TIP on T-cell activation in the MLR assay resides in the LFA-3 domain and not the IgG domain of the fusion protein.

Inhibitory Activity on T-cell Activation of Other Molecules

In addition to LFA3TIP and 1E6 MAbs, the following molecules were also tested for inhibitory activity on T-cell activation in the MLR assay: 7A6 MAb (MAb specific for the CD2-binding domain of LFA-3, produced by hybridoma 7A6-2E5, ATCC accession no. HB 10695), TS2/18 (anti-CD2 MAb, Sanchez-Madrid et al., supra), hIgG (nonspecific total human IgG1), PI-LFA3 (multimeric PI-linked LFA-3 formed by intermolecular hydrophobic interaction at the PI anchor region of each PI-LFA-3 monomer), and a CD4-IgG1 fusion protein (analogous to LFA3TIP, but containing an amino terminal region consisting of a portion of CD4, see, e.g., PCT application WO 89/01940).

Figure 16:
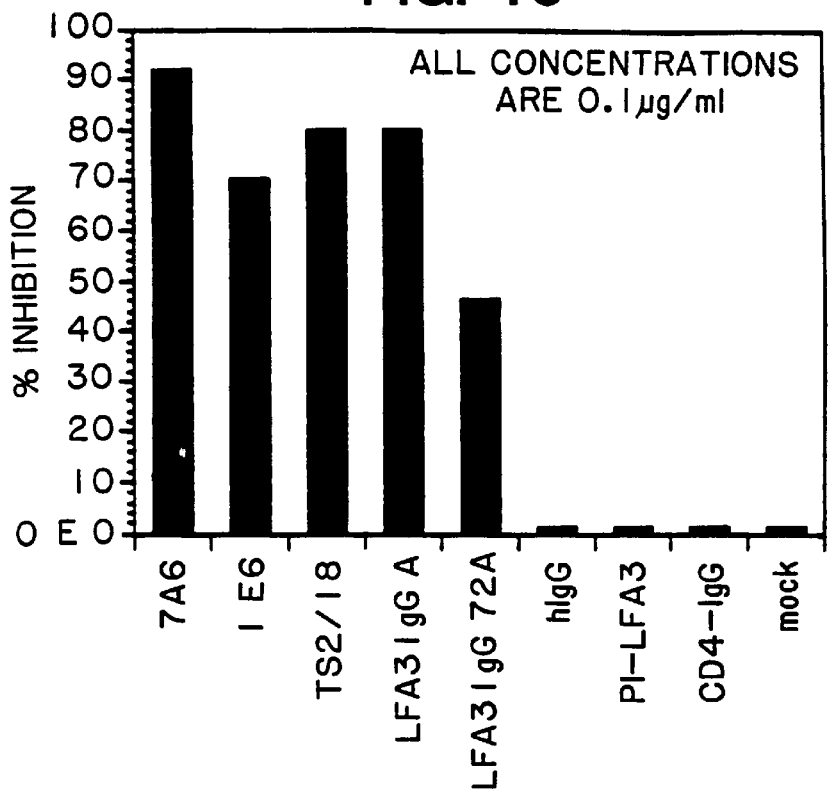
FIG. 16 depicts the results of MLR assays for inhibition of T-cell activation by selected proteins. "7A6" and "1E6" are anti-LFA-3 monoclonal antibodies (MAbs), specific for the CD2-binding domain of LFA-3. "TS2/18" is an anti-CD2 MAb. "LFA3IgGA" and "LFA3IgG72A" are preparations of LFA3TIP differing in purity, i.e., 75% and 50%, respectively. hIgG is nonspecific human IgG. "PI-LFA3" is multimeric PI-linked LFA-3. "CD4-IgG" is a fusion protein consisting of a portion of the CD4 protein fused to a portion of the Fc region of IgG. "Mock" refers to a "mock preparation" purified from COS7 cells transfected with an expression vector pSAB132 lacking the DNA sequence encoding LFA3TIP.

A comparison of the inhibitory activity of each of these molecules is shown in the bar graph of FIG. 16. "LFA3IgGA" and "LFA3IgG72A" in FIG. 16 are preparations of LFA3TIP differing in purity, i.e., 75% and 50% respectively. As a control, a "mock" preparation, purified from COS7 cells transfected with vector DNA alone (i.e., no DNA insert encoding LFA3TIP), was added to show that the inhibitory activity on T-cell activation was not derived from a nonspecific inhibitor contained in conditioned COS7 cell culture medium. The mock preparation contains the contaminant which, as discussed in Example 13, copurifies with LFA3TIP and probably is bovine IgG present in the fetal calf serum of the growth medium. All MLR assays were carried out as described above, except that each preparation of molecules was assayed at a concentration of 0.1 μg protein/ml.

MAbs which recognize the CD2-binding domain of LFA-3 (7A6 and 1E6) or the LFA-3 binding domain of CD2 (TS2/18) exhibited significant inhibitory activity on T-cell activation. The ability of LFA3TIP to inhibit T-cell activation increased with purity (compare LFA3IgG72A, 50% purity, with LFA3IgGA, 75% purity). Nonspecific human IgG1 and the CD4-IgG1 fusion protein failed to inhibit T-cell activation.

The multimeric form of PI-linked LFA-3 also failed to inhibit T-cell activation. Despite the plurality of CD2-binding sites in multimeric PI-linked LFA-3, it appears that this type of multimer neither inhibits nor enhances the human allogeneic MLR.

EXAMPLE 16

PBL Proliferation Assay

Human PBLs were isolated from 20 ml of human donor blood on a Ficoll-Paque gradient, as described above. Purified LFA3TIP was added to 96 well polystyrene round bottom tissue culture plates (Corning 25850) at the concentrations indicated in FIG. 17. PBLs ($1\times10^5$) were then added to each well, and plates were incubated for 3 days at 37° C. All dilutions were carried out in RPMI complete medium (see Example 15). Cells were pulsed after 3 days with 1 μCi/well [methyl-$^3$H] thymidine for 15 hours and harvested on a Tomtech 96 well automatic harvester. As controls, PBL proliferation was measured in growth medium alone and in growth medium supplemented with nonspecific human IgG1.

Figure 17:
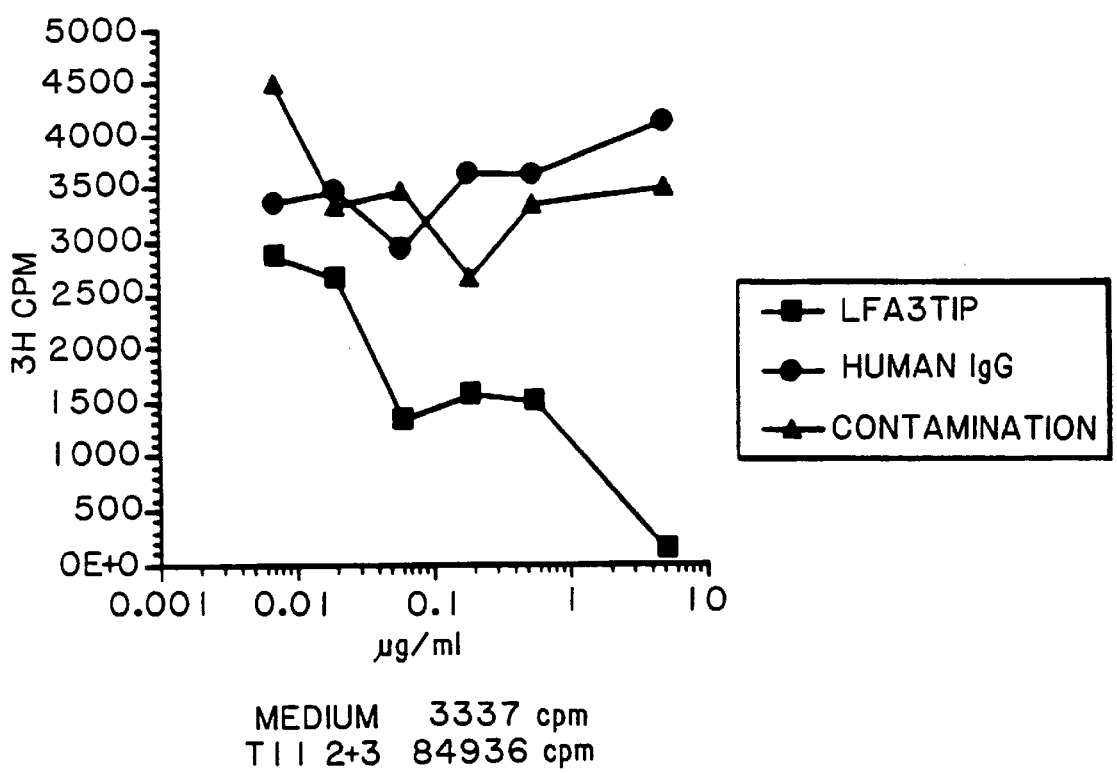
FIG. 17 depicts results of a PBL proliferation assay as measured by incorporation of $^3$H-thymidine. PBL proliferation was measured in the presence of LFA3TIP (closed squares), human IgG (closed circles) and a "mock preparation" containing the contaminant ("contamination") which co-purifies with the LFA3TIP used in this assay (closed triangles).

As shown in FIG. 17, the LFA3TIP preparation inhibited proliferation of PBLs. Nonspecific human IgG1 did not inhibit PBL proliferation.

We also assayed the major contaminant in the LFA3TIP preparation from a mock preparation as described in Example 15. As mentioned in Examples 13 and 15 above, this contaminant is probably bovine IgG from the growth medium. FIG. 17 shows that, as with the nonspecific human IgG1, the contaminant also did not inhibit proliferation of PBLs.

PHA and OKT3 Dependent PBL Proliferation

We next assessed the ability of LFA3TIP to inhibit OKT3 dependent (i.e., anti-CD3 dependent) T-cell proliferation. PBLs were isolated as described above from one healthy human donor. For OKT3 dependent PBL proliferation, aliquots of $1\times10^5$ donor PBLs were incubated for 2 days with 3 ng/ml of OKT3 (Ortho Pharmaceuticals, Raritan, N.J.) alone, and in the presence of LFA3TIP (1 nM and 10 nM) or purified human IgG1 (Pierce Chemical Co., Rockford, Ill.) (1 nM and 10 nM). One aliquot of cells was incubated in medium alone, without OKT3. The cells were then pulsed with [methyl-$^3$H] thymidine as described above. The results of this experiment are shown in FIG. 18.

Figure 18:
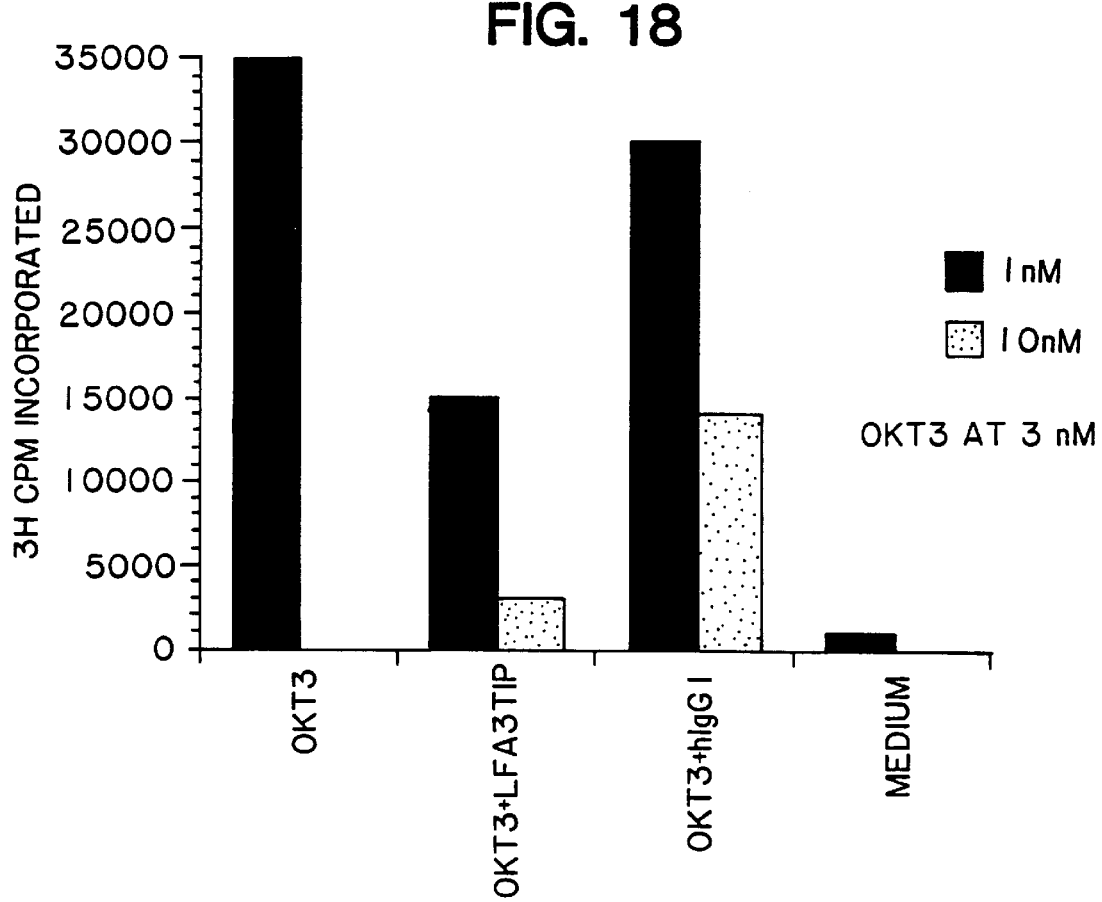
FIG. 18 depicts results of an OKT3 (anti-CD3 MAb) dependent PBL proliferation assay as measured by incorporation of $^3$H-thymidine. PBL proliferation was measured in the presence of 3 nM OKT3 (OKT3), 3 nM OKT3 plus 1 nM or 10 nM LFA3TIP (OKT3+LFA3TIP), 3 nM OKT3 plus 1 nM or 10 nM human IgG1 (OKT3+hIgG1), or medium with no OKT3 present (medium).

The results in FIG. 18 show that LFA3TIP was significantly more effective at inhibiting OKT3 dependent PBL proliferation than the control human IgG1 of irrelevant specificity. As with the results in FIG. 17, this indicates that the ability of LFA3TIP to inhibit PBL proliferation resides primarily in the 92 amino acid LFA-3 region, which contains the CD2 binding domain, and not in the IgG portion of LFA3TIP.

We also assessed the ability of LFA3TIP and various other CD2-binding molecules, as well as, the ability of M57IgG, to inhibit phytohemagglutinin (PHA) dependent PBL proliferation, at both suboptimal and optimal concentrations of PHA.

For this assay, $1\times10^5$ donor cells (human PBLs) were incubated with PHA (Fisher) at 0.1 or 1.0 μg/ml, either alone or in the presence of PI-linked LFA-3 ("PILFA-3", Wallner et al., PCT patent application WO 90/02181), monomeric soluble LFA-3 ("mon LFA-3", consisting of amino acids 29–181 of SEQ ID NO:10), LFA3TIP, M57IgG (see Example 11), a full-length soluble LFA-3-IgG fusion protein ("FLIgG", consisting of amino acids 29–181 of SEQ ID NO:10 fused to a portion of the hinge region and the $C_H2$ and $C_H3$ domains of human IgG1), an anti-CD2 Mab (TS2/18, gift of T. Springer), or an anti-LFA-3 MAb (1E6) produced by hybridoma 1E6-2C12 (ATCC HB 10693). FLIgG was at a concentration of 2 μg/ml; all the other proteins were at a concentration of 5 μg/ml. The cells were then pulsed with [methyl-$^3$H] thymidine as described above. The results are displayed in FIG. 19.

Figure 19:
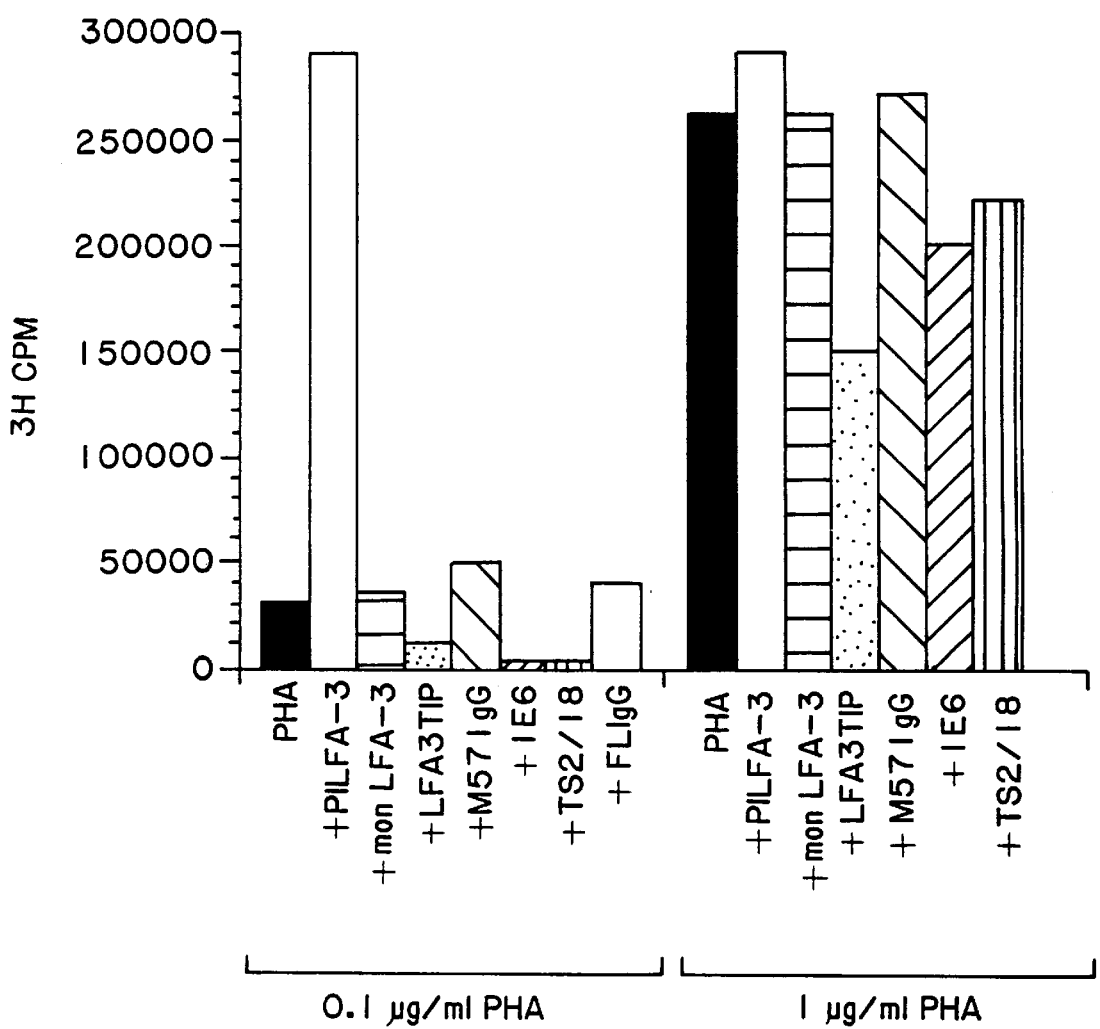
FIG. 19 depicts results of a phytohemagglutinin (PHA) dependent PBL proliferation assay as measured at a suboptimal stimulatory concentration (0.1 μg/ml) and at an optimal stimulatory concentration (1 μg/ml) of PHA. PBL proliferation was measured as indicated in the presence of PHA alone (PHA) and in the presence of PHA plus: PI-linked LFA-3 (+PILFA-3); monomeric soluble LFA-3 (+mon LFA-3); LFA3TIP (+LFA3TIP); an LFA-3-IgG fusion protein which lacks the 10 amino acid M57 region of LFA-3 involved in CD2 binding (+M57IgG); anti-LFA-3 1E6 MAb (+1E6); anti-CD2 TS2/18 MAb (+TS2/18); and a full-length LFA-3-Ig fusion protein (+FLIgG). Each of the added molecules was present at 5 μg/ml.

Referring to FIG. 19, when PHA was incubated with human PBLs at a suboptimal concentration (i.e., 0.1 μg/ml), only PI-linked LFA-3 (PILFA-3) was able to stimulate PBL proliferation. M57IgG, monomeric soluble LFA-3 and FLIgG had no effect on suboptimal PHA-stimulated T-cell proliferation. MAb 1E6 and MAb TS2/18 inhibited proliferation 80–90%; LFA3TIP inhibited 70%.

When PHA was present at an optimal level to stimulate PBL proliferation, LFA3TIP, MAb 1E6 and MAb TS2/18 inhibited T-cell proliferation by 41%, 26% and 20%, respectively.

The results in FIG. 19 indicate that the region of LFA-3 defined by the N-terminal 92 amino acids, containing the CD2-binding domain of LFA-3, is capable of inhibiting PHA dependent PBL proliferation, but that the absence of a portion of the CD2-binding domain, as in M57IgG, or the presence of additional LFA-3 amino acid sequence, as in PI-linked LFA-3, monomeric LFA-3 or FLIgG, diminishes the ability of the CD2-binding domain of LFA-3 to inhibit PHA dependent PBL proliferation.

Taken together, the results indicated that inhibition of PBL proliferation by LFA3TIP is due to its LFA-3 domain.

It will be recognized from the foregoing description that a wide variety of CD2-binding polypeptides in addition to those specifically mentioned, as well as fragments and analogues of such polypeptides, will be useful additional embodiments of the present invention. All such embodiments, and other embodiments that are obvious in view of the teachings herein, are specifically contemplated and are included within the scope of the invention as defined in the following claims.

Deposits

Host cells harboring plasmids bearing DNA sequences according to this invention were deposited under the Budapest Treaty with American Type Culture Collection (ATCC), Rockville, Md. (USA) on Mar. 5, 1991. The deposited cultures are identified as follows:

| plasmid | host strain | Accession No. | Description: (plasmid contains DNA for:) |
|---|---|---|---|
| pPYM57 | E. coli JA221 | 68545 | M57 deletion mutant |
| pPMDRM54-6 | E. coli JA221 | 68542 | M54 deletion mutant |
| pPMDRM55-9 | E. coli JA221 | 68546 | M55 deletion mutant |
| pPMDRM56-C | E. coli JA221 | 68551 | M56 deletion mutant |
| pPMDRM58-15 | E. coli JA221 | 68547 | M58 deletion mutant |
| pPYM63-4 | E. coli JA221 | 68544 | M63 deletion mutant |
| pPYM65-8 | E. coli JA221 | 68552 | M65 deletion mutant |
| pPMDRM100-4 | E. coli JA221 | 68550 | M100 deletion mutant |
| pPMDRM101-1 | E. coli JA221 | 68543 | M101 deletion mutant |
| pPMDRM102-8 | E. coli JA221 | 68548 | M102 deletion mutant |
| pPMDRM3-10 | E. coli JA221 | 68549 | PIM3 deletion mutant |

A host cell harboring a plasmid according to this invention was deposited under the Budapest Treaty with the ATCC on Oct. 1, 1991 is identified as follows:

| plasmid | host strain | Accession No. | Description: (plasmid contains) |
|---|---|---|---|
| pSAB152 | E. coli JA221 | 68720 | Hybrid DNA sequence encoding LFA-3 signal sequence, N-terminal 92 amino acids of LFA-3, 10 amino acids of IgG1 hinge region, $C_H2$ and $C_H3$ IgG1 constant domains. |

A bacteriophage and a bacterial strain carrying a vector referred to herein were deposited under the Budapest Treaty with In Vitro International, Inc., Linthicum, Md. (USA) on May 28, 1987 and May 24, 1988, respectively, and assigned accession numbers IVI-10133 and IVI-10170, respectively. These deposits were transferred to the ATCC on Jun. 20, 1991. The deposits are identified as:

| Designation | Accession No. | Description |
|---|---|---|
| λHT16[λgt10/LFA-3] | 75107 | Contain DNA encoding full length transmembrane LFA-3 |
| E. coli, BGB | 68791 | |

The following hybridoma cell lines referred to herein were deposited under the Budapest Treaty with the ATCC on Mar. 5, 1991:

| Hybridoma | Accession No. | Antibody |
|---|---|---|
| 7A6-2E5 | HB 10695 | 7A6 |
| 1E6-2Cl2 | HB 10693 | 1E6 |

While we have hereinbefore described a number of embodiments of this invention, it is apparent that our basic embodiments can be altered to provide other embodiments that utilize the compositions and processes of this invention. Therefore, it will be appreciated that the scope of this invention includes all alternative embodiments and variations which are defined in the foregoing specification and by the claims appended hereto; and the invention is not to be limited by the specific embodiments that have been presented herein by way of example.

We claim:

1. A method of inhibiting T-cell activation comprising administering to a population of T cells a polypeptide having amino terminal amino acids 1–92 of lymphocyte functioning associated antigen-3 (LFA-3) joined to a protein or polypeptide other than LFA-3, wherein the protein or polypeptide other than LFA-3 comprises a portion of hinge, $C_H2$ and $C_H3$ constant domains of an immunoglobulin.

2. A method of inhibiting T-cell activation comprising administering to a population of T cells a polypeptide having amino terminal amino acids 1–92 of lymphocyte functioning associated antigen-3 (LFA-3) and a portion of an Fc region of a human immunoglobulin IgG1 sufficient to be recognized by protein A.

3. The method of claim 2, wherein the Fc region comprises a hinge region that is capable of forming intermolecular disulfide bonds.

4. A method of inhibiting T-cell activation comprising administering to a population of T cells a polypeptide encoded by a DNA sequence contained in plasmid pSAB152 ATCC Accession Number 68720.

5. A method of inhibiting T-cell activation comprising administering to a population of T cells a polypeptide comprising amino acid residues 29–120 of of SEQ. ID. NO.:43 linked to an Fc portion of IgG.

6. The method of claim 5, wherein the Fc portion of IgG comprises amino acids 121–347 of SEQ ID NO.:43.

* * * * *